(12) United States Patent
Claus et al.

(10) Patent No.: US 12,281,153 B2
(45) Date of Patent: Apr. 22, 2025

(54) COMBINATION THERAPY WITH TARGETED 4-1BB (CD137) AGONISTS

(71) Applicant: Hoffmann-La Roche Inc., Little Falls, NJ (US)

(72) Inventors: Christina Claus, Ennetbaden (CH); Claudia Ferrara Koller, Zug (CH); Christian Klein, Bonstetten (CH); Johannes Sam, Baden (CH); Pablo Umana, Wollerau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 578 days.

(21) Appl. No.: 17/017,942

(22) Filed: Sep. 11, 2020

(65) Prior Publication Data

US 2021/0095002 A1    Apr. 1, 2021

Related U.S. Application Data

(63) Continuation of application No. PCT/EP2019/056067, filed on Mar. 12, 2019.

(30) Foreign Application Priority Data

Mar. 13, 2018 (EP) .................................. 18161340

(51) Int. Cl.
| | |
|---|---|
| *C07K 14/705* | (2006.01) |
| *A61K 39/00* | (2006.01) |
| *A61K 39/395* | (2006.01) |
| *A61P 35/00* | (2006.01) |
| *C07K 16/28* | (2006.01) |
| *C07K 16/30* | (2006.01) |
| *C07K 16/32* | (2006.01) |
| *C07K 16/40* | (2006.01) |

(52) U.S. Cl.
CPC .. *C07K 14/70575* (2013.01); *A61K 39/39541* (2013.01); *A61K 39/39558* (2013.01); *A61P 35/00* (2018.01); *C07K 16/2878* (2013.01); *C07K 16/3007* (2013.01); *C07K 16/32* (2013.01); *C07K 16/40* (2013.01); *A61K 2039/507* (2013.01); *C07K 2317/31* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | |
|---|---|---|
| 5,208,020 A | 5/1993 | Chari et al. |
| 5,677,171 A | 10/1997 | Hudziak et al. |
| 5,821,337 A | 10/1998 | Carter et al. |
| 6,054,297 A | 4/2000 | Carter et al. |
| 6,165,464 A | 12/2000 | Hudziak et al. |
| 6,339,142 B1 | 1/2002 | Basey et al. |
| 6,407,213 B1 | 6/2002 | Carter et al. |
| 6,441,163 B1 | 8/2002 | Chari et al. |
| 6,639,055 B1 | 10/2003 | Carter et al. |
| 6,719,971 B1 | 4/2004 | Carter et al. |
| 6,800,738 B1 | 10/2004 | Carter et al. |
| 7,074,404 B2 | 7/2006 | Basey et al. |
| 7,097,840 B2 | 8/2006 | Erickson et al. |
| 7,560,111 B2 | 7/2009 | Kao et al. |
| 9,011,847 B2 | 4/2015 | Bacac et al. |
| 9,266,938 B2 | 2/2016 | Ast et al. |
| 9,447,159 B2 | 9/2016 | Ast et al. |
| 9,526,797 B2 | 12/2016 | Gerdes et al. |
| 9,758,589 B2 | 9/2017 | Kohrt et al. |
| 9,926,379 B2 | 3/2018 | Bruenker et al. |
| 10,184,009 B2 | 1/2019 | Ast et al. |
| 10,253,110 B2 | 4/2019 | Bacac et al. |
| 10,316,104 B2 | 6/2019 | Ast et al. |
| 10,323,098 B2 | 6/2019 | Ast et al. |
| 10,392,445 B2 * | 8/2019 | Amann ................ A61K 39/395 |
| 10,464,981 B2 | 11/2019 | Amann et al. |
| 10,202,464 B2 | 12/2019 | Ast et al. |
| 10,526,413 B2 | 1/2020 | Amann et al. |
| 10,577,429 B2 | 3/2020 | Bacac et al. |
| 10,603,360 B2 | 3/2020 | Gerdes et al. |
| 11,111,312 B2 | 9/2021 | Ast et al. |
| 11,130,822 B2 | 9/2021 | Ast et al. |
| 11,149,083 B2 | 10/2021 | Amann et al. |
| 11,242,396 B2 | 2/2022 | Bruenker et al. |
| 11,267,903 B2 | 3/2022 | Amann et al. |

(Continued)

FOREIGN PATENT DOCUMENTS

| | | |
|---|---|---|
| CN | 102753195 A | 10/2024 |
| JP | 2013512958 A | 4/2018 |

(Continued)

OTHER PUBLICATIONS

TNFSF9 Genecard, printed Nov. 2022. (Year: 2022).*
Kohrt et al (Stimulation of natural killer cells with a CD137-specific antibody enhances trastuzumab efficacy in xenotransplant models of breast cancer, J Clin Invest. Mar. 2012;122(3)), (Year: 2012).*
TNFRSF9 Genecard, printed Oct. 2023. (Year: 2023).*
Agus, D., et al., "Targeting ligand-activated ErbB2 signaling inhibits breast and prostate tumor growth" Cancer Cell 2(2):127-137 (Aug. 1, 2002).

(Continued)

*Primary Examiner* — Laura B Goddard
*Assistant Examiner* — Sarah A Alsomairy
(74) *Attorney, Agent, or Firm* — Genentech, Inc.

(57) ABSTRACT

The present invention relates to combination therapies employing 4-1BB (CD137) agonists, in particular 4-1BBL trimer containing antigen binding molecules, in combination with HER-2 targeting agents, the use of these combination therapies for the treatment of cancer, and methods of using the combination therapies.

24 Claims, 7 Drawing Sheets
Specification includes a Sequence Listing.

(56) References Cited

U.S. PATENT DOCUMENTS

| | | | |
|---|---|---|---|
| 11,306,154 | B2 | 4/2022 | Amann et al. |
| 11,332,545 | B2 | 5/2022 | Bacac et al. |
| 11,447,558 | B2 | 9/2022 | Ferrara-Koller et al. |
| 2005/0169933 | A1 | 8/2005 | Steeves et al. |
| 2005/0276812 | A1 | 12/2005 | Ebens et al. |
| 2014/0370019 | A1 | 12/2014 | Bruenker et al. |
| 2017/0247467 | A1 | 8/2017 | Amann et al. |
| 2018/0340030 | A1 | 11/2018 | Bruenker et al. |
| 2019/0016771 | A1 | 1/2019 | Amann et al. |
| 2019/0033765 | A1 | 1/2019 | Ast et al. |
| 2019/0185566 | A1 | 6/2019 | Koller et al. |
| 2019/0194291 | A1 | 6/2019 | Bruenker et al. |
| 2019/0211113 | A1 | 7/2019 | Amann et al. |
| 2019/0322763 | A1 | 10/2019 | Ast et al. |
| 2020/0071411 | A1 | 3/2020 | Amann et al. |
| 2020/0188526 | A1 | 6/2020 | Klein et al. |
| 2020/0190206 | A1 | 6/2020 | Koller et al. |
| 2020/0197492 | A1 | 6/2020 | Gerdes et al. |
| 2020/0199234 | A1 | 6/2020 | Georges et al. |
| 2020/0223925 | A1 | 7/2020 | Gasser et al. |
| 2020/0270321 | A1 | 8/2020 | Amann et al. |
| 2020/0325225 | A1 | 10/2020 | Bacac et al. |
| 2020/0325238 | A1 | 10/2020 | Bacac et al. |
| 2020/0347115 | A1 | 11/2020 | Duerr et al. |
| 2020/0392237 | A1 | 12/2020 | Bacac et al. |
| 2021/0009656 | A1 | 1/2021 | Bruenker et al. |
| 2021/0024610 | A1 | 1/2021 | Koller et al. |
| 2021/0054021 | A1 | 2/2021 | Deak Codarri et al. |
| 2021/0095002 | A1 | 4/2021 | Claus et al. |
| 2021/0163617 | A1 | 6/2021 | Ferrara et al. |
| 2021/0188992 | A1 | 6/2021 | Bruenker et al. |
| 2021/0253724 | A1 | 8/2021 | Claus et al. |
| 2021/0292426 | A1 | 9/2021 | Duerr et al. |
| 2021/0324108 | A1 | 10/2021 | Amann et al. |
| 2022/0017637 | A1 | 1/2022 | Gasser et al. |
| 2022/0025046 | A1 | 1/2022 | Amann et al. |
| 2022/0025069 | A1 | 1/2022 | Claus et al. |
| 2022/0073646 | A1 | 3/2022 | Amann et al. |
| 2022/0227878 | A1 | 7/2022 | Bruenker et al. |
| 2022/0242971 | A1 | 8/2022 | Ast et al. |
| 2022/0259327 | A1 | 8/2022 | Amann et al. |
| 2022/0267395 | A1 | 8/2022 | Amann et al. |
| 2022/0281995 | A1 | 9/2022 | Bacac et al. |

FOREIGN PATENT DOCUMENTS

| | | |
|---|---|---|
| KR | 20120102714 A | 9/2018 |
| WO | 2010/10051 A1 | 2/2010 |
| WO | 2012/130831 A1 | 10/2012 |
| WO | 2012/143523 A1 | 10/2012 |
| WO | 2015/091738 A1 | 6/2015 |
| WO | 2016/030350 A1 | 3/2016 |
| WO | 2016/075278 A1 | 5/2016 |
| WO | 2016/156291 A1 | 10/2016 |
| WO | 2016/177802 A1 | 11/2016 |
| WO | 2018/114754 A1 | 6/2018 |
| WO | WO-2019104716 A1 * | 6/2019 |
| WO | 2020/260329 A1 | 12/2020 |
| WO | 2021/140130 A1 | 7/2021 |

OTHER PUBLICATIONS

Bartkowiak, T., et al., "4-1BB Agonists: Multi-Potent Potentiators of Tumor Immunity" Front Oncol 5(117):1-16 (Jun. 8, 2015).
Baselga, J., et al., "Phase II study of weekly intravenous recombinant humanized anti-p185HER2 monoclonal antibody in patients with HER2/neu-overexpressing metastatic breast cancer" J Clin Oncol 14(3):737-744 (Mar. 1, 1996).
Baselga, J., et al., "Recombinant Humanized Anti-HER2 Antibody (Herceptin™). Enhances the Antitumor Activity of Paclitaxel and Doxorubicin against HER2/neu Overexpressing Human Breast Cancer Xenografts" Cancer Res. 58(13):2825-2831 (Jul. 1, 1998).
Baudino, L., et al., "Crucial Role of Aspartic Acid at Position 265 in the CH2 Domain for Murine IgG2a and IgG2b Fc-Associated Effector Functions" J Immunol 181(9):6664-6669 (Nov. 1, 2008).
CAS Registry Database, 180288-69-1, (CAS Registry ID: 180288-69-1: Immunoglobulin G1: Herceptin/Trastuzumab), pp. 1-2 Creation Date Aug. 29, 1996.
Cho, H.S., et al., "Structure of the extracellular region of HER2 alone and in complex with the Herceptin Fab" Nature 421(6924):756-760 (Feb. 13, 2003).
Coussens, L., et al., "Tyrosine Kinase Receptor with Extensive Homology to EGF Receptor Shares Chromosomal Location with neu Oncogene" Science 230(4730):1132-1139 (Dec. 6, 1985).
Diehl, L., et al., "In Vivo Triggering Through 4-1BB Enables Th-Independent Priming of CTL in the Presence of an Intact CD28 Costimulatory Pathway" J Immunol 168(8):3755-3762 (Apr. 15, 2002).
Dubrot, J., et al., "Treatment with anti-CD137 mAbs causes intense accumulations of liver T cells without selective antitumor immunotherapeutic effects in this organ" Cancer Immunol Immun 59(8):1223-1233 (Aug. 1, 2010).
Goodwin, R., et al., "Molecular cloning of a ligand for the inducible T cell gene 4-1BB: a member of an emerging family of cytokines with homology to tumor necrosis factor" Eur J Immunol 23(10):2631-2641 (Oct. 1, 1993).
Gunasekaran, K. et al., "Enhancing Antibody Fc Heterodimer Formation through Electrostatic Steering Effects: Applications to Bi-Specific Molecules and Monovalent IgG" J Biol Chem 285(25):19637-19646 (Jun. 18, 2010).
Harari, D., et al., "Molecular mechanisms underlying ErbB2/HER2 action in breast cancer" Oncogene 19(53):6102-6114 (Dec. 1, 2000).
Harlow, E., et al. Antibodies: A Laboratory Manual "Chapter 14: Immunoassays" Cold Springs Harbor, N.Y.-USA:Cold Spring Harbor Laboratory Press,:553-612 ( 1988).
Hornig, N., et al., "Combination of a Bispecific Antibody and Costimulatory Antibody-Ligand Fusion Proteins for Targeted Cancer Immunotherapy" J Immunother 35(5):418-429 (Jun. 1, 2012).
Hotaling, T. et al., "The humanized anti-HER2 antibody rhuMAb HER2 mediates antibody dependent cell-mediated cytotoxicity via FcγR III" Proceedings of the American Association for Cancer Research (Abstract #3215), 37:471 (Mar. 1996).
Hudziak, R., et al., "p185HER2 monoclonal antibody has antiproliferative effects in vitro and sensitizes human breast tumor cells to tumor necrosis factor" Mol Cell Biol 9(3):1165-1172 (Mar. 1, 1989).
"International Preliminary Report on Patentability—PCT/EP2019/056067" (Report Issuance Date: Sep. 15, 2020—Chapter I),:pp. 1-10 (Sep. 24, 2020).
"International Search Report—PCT/EP2019/056067":pp. 1-15 (Apr. 29, 2019).
Kohrt, H., et al., "Stimulation of natural killer cells with a CD137-specific antibody enhances trastuzumab efficacy in xenotransplant models of breast cancer" J Clin Invest 122(3):1066-1076 (Mar. 1, 2012).
Kwon, B., et al., "cDNA sequences of two inducible T-cell genes" PNAS USA 86(6):1963-1967 (Mar. 1, 1989).
Lewis, G., et al., "Differential responses of human tumor cell lines to anti-p185HER2 monoclonal antibodies" Cancer Immunol Immunother 37(4):255-263 (Sep. 1, 1993).
Li, F., et al., "Inhibitory Fcγ Receptor Engagement Drives Adjuvant and Anti-Tumor Activities of Agonistic CD40 Antibodies" Science 333(6045):1030-1034 (Aug. 19, 2011).
Malik, M.A., et al., "Dose-Response Studies of Recombinant Humanized Monoclonal Antibody 2C4 (Pertuzumab) in Tumor Xenograft Models" Poster (No. 773) American Association for Cancer Research, Washington, D.C.-USA, pp. 1 ( Jul. 11-14, 2003).
Maridana, S., et al., "A Multifunctional Role for Adjuvant Anti-4-1BB Therapy in Augmenting Antitumor Response by Chimeric Antigen Receptor T Cells" Cancer Res (Proceedings: AACR Annual Meeting 2014, Apr. 5-9, 2014, San Diego, CA-US).
Masu, T., et al., "Anti-CD137 monoclonal antibody enhances trastuzumab-induced, natural killer cell-mediated cytotoxicity against pancreatic cancer cell lines with low human epidermal growth factor-like receptor 2 expression" PLOS ONE 13(12):e0200664, 1-18 (Dec. 31, 2018).

(56) References Cited

OTHER PUBLICATIONS

Melero, I. et al., "Monoclonal Antibodies Against the 4-1BB T-cell Activation Molecule Eradicate Established Tumors" Nat Med 3(6):682-685 (Jun. 1, 1997).

Melero, I., et al., "Agonist antibodies to TNFR molecules that costimulate T and NK cells" Clin Cancer Res 19(5):1044-1053 (Mar. 1, 2013).

Merchant, A., et al., "An efficient route to human bispecific IgG" Nat Biotechnol 16(7):677-681 (Jul. 1, 1998).

Misumi, T., et al., "Stimulation of natural killer cells with rhCD137 ligand enhances tumor-targeting antibody efficacy in gastric cancer" PLOS ONE 13(10):e0204880, 1-19 (Oct. 15, 2018).

Mueller, D. et al., "A Novel Antibody-4-1BBL Fusion Protein for Targeted Costimulation in Cancer Immunotherapy" J Immunother 31(8):714-722 (Oct. 1, 2008).

Pegram, M., et al., "Antibody dependent cell-mediated cytotoxicity in breast cancer patients in Phase III clinical trials of a humanized anti-HER2 antibody" P Am Assoc Canc Res (Abstract No. 4044), 38:602 (Mar. 1, 1997).

Shao, Z., et al., "Mini-Review: CD137 ligand, a member of the tumor necrosis factor family, regulates immune responses via reverse signal transduction" J Leukocyte Biol 89(1):21-29 (Jan. 1, 2011).

Simeone, E. et al., "Immunomodulating antibodies in the treatment of metastatic melanoma: The experience with anti-CTLA-4, anti-CD137, and anti-PD1" J Immunotoxcity 9(3):241-247 (Jul. 1, 2012).

Slamon, D., et al., "Human breast cancer: correlation of relapse and survival with amplification of the HER-2/neu oncogene" Science 235(4785):177-182 (Jan. 9, 1987).

Slamon, D., et al., "Studies of the HER-2/neu proto-oncogene in human breast and ovarian cancer" Science 244(4905):707-712 (May 12, 1989).

Slamon, D., et al., "Use of chemotherapy plus a monoclonal antibody against HER2 for metastatic breast cancer that overexpresses HER2" New Engl J Med 344(11):783-792 (Mar. 15, 2001).

Sliwkowski, M.X., "Ready to Parter" Nat Struct Bio 10(3):158-159 (Mar. 1, 2003).

Sliwkowski, M.X., et al., "Nonclinical studies addressing the mechanism of action of trastuzumab (Herceptin)" Semin Oncol 26( Suppl 4 Suppl 12):60-70 (Aug. 1, 1999).

Snell, L., et al., "T-cell intrinsic effects of GITR and 4-1BB during viral infection and cancer immunotherapy" Immunol Rev 244(1):197-217 (Nov. 1, 2011).

Stagg, J., et al., "Anti-ErbB-2 mAb therapy requires type I and II interferons and synergizes with anti-PD-1 or anti-CD137 mAb therapy" PNAS USA 108(17):7142-7147 (Apr. 26, 2011).

US NIH et al., "Clinical Trials Identifier—NCT00309023—Urelumab" Study of BMS-663513 in Patients With Advanced Cancer:1-6 (Oct. 12, 2015).

US NIH, "Clinical Trials Identifier—NCT00612664—Urelumab" Phase II, 2nd Line Melanoma—RAND Monotherapy:1-6 (Oct. 12, 2015).

Vinay, D. et al., "4-1BB signaling beyond T cells" Cell Mol Immunol 8(4):281-284 (Jul. 1, 2011).

Yarden, Y., et al., "Untangling the ErbB Signalling Network" Nat Rev Mol Cell Biol 2(2):127-137 (Feb. 1, 2001).

Zhang, N. et al., "Targeted and untargeted CD137L fusion proteins for the immunotherapy of experimental solid tumors." Clin Cancer Res 13(9):2758-2767 (May 1, 2007).

Amman, Maria et al., "U.S. Appl. No. 18/739,171, filed Jun. 10, 2024, 464 pages".

Holbrook et al., "Stimulation of natural killer cells with a CD137-specific antibody enhances trastuzumab efficacy in xenotransplant models of breast cancer" The Journal of Clinical Investigation 122(3) (Mar. 2012).

Attard, G., et al., "A phase Ib study of pertuzumab, a recombinant humanised antibody to HER2, and docetaxel in patients with advanced solid tumours" Brit J Cancer 97(10):1338-1343 (Nov. 19, 2007).

* cited by examiner

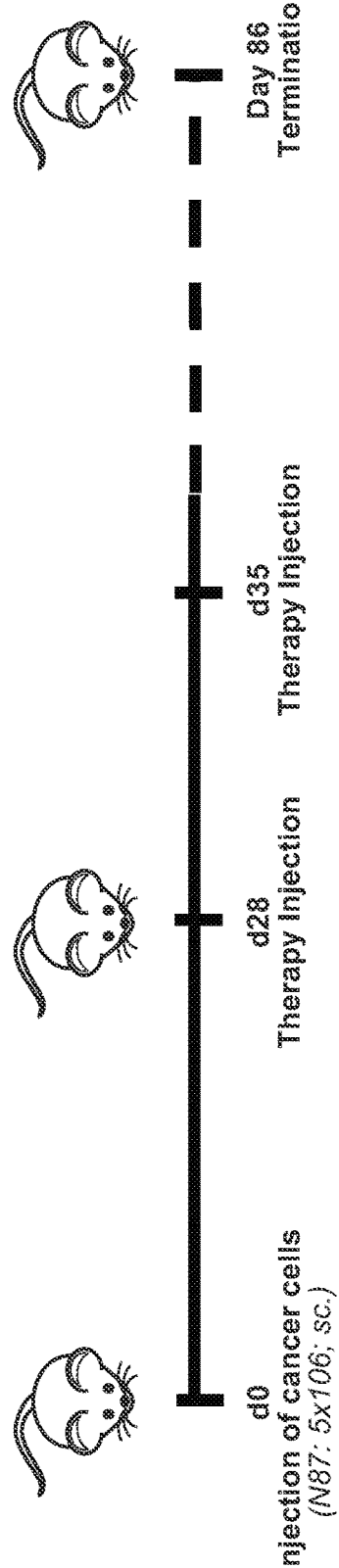

*: Tumor free mice at study termination

SEQUENCE LISTING

```
<160> NUMBER OF SEQ ID NOS: 99

<210> SEQ ID NO 1
<211> LENGTH: 184
<212> TYPE: PRT
<213> ORGANISM: Homo sapiens

<400> SEQUENCE: 1

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
                20                  25                  30

Ile Asp Gly Pro Leu Ser Trp Tyr Ser Asp Pro Gly Leu Ala Gly Val
                35                  40                  45

Ser Leu Thr Gly Gly Leu Ser Tyr Lys Glu Asp Thr Lys Glu Leu Val
        50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
                100                 105                 110
```

```
Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
        180

<210> SEQ ID NO 2
<211> LENGTH: 170
<212> TYPE: PRT
<213> ORGANISM: Homo sapiens

<400> SEQUENCE: 2

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170

<210> SEQ ID NO 3
<211> LENGTH: 175
<212> TYPE: PRT
<213> ORGANISM: Homo sapiens

<400> SEQUENCE: 3

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80
```

```
Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
            130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175
```

<210> SEQ ID NO 4
<211> LENGTH: 203
<212> TYPE: PRT
<213> ORGANISM: Homo sapiens

<400> SEQUENCE: 4

```
Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
            35                  40                  45

Val Leu Leu Ile Asp Gly Pro Leu Ser Trp Tyr Ser Asp Pro Gly Leu
50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
            115                 120                 125

Ala Leu Thr Val Asp Leu Pro Pro Ala Ser Ser Glu Ala Arg Asn Ser
            130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu
            195                 200
```

<210> SEQ ID NO 5
<211> LENGTH: 178
<212> TYPE: PRT
<213> ORGANISM: Homo sapiens

<400> SEQUENCE: 5

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30
```

```
Ile Asp Gly Pro Leu Ser Trp Tyr Ser Asp Pro Gly Leu Ala Gly Val
         35                  40                  45

Ser Leu Thr Gly Gly Leu Ser Tyr Lys Glu Asp Thr Lys Glu Leu Val
 50                  55                  60

Val Ala Lys Ala Gly Val Tyr Tyr Val Phe Phe Gln Leu Glu Leu Arg
 65                  70                  75                  80

Arg Val Val Ala Gly Glu Gly Ser Gly Ser Val Ser Leu Ala Leu His
                 85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu

<210> SEQ ID NO 6
<211> LENGTH: 164
<212> TYPE: PRT
<213> ORGANISM: Homo sapiens

<400> SEQUENCE: 6

Leu Asp Leu Arg Gln Gly Met Phe Ala Gln Leu Val Ala Gln Asn Val
 1               5                  10                  15

Leu Leu Ile Asp Gly Pro Leu Ser Trp Tyr Ser Asp Pro Gly Leu Ala
                 20                  25                  30

Gly Val Ser Leu Thr Gly Gly Leu Ser Tyr Lys Glu Asp Thr Lys Glu
             35                  40                  45

Leu Val Val Ala Lys Ala Gly Val Tyr Tyr Val Phe Phe Gln Leu Glu
 50                  55                  60

Leu Arg Arg Val Val Ala Gly Glu Gly Ser Gly Ser Val Ser Leu Ala
 65                  70                  75                  80

Leu His Leu Gln Pro Leu Arg Ser Ala Ala Gly Ala Ala Ala Leu Ala
                 85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
            115                 120                 125

Gly Val His Leu His Thr Glu Ala Arg Ala Arg His Ala Trp Gln Leu
        130                 135                 140

Thr Gln Gly Ala Thr Val Leu Gly Leu Phe Arg Val Thr Pro Glu Ile
145                 150                 155                 160

Pro Ala Gly Leu

<210> SEQ ID NO 7
<211> LENGTH: 169
<212> TYPE: PRT
<213> ORGANISM: Homo sapiens

<400> SEQUENCE: 7

Asp Pro Ala Gly Leu Leu Asp Leu Arg Gln Gly Met Phe Ala Gln Leu
 1               5                  10                  15
```

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu
                165

<210> SEQ ID NO 8
<211> LENGTH: 197
<212> TYPE: PRT
<213> ORGANISM: Homo sapiens

<400> SEQUENCE: 8

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu
        195

```
<210> SEQ ID NO 9
<211> LENGTH: 5
<212> TYPE: PRT
<213> ORGANISM: Artificial Sequence
<220> FEATURE:
<223> OTHER INFORMATION: FAP(28H1) CDR-H1

<400> SEQUENCE: 9

Ser His Ala Met Ser
1               5

<210> SEQ ID NO 10
<211> LENGTH: 16
<212> TYPE: PRT
<213> ORGANISM: Artificial Sequence
<220> FEATURE:
<223> OTHER INFORMATION: FAP(28H1) CDR-H2

<400> SEQUENCE: 10

Ala Ile Trp Ala Ser Gly Glu Gln Tyr Tyr Ala Asp Ser Val Lys Gly
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: FAP(28H1) CDR-H3

<400> SEQUENCE: 11

Gly Trp Leu Gly Asn Phe Asp Tyr
1               5

<210> SEQ ID NO 12
<211> LENGTH: 12
<212> TYPE: PRT
<213> ORGANISM: Artificial Sequence
<220> FEATURE:
<223> OTHER INFORMATION: FAP(28H1) CDR-L1

<400> SEQUENCE: 12

Arg Ala Ser Gln Ser Val Ser Arg Ser Tyr Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: FAP(28H1) CDR-L2

<400> SEQUENCE: 13

Gly Ala Ser Thr Arg Ala Thr
1               5

<210> SEQ ID NO 14
<211> LENGTH: 9
<212> TYPE: PRT
<213> ORGANISM: Artificial Sequence
<220> FEATURE:
<223> OTHER INFORMATION: FAP(28H1) CDR-L3

<400> SEQUENCE: 14

Gln Gln Gly Gln Val Ile Pro Pro Thr
1               5

<210> SEQ ID NO 15
```

```
<211> LENGTH: 5
<212> TYPE: PRT
<213> ORGANISM: Artificial Sequence
<220> FEATURE:
<223> OTHER INFORMATION: FAP(4B9) CDR-H1

<400> SEQUENCE: 15

Ser Tyr Ala Met Ser
1               5

<210> SEQ ID NO 16
<211> LENGTH: 17
<212> TYPE: PRT
<213> ORGANISM: Artificial Sequence
<220> FEATURE:
<223> OTHER INFORMATION: FAP(4B9) CDR-H2

<400> SEQUENCE: 16

Ala Ile Ile Gly Ser Gly Ala Ser Thr Tyr Tyr Ala Asp Ser Val Lys
1               5                   10                  15

Gly

<210> SEQ ID NO 17
<211> LENGTH: 8
<212> TYPE: PRT
<213> ORGANISM: Artificial Sequence
<220> FEATURE:
<223> OTHER INFORMATION: FAP(4B9) CDR-H3

<400> SEQUENCE: 17

Gly Trp Phe Gly Gly Phe Asn Tyr
1               5

<210> SEQ ID NO 18
<211> LENGTH: 12
<212> TYPE: PRT
<213> ORGANISM: Artificial Sequence
<220> FEATURE:
<223> OTHER INFORMATION: FAP(4B9) CDR-L1

<400> SEQUENCE: 18

Arg Ala Ser Gln Ser Val Ser Arg Ser Tyr Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: FAP(4B9) CDR-L2

<400> SEQUENCE: 19

Val Gly Ser Arg Arg Ala Thr
1               5

<210> SEQ ID NO 20
<211> LENGTH: 9
<212> TYPE: PRT
<213> ORGANISM: Artificial Sequence
<220> FEATURE:
<223> OTHER INFORMATION: FAP(4B9) CDR-L3

<400> SEQUENCE: 20

Gln Gln Gly Ile Met Leu Pro Pro Thr
1               5
```

-continued

```
<210> SEQ ID NO 21
<211> LENGTH: 116
<212> TYPE: PRT
<213> ORGANISM: Artificial Sequence
<220> FEATURE:
<223> OTHER INFORMATION: FAP(28H1) VH

<400> SEQUENCE: 21
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
        115

```
<210> SEQ ID NO 22
<211> LENGTH: 108
<212> TYPE: PRT
<213> ORGANISM: Artificial Sequence
<220> FEATURE:
<223> OTHER INFORMATION: FAP(28H1) VL

<400> SEQUENCE: 22
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

```
<210> SEQ ID NO 23
<211> LENGTH: 117
<212> TYPE: PRT
<213> ORGANISM: Artificial Sequence
<220> FEATURE:
<223> OTHER INFORMATION: FAP(4B9)  VH

<400> SEQUENCE: 23
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 24
<211> LENGTH: 108
<212> TYPE: PRT
<213> ORGANISM: Artificial Sequence
<220> FEATURE:
<223> OTHER INFORMATION: FAP(4B9) VL

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 25
<211> LENGTH: 378
<212> TYPE: PRT
<213> ORGANISM: Artificial Sequence
<220> FEATURE:
<223> OTHER INFORMATION: dimeric hu 4-1BBL (71-254) connected by (G4S)2
      linker

<400> SEQUENCE: 25

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95
```

```
Leu Gln Pro Leu Arg Ser Ala Ala Gly Ala Ala Ala Leu Ala Leu Thr
                100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
        130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Arg Glu Gly Pro Glu Leu Ser Pro Asp Asp Pro Ala Gly Leu
        195                 200                 205

Leu Asp Leu Arg Gln Gly Met Phe Ala Gln Leu Val Ala Gln Asn Val
210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Ala Leu Ala
    290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
        355                 360                 365

Pro Ala Gly Leu Pro Ser Pro Arg Ser Glu
    370                 375

<210> SEQ ID NO 26
<211> LENGTH: 350
<212> TYPE: PRT
<213> ORGANISM: Artificial Sequence
<220> FEATURE:
<223> OTHER INFORMATION: dimeric hu 4-1BBL (85-254) connected by (G4S)2
      linker

<400> SEQUENCE: 26

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
65                  70                  75                  80
```

```
Leu His Leu Gln Pro Leu Arg Ser Ala Ala Gly Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu Gly Gly Gly Ser Gly
                165                 170                 175

Gly Gly Gly Ser Leu Asp Leu Arg Gln Gly Met Phe Ala Gln Leu Val
            180                 185                 190

Ala Gln Asn Val Leu Leu Ile Asp Gly Pro Leu Ser Trp Tyr Ser Asp
        195                 200                 205

Pro Gly Leu Ala Gly Val Ser Leu Thr Gly Gly Leu Ser Tyr Lys Glu
    210                 215                 220

Asp Thr Lys Glu Leu Val Val Ala Lys Ala Gly Val Tyr Tyr Val Phe
225                 230                 235                 240

Phe Gln Leu Glu Leu Arg Arg Val Val Ala Gly Glu Gly Ser Gly Ser
                245                 250                 255

Val Ser Leu Ala Leu His Leu Gln Pro Leu Arg Ser Ala Ala Gly Ala
            260                 265                 270

Ala Ala Leu Ala Leu Thr Val Asp Leu Pro Pro Ala Ser Ser Glu Ala
        275                 280                 285

Arg Asn Ser Ala Phe Gly Phe Gln Gly Arg Leu Leu His Leu Ser Ala
    290                 295                 300

Gly Gln Arg Leu Gly Val His Leu His Thr Glu Ala Arg Ala Arg His
305                 310                 315                 320

Ala Trp Gln Leu Thr Gln Gly Ala Thr Val Leu Gly Leu Phe Arg Val
                325                 330                 335

Thr Pro Glu Ile Pro Ala Gly Leu Pro Ser Pro Arg Ser Glu
            340                 345                 350

<210> SEQ ID NO 27
<211> LENGTH: 360
<212> TYPE: PRT
<213> ORGANISM: Artificial Sequence
<220> FEATURE:
<223> OTHER INFORMATION: dimeric hu 4-1BBL (80-254) connected by (G4S)2
      linker

<400> SEQUENCE: 27

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
```

```
                        85                  90                  95
Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
            130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu Gly
                165                 170                 175

Gly Gly Gly Ser Gly Gly Gly Gly Ser Asp Pro Ala Gly Leu Leu Asp
            180                 185                 190

Leu Arg Gln Gly Met Phe Ala Gln Leu Val Ala Gln Asn Val Leu Leu
            195                 200                 205

Ile Asp Gly Pro Leu Ser Trp Tyr Ser Asp Pro Gly Leu Ala Gly Val
210                 215                 220

Ser Leu Thr Gly Gly Leu Ser Tyr Lys Glu Asp Thr Lys Glu Leu Val
225                 230                 235                 240

Val Ala Lys Ala Gly Val Tyr Tyr Val Phe Phe Gln Leu Glu Leu Arg
                245                 250                 255

Arg Val Val Ala Gly Glu Gly Ser Gly Ser Val Ser Leu Ala Leu His
            260                 265                 270

Leu Gln Pro Leu Arg Ser Ala Ala Gly Ala Ala Ala Leu Ala Leu Thr
            275                 280                 285

Val Asp Leu Pro Pro Ala Ser Ser Glu Ala Arg Asn Ser Ala Phe Gly
            290                 295                 300

Phe Gln Gly Arg Leu Leu His Leu Ser Ala Gly Gln Arg Leu Gly Val
305                 310                 315                 320

His Leu His Thr Glu Ala Arg Ala Arg His Ala Trp Gln Leu Thr Gln
                325                 330                 335

Gly Ala Thr Val Leu Gly Leu Phe Arg Val Thr Pro Glu Ile Pro Ala
            340                 345                 350

Gly Leu Pro Ser Pro Arg Ser Glu
            355                 360

<210> SEQ ID NO 28
<211> LENGTH: 416
<212> TYPE: PRT
<213> ORGANISM: Artificial Sequence
<220> FEATURE:
<223> OTHER INFORMATION: dimeric hu 4-1BBL (52-254) connected by (G4S)2
      linker

<400> SEQUENCE: 28

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
            35                  40                  45

Val Leu Leu Ile Asp Gly Pro Leu Ser Trp Tyr Ser Asp Pro Gly Leu
            50                  55                  60

Ala Gly Val Ser Leu Thr Gly Gly Leu Ser Tyr Lys Glu Asp Thr Lys
65              70                  75                  80
```

```
Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu Gly Gly Gly Gly Ser
        195                 200                 205

Gly Gly Gly Gly Ser Pro Trp Ala Val Ser Gly Ala Arg Ala Ser Pro
    210                 215                 220

Gly Ser Ala Ala Ser Pro Arg Leu Arg Glu Gly Pro Glu Leu Ser Pro
225                 230                 235                 240

Asp Asp Pro Ala Gly Leu Leu Asp Leu Arg Gln Gly Met Phe Ala Gln
                245                 250                 255

Leu Val Ala Gln Asn Val Leu Leu Ile Asp Gly Pro Leu Ser Trp Tyr
            260                 265                 270

Ser Asp Pro Gly Leu Ala Gly Val Ser Leu Thr Gly Gly Leu Ser Tyr
        275                 280                 285

Lys Glu Asp Thr Lys Glu Leu Val Val Ala Lys Ala Gly Val Tyr Tyr
    290                 295                 300

Val Phe Phe Gln Leu Glu Leu Arg Arg Val Val Ala Gly Glu Gly Ser
305                 310                 315                 320

Gly Ser Val Ser Leu Ala Leu His Leu Gln Pro Leu Arg Ser Ala Ala
                325                 330                 335

Gly Ala Ala Ala Leu Ala Leu Thr Val Asp Leu Pro Pro Ala Ser Ser
            340                 345                 350

Glu Ala Arg Asn Ser Ala Phe Gly Phe Gln Gly Arg Leu Leu His Leu
        355                 360                 365

Ser Ala Gly Gln Arg Leu Gly Val His Leu His Thr Glu Ala Arg Ala
    370                 375                 380

Arg His Ala Trp Gln Leu Thr Gln Gly Ala Thr Val Leu Gly Leu Phe
385                 390                 395                 400

Arg Val Thr Pro Glu Ile Pro Ala Gly Leu Pro Ser Pro Arg Ser Glu
                405                 410                 415

<210> SEQ ID NO 29
<211> LENGTH: 366
<212> TYPE: PRT
<213> ORGANISM: Artificial Sequence
<220> FEATURE:
<223> OTHER INFORMATION: dimeric hu 4-1BBL (71-248) connected by (G4S)2
      linker

<400> SEQUENCE: 29

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30
```

Ile Asp Gly Pro Leu Ser Trp Tyr Ser Asp Pro Gly Leu Ala Gly Val
            35                  40                  45

Ser Leu Thr Gly Gly Leu Ser Tyr Lys Glu Asp Thr Lys Glu Leu Val
 50                  55                  60

Val Ala Lys Ala Gly Val Tyr Tyr Val Phe Phe Gln Leu Glu Leu Arg
 65                  70                  75                  80

Arg Val Val Ala Gly Glu Gly Ser Gly Ser Val Ser Leu Ala Leu His
                    85                  90                  95

Leu Gln Pro Leu Arg Ser Ala Ala Gly Ala Ala Leu Ala Leu Thr
                100                 105                 110

Val Asp Leu Pro Pro Ala Ser Ser Glu Ala Arg Asn Ser Ala Phe Gly
                115                 120                 125

Phe Gln Gly Arg Leu Leu His Leu Ser Ala Gly Gln Arg Leu Gly Val
                130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Gly Ser Gly Gly Gly Gly Ser Arg Glu Gly Pro
                180                 185                 190

Glu Leu Ser Pro Asp Asp Pro Ala Gly Leu Leu Asp Leu Arg Gln Gly
                195                 200                 205

Met Phe Ala Gln Leu Val Ala Gln Asn Val Leu Leu Ile Asp Gly Pro
210                 215                 220

Leu Ser Trp Tyr Ser Asp Pro Gly Leu Ala Gly Val Ser Leu Thr Gly
225                 230                 235                 240

Gly Leu Ser Tyr Lys Glu Asp Thr Lys Glu Leu Val Val Ala Lys Ala
                245                 250                 255

Gly Val Tyr Tyr Val Phe Phe Gln Leu Glu Leu Arg Arg Val Val Ala
                260                 265                 270

Gly Glu Gly Ser Gly Ser Val Ser Leu Ala Leu His Leu Gln Pro Leu
                275                 280                 285

Arg Ser Ala Ala Gly Ala Ala Leu Ala Leu Thr Val Asp Leu Pro Pro
                290                 295                 300

Pro Ala Ser Ser Glu Ala Arg Asn Ser Ala Phe Gly Phe Gln Gly Arg
305                 310                 315                 320

Leu Leu His Leu Ser Ala Gly Gln Arg Leu Gly Val His Leu His Thr
                325                 330                 335

Glu Ala Arg Ala Arg His Ala Trp Gln Leu Thr Gln Gly Ala Thr Val
                340                 345                 350

Leu Gly Leu Phe Arg Val Thr Pro Glu Ile Pro Ala Gly Leu
                355                 360                 365

<210> SEQ ID NO 30
<211> LENGTH: 338
<212> TYPE: PRT
<213> ORGANISM: Artificial Sequence
<220> FEATURE:
<223> OTHER INFORMATION: dimeric hu 4-1BBL (85-248) connected by (G4S)2
      linker

<400> SEQUENCE: 30

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala

-continued

Gly Val Ser Leu Thr Gly Gly Leu Ser Tyr Lys Glu Asp Thr Lys Glu
            20                  25                  30
Leu Val Val Ala Lys Ala Gly Val Tyr Tyr Val Phe Phe Gln Leu Glu
        35                  40                  45
Leu Arg Arg Val Val Ala Gly Glu Gly Ser Gly Ser Val Ser Leu Ala
    50                  55                  60
Leu His Leu Gln Pro Leu Arg Ser Ala Ala Gly Ala Ala Ala Leu Ala
65                  70                  75                  80
Leu Thr Val Asp Leu Pro Pro Ala Ser Ser Glu Ala Arg Asn Ser Ala
                85                  90                  95
Phe Gly Phe Gln Gly Arg Leu Leu His Leu Ser Ala Gly Gln Arg Leu
            100                 105                 110
Gly Val His Leu His Thr Glu Ala Arg Ala Arg His Ala Trp Gln Leu
        115                 120                 125
Thr Gln Gly Ala Thr Val Leu Gly Leu Phe Arg Val Thr Pro Glu Ile
    130                 135                 140
Pro Ala Gly Leu Gly Gly Gly Ser Gly Gly Gly Ser Leu Asp
145                 150                 155                 160

Leu Arg Gln Gly Met Phe Ala Gln Leu Val Ala Gln Asn Val Leu Leu
                165                 170                 175
Ile Asp Gly Pro Leu Ser Trp Tyr Ser Asp Pro Gly Leu Ala Gly Val
            180                 185                 190
Ser Leu Thr Gly Gly Leu Ser Tyr Lys Glu Asp Thr Lys Glu Leu Val
        195                 200                 205
Val Ala Lys Ala Gly Val Tyr Tyr Val Phe Phe Gln Leu Glu Leu Arg
225                 210                 215                 220
Arg Val Val Ala Gly Glu Gly Ser Gly Ser Val Ser Leu Ala Leu His
                245                 250                 255
Leu Gln Pro Leu Arg Ser Ala Ala Gly Ala Ala Ala Leu Ala Leu Thr
            260                 265                 270
Val Asp Leu Pro Pro Ala Ser Ser Glu Ala Arg Asn Ser Ala Phe Gly
        275                 280                 285
Phe Gln Gly Arg Leu Leu His Leu Ser Ala Gly Gln Arg Leu Gly Val
    290                 295                 300
His Leu His Thr Glu Ala Arg Ala Arg His Ala Trp Gln Leu Thr Gln
305                 310                 315                 320
Gly Ala Thr Val Leu Gly Leu Phe Arg Val Thr Pro Glu Ile Pro Ala
                325                 330                 335
Gly Leu

<210> SEQ ID NO 31
<211> LENGTH: 348
<212> TYPE: PRT
<213> ORGANISM: Artificial Sequence
<220> FEATURE:
<223> OTHER INFORMATION: dimeric hu 4-1BBL (80-248) connected by (G4S)2
      linker

<400> SEQUENCE: 31

Asp Pro Ala Gly Leu Leu Asp Leu Arg Gln Gly Met Phe Ala Gln Leu
1               5                   10                  15
Val Ala Gln Asn Val Leu Leu Ile Asp Gly Pro Leu Ser Trp Tyr Ser
            20                  25                  30
Asp Pro Gly Leu Ala Gly Val Ser Leu Thr Gly Gly Leu Ser Tyr Lys

```
                35                  40                  45
Glu Asp Thr Lys Glu Leu Val Val Ala Lys Ala Gly Val Tyr Tyr Val
 50                  55                  60

Phe Phe Gln Leu Glu Leu Arg Arg Val Val Ala Gly Glu Gly Ser Gly
 65                  70                  75                  80

Ser Val Ser Leu Ala Leu His Leu Gln Pro Leu Arg Ser Ala Ala Gly
                 85                  90                  95

Ala Ala Ala Leu Ala Leu Thr Val Asp Leu Pro Pro Ala Ser Ser Glu
                100                 105                 110

Ala Arg Asn Ser Ala Phe Gly Phe Gln Gly Arg Leu Leu His Leu Ser
                115                 120                 125

Ala Gly Gln Arg Leu Gly Val His Leu His Thr Glu Ala Arg Ala Arg
130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Gly Gly Gly Ser Gly Gly
                165                 170                 175

Gly Gly Ser Asp Pro Ala Gly Leu Leu Asp Leu Arg Gln Gly Met Phe
            180                 185                 190

Ala Gln Leu Val Ala Gln Asn Val Leu Leu Ile Asp Gly Pro Leu Ser
                195                 200                 205

Trp Tyr Ser Asp Pro Gly Leu Ala Gly Val Ser Leu Thr Gly Gly Leu
210                 215                 220

Ser Tyr Lys Glu Asp Thr Lys Glu Leu Val Val Ala Lys Ala Gly Val
225                 230                 235                 240

Tyr Tyr Val Phe Phe Gln Leu Glu Leu Arg Arg Val Val Ala Gly Glu
                245                 250                 255

Gly Ser Gly Ser Val Ser Leu Ala Leu His Leu Gln Pro Leu Arg Ser
            260                 265                 270

Ala Ala Gly Ala Ala Ala Leu Ala Leu Thr Val Asp Leu Pro Pro Ala
        275                 280                 285

Ser Ser Glu Ala Arg Asn Ser Ala Phe Gly Phe Gln Gly Arg Leu Leu
290                 295                 300

His Leu Ser Ala Gly Gln Arg Leu Gly Val His Leu His Thr Glu Ala
305                 310                 315                 320

Arg Ala Arg His Ala Trp Gln Leu Thr Gln Gly Ala Thr Val Leu Gly
                325                 330                 335

Leu Phe Arg Val Thr Pro Glu Ile Pro Ala Gly Leu
            340                 345

<210> SEQ ID NO 32
<211> LENGTH: 404
<212> TYPE: PRT
<213> ORGANISM: Artificial Sequence
<220> FEATURE:
<223> OTHER INFORMATION: dimeric hu 4-1BBL (52-248) connected by (G4S)2
      linker

<400> SEQUENCE: 32

Pro Trp Ala Val Ser Gly Ala Arg Ala Ser Pro Gly Ser Ala Ala Ser
 1               5                  10                  15

Pro Arg Leu Arg Glu Gly Pro Glu Leu Ser Pro Asp Asp Pro Ala Gly
                20                  25                  30

Leu Leu Asp Leu Arg Gln Gly Met Phe Ala Gln Leu Val Ala Gln Asn
                35                  40                  45
```

```
Val Leu Leu Ile Asp Gly Pro Leu Ser Trp Tyr Ser Asp Pro Gly Leu
 50                  55                  60

Ala Gly Val Ser Leu Thr Gly Gly Leu Ser Tyr Lys Glu Asp Thr Lys
 65                  70                  75                  80

Glu Leu Val Val Ala Lys Ala Gly Val Tyr Tyr Val Phe Phe Gln Leu
                 85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Gly Gly Gly Ser Gly Gly Gly Ser Pro
        195                 200                 205

Trp Ala Val Ser Gly Ala Arg Ala Ser Pro Gly Ser Ala Ser Pro
210                 215                 220

Arg Leu Arg Glu Gly Pro Glu Leu Ser Pro Asp Asp Pro Ala Gly Leu
225                 230                 235                 240

Leu Asp Leu Arg Gln Gly Met Phe Ala Gln Leu Val Ala Gln Asn Val
                245                 250                 255

Leu Leu Ile Asp Gly Pro Leu Ser Trp Tyr Ser Asp Pro Gly Leu Ala
            260                 265                 270

Gly Val Ser Leu Thr Gly Gly Leu Ser Tyr Lys Glu Asp Thr Lys Glu
        275                 280                 285

Leu Val Val Ala Lys Ala Gly Val Tyr Tyr Val Phe Phe Gln Leu Glu
290                 295                 300

Leu Arg Arg Val Val Ala Gly Glu Gly Ser Gly Ser Val Ser Leu Ala
305                 310                 315                 320

Leu His Leu Gln Pro Leu Arg Ser Ala Ala Gly Ala Ala Ala Leu Ala
                325                 330                 335

Leu Thr Val Asp Leu Pro Pro Ala Ser Ser Glu Ala Arg Asn Ser Ala
            340                 345                 350

Phe Gly Phe Gln Gly Arg Leu Leu His Leu Ser Ala Gly Gln Arg Leu
        355                 360                 365

Gly Val His Leu His Thr Glu Ala Arg Ala Arg His Ala Trp Gln Leu
370                 375                 380

Thr Gln Gly Ala Thr Val Leu Gly Leu Phe Arg Val Thr Pro Glu Ile
385                 390                 395                 400

Pro Ala Gly Leu

<210> SEQ ID NO 33
<211> LENGTH: 5
<212> TYPE: PRT
<213> ORGANISM: Artificial Sequence
<220> FEATURE:
<223> OTHER INFORMATION: CEA-HCDR1 (CEACAM5)

<400> SEQUENCE: 33

Asp Thr Tyr Met His
```

<210> SEQ ID NO 34
<211> LENGTH: 17
<212> TYPE: PRT
<213> ORGANISM: Artificial Sequence
<220> FEATURE:
<223> OTHER INFORMATION: CEA-HCDR2 (CEACAM5)

<400> SEQUENCE: 34

Arg Ile Asp Pro Ala Asn Gly Asn Ser Lys Tyr Val Pro Lys Phe Gln
1               5                   10                  15
Gly

<210> SEQ ID NO 35
<211> LENGTH: 12
<212> TYPE: PRT
<213> ORGANISM: Artificial Sequence
<220> FEATURE:
<223> OTHER INFORMATION: CEA-HCDR3 (CEACAM5)

<400> SEQUENCE: 35

Phe Gly Tyr Tyr Val Ser Asp Tyr Ala Met Ala Tyr
1               5                   10

<210> SEQ ID NO 36
<211> LENGTH: 15
<212> TYPE: PRT
<213> ORGANISM: Artificial Sequence
<220> FEATURE:
<223> OTHER INFORMATION: CEA-LCDR1 (CEACAM5)

<400> SEQUENCE: 36

Arg Ala Gly Glu Ser Val Asp Ile Phe Gly Val Gly Phe Leu His
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: CEA-LCDR2 (CEACAM5)

<400> SEQUENCE: 37

Arg Ala Ser Asn Arg Ala Thr
1               5

<210> SEQ ID NO 38
<211> LENGTH: 9
<212> TYPE: PRT
<213> ORGANISM: Artificial Sequence
<220> FEATURE:
<223> OTHER INFORMATION: CEA-LCDR3 (CEACAM5)

<400> SEQUENCE: 38

Gln Gln Thr Asn Glu Asp Pro Tyr Thr
1               5

<210> SEQ ID NO 39
<211> LENGTH: 121
<212> TYPE: PRT
<213> ORGANISM: Artificial Sequence
<220> FEATURE:
<223> OTHER INFORMATION: CEA VH (CEACAM5)

<400> SEQUENCE: 39

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
            115                 120

<210> SEQ ID NO 40
<211> LENGTH: 111
<212> TYPE: PRT
<213> ORGANISM: Artificial Sequence
<220> FEATURE:
<223> OTHER INFORMATION: CEA VL (CEACAM5)

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys
            100                 105                 110

<210> SEQ ID NO 41
<211> LENGTH: 710
<212> TYPE: PRT
<213> ORGANISM: Artificial Sequence
<220> FEATURE:
<223> OTHER INFORMATION: Dimeric hu 4-1BBL (71-248) - CL* Fc knob chain

<400> SEQUENCE: 41

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80
```

```
Arg Val Val Ala Gly Glu Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Gly Ser Gly Gly Gly Ser Arg Glu Gly Pro
                180                 185                 190

Glu Leu Ser Pro Asp Asp Pro Ala Gly Leu Leu Asp Leu Arg Gln Gly
                195                 200                 205

Met Phe Ala Gln Leu Val Ala Gln Asn Val Leu Leu Ile Asp Gly Pro
                210                 215                 220

Leu Ser Trp Tyr Ser Asp Pro Gly Leu Ala Gly Val Ser Leu Thr Gly
225                 230                 235                 240

Gly Leu Ser Tyr Lys Glu Asp Thr Lys Glu Leu Val Val Ala Lys Ala
                245                 250                 255

Gly Val Tyr Tyr Val Phe Phe Gln Leu Glu Leu Arg Arg Val Val Ala
                260                 265                 270

Gly Glu Gly Ser Gly Ser Val Ser Leu Ala Leu His Leu Gln Pro Leu
                275                 280                 285

Arg Ser Ala Ala Gly Ala Ala Ala Leu Ala Leu Thr Val Asp Leu Pro
290                 295                 300

Pro Ala Ser Ser Glu Ala Arg Asn Ser Ala Phe Gly Phe Gln Gly Arg
305                 310                 315                 320

Leu Leu His Leu Ser Ala Gly Gln Arg Leu Gly Val His Leu His Thr
                325                 330                 335

Glu Ala Arg Ala Arg His Ala Trp Gln Leu Thr Gln Gly Ala Thr Val
                340                 345                 350

Leu Gly Leu Phe Arg Val Thr Pro Glu Ile Pro Ala Gly Leu Gly Gly
                355                 360                 365

Gly Gly Ser Gly Gly Gly Ser Arg Thr Val Ala Ala Pro Ser Val
                370                 375                 380

Phe Ile Phe Pro Pro Ser Asp Arg Lys Leu Lys Ser Gly Thr Ala Ser
385                 390                 395                 400

Val Val Cys Leu Leu Asn Asn Phe Tyr Pro Arg Glu Ala Lys Val Gln
                405                 410                 415

Trp Lys Val Asp Asn Ala Leu Gln Ser Gly Asn Ser Gln Glu Ser Val
                420                 425                 430

Thr Glu Gln Asp Ser Lys Asp Ser Thr Tyr Ser Leu Ser Ser Thr Leu
                435                 440                 445

Thr Leu Ser Lys Ala Asp Tyr Glu Lys His Lys Val Tyr Ala Cys Glu
450                 455                 460

Val Thr His Gln Gly Leu Ser Ser Pro Val Thr Lys Ser Phe Asn Arg
465                 470                 475                 480

Gly Glu Cys Asp Lys Thr His Thr Cys Pro Pro Cys Pro Ala Pro Glu
                485                 490                 495
```

```
Ala Ala Gly Gly Pro Ser Val Phe Leu Phe Pro Pro Lys Pro Lys Asp
                500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Gly
        580                 585                 590

Ala Pro Ile Glu Lys Thr Ile Ser Lys Ala Lys Gly Gln Pro Arg Glu
    595                 600                 605

Pro Gln Val Tyr Thr Leu Pro Pro Cys Arg Asp Glu Leu Thr Lys Asn
610                 615                 620

Gln Val Ser Leu Trp Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
        660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
        690                 695                 700

Ser Leu Ser Pro Gly Lys
705                 710

<210> SEQ ID NO 42
<211> LENGTH: 291
<212> TYPE: PRT
<213> ORGANISM: Artificial Sequence
<220> FEATURE:
<223> OTHER INFORMATION: Monomeric hu 4-1BBL (71-248) - CH1*

<400> SEQUENCE: 42

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140
```

```
His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Ser Gly Gly Gly Ser Ala Ser Thr Lys
            180                 185                 190

Gly Pro Ser Val Phe Pro Leu Ala Pro Ser Ser Lys Ser Thr Ser Gly
            195                 200                 205

Gly Thr Ala Ala Leu Gly Cys Leu Val Glu Asp Tyr Phe Pro Glu Pro
        210                 215                 220

Val Thr Val Ser Trp Asn Ser Gly Ala Leu Thr Ser Gly Val His Thr
225                 230                 235                 240

Phe Pro Ala Val Leu Gln Ser Ser Gly Leu Tyr Ser Leu Ser Ser Val
                245                 250                 255

Val Thr Val Pro Ser Ser Ser Leu Gly Thr Gln Thr Tyr Ile Cys Asn
            260                 265                 270

Val Asn His Lys Pro Ser Asn Thr Lys Val Asp Glu Lys Val Glu Pro
        275                 280                 285

Lys Ser Cys
    290

<210> SEQ ID NO 43
<211> LENGTH: 447
<212> TYPE: PRT
<213> ORGANISM: Artificial Sequence
<220> FEATURE:
<223> OTHER INFORMATION: anti-FAP (4B9) Fc hole chain

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

-continued

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
                340                 345                 350

Pro Ser Arg Asp Glu Leu Thr Lys Asn Gln Val Ser Leu Ser Cys Ala
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 44
<211> LENGTH: 215
<212> TYPE: PRT
<213> ORGANISM: Artificial Sequence
<220> FEATURE:
<223> OTHER INFORMATION: anti-FAP (4B9) light chain

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
                20                  25                  30

Tyr Leu Ala Trp Tyr Gln Gln Lys Pro Gly Gln Ala Pro Arg Leu Leu
            35                  40                  45

Ile Asn Val Gly Ser Arg Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

```
Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 45
<211> LENGTH: 722
<212> TYPE: PRT
<213> ORGANISM: Artificial Sequence
<220> FEATURE:
<223> OTHER INFORMATION: Dimeric hu 4-1BBL (71-254) - CL* Fc knob chain

<400> SEQUENCE: 45

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Arg Glu Gly Pro Glu Leu Ser Pro Asp Asp Pro Ala Gly Leu
            195                 200                 205

Leu Asp Leu Arg Gln Gly Met Phe Ala Gln Leu Val Ala Gln Asn Val
        210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270
```

-continued

```
Leu Arg Arg Val Val Ala Gly Glu Gly Ser Gly Ser Val Ser Leu Ala
            275                 280                 285
Leu His Leu Gln Pro Leu Arg Ser Ala Ala Gly Ala Ala Ala Leu Ala
        290                 295                 300
Leu Thr Val Asp Leu Pro Pro Ala Ser Ser Glu Ala Arg Asn Ser Ala
305                 310                 315                 320
Phe Gly Phe Gln Gly Arg Leu Leu His Leu Ser Ala Gly Gln Arg Leu
                325                 330                 335
Gly Val His Leu His Thr Glu Ala Arg Ala Arg His Ala Trp Gln Leu
            340                 345                 350
Thr Gln Gly Ala Thr Val Leu Gly Leu Phe Arg Val Thr Pro Glu Ile
        355                 360                 365
Pro Ala Gly Leu Pro Ser Pro Arg Ser Glu Gly Gly Gly Ser Gly
370                 375                 380
Gly Gly Gly Ser Arg Thr Val Ala Ala Pro Ser Val Phe Ile Phe Pro
385                 390                 395                 400
Pro Ser Asp Arg Lys Leu Lys Ser Gly Thr Ala Ser Val Val Cys Leu
                405                 410                 415
Leu Asn Asn Phe Tyr Pro Arg Glu Ala Lys Val Gln Trp Lys Val Asp
            420                 425                 430
Asn Ala Leu Gln Ser Gly Asn Ser Gln Glu Ser Val Thr Glu Gln Asp
        435                 440                 445
Ser Lys Asp Ser Thr Tyr Ser Leu Ser Ser Thr Leu Thr Leu Ser Lys
    450                 455                 460
Ala Asp Tyr Glu Lys His Lys Val Tyr Ala Cys Glu Val Thr His Gln
465                 470                 475                 480
Gly Leu Ser Ser Pro Val Thr Lys Ser Phe Asn Arg Gly Glu Cys Asp
                485                 490                 495
Lys Thr His Thr Cys Pro Pro Cys Pro Ala Pro Glu Ala Ala Gly Gly
            500                 505                 510
Pro Ser Val Phe Leu Phe Pro Pro Lys Pro Lys Asp Thr Leu Met Ile
        515                 520                 525
Ser Arg Thr Pro Glu Val Thr Cys Val Val Val Asp Val Ser His Glu
    530                 535                 540
Asp Pro Glu Val Lys Phe Asn Trp Tyr Val Asp Gly Val Glu Val His
545                 550                 555                 560
Asn Ala Lys Thr Lys Pro Arg Glu Glu Gln Tyr Asn Ser Thr Tyr Arg
                565                 570                 575
Val Val Ser Val Leu Thr Val Leu His Gln Asp Trp Leu Asn Gly Lys
            580                 585                 590
Glu Tyr Lys Cys Lys Val Ser Asn Lys Ala Leu Gly Ala Pro Ile Glu
        595                 600                 605
Lys Thr Ile Ser Lys Ala Lys Gly Gln Pro Arg Glu Pro Gln Val Tyr
    610                 615                 620
Thr Leu Pro Pro Cys Arg Asp Glu Leu Thr Lys Asn Gln Val Ser Leu
625                 630                 635                 640
Trp Cys Leu Val Lys Gly Phe Tyr Pro Ser Asp Ile Ala Val Glu Trp
                645                 650                 655
Glu Ser Asn Gly Gln Pro Glu Asn Tyr Lys Thr Thr Pro Pro Val
            660                 665                 670
Leu Asp Ser Asp Gly Ser Phe Phe Leu Tyr Ser Lys Leu Thr Val Asp
        675                 680                 685
Lys Ser Arg Trp Gln Gln Gly Asn Val Phe Ser Cys Ser Val Met His
```

```
                    690                 695                 700
Glu Ala Leu His Asn His Tyr Thr Gln Lys Ser Leu Ser Leu Ser Pro
705                 710                 715                 720

Gly Lys

<210> SEQ ID NO 46
<211> LENGTH: 297
<212> TYPE: PRT
<213> ORGANISM: Artificial Sequence
<220> FEATURE:
<223> OTHER INFORMATION: Monomeric hu 4-1BBL (71-254) -CH1*

<400> SEQUENCE: 46

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Ala Ser Thr Lys Gly Pro Ser Val Phe Pro Leu Ala Pro Ser
        195                 200                 205

Ser Lys Ser Thr Ser Gly Gly Thr Ala Ala Leu Gly Cys Leu Val Glu
    210                 215                 220

Asp Tyr Phe Pro Glu Pro Val Thr Val Ser Trp Asn Ser Gly Ala Leu
225                 230                 235                 240

Thr Ser Gly Val His Thr Phe Pro Ala Val Leu Gln Ser Ser Gly Leu
                245                 250                 255

Tyr Ser Leu Ser Ser Val Val Thr Val Pro Ser Ser Ser Leu Gly Thr
            260                 265                 270

Gln Thr Tyr Ile Cys Asn Val Asn His Lys Pro Ser Asn Thr Lys Val
        275                 280                 285

Asp Glu Lys Val Glu Pro Lys Ser Cys
    290                 295

<210> SEQ ID NO 47
<211> LENGTH: 446
<212> TYPE: PRT
<213> ORGANISM: Artificial Sequence
```

<220> FEATURE:
<223> OTHER INFORMATION: anti-FAP(28H1) Fc hole chain

<400> SEQUENCE: 47

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | His |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Ala | Ile | Trp | Ala | Ser | Gly | Glu | Gln | Tyr | Tyr | Ala | Asp | Ser | Val | Lys |
| 50 | | | | | 55 | | | | | 60 | | | | | |
| Gly | Arg | Phe | Thr | Ile | Ser | Arg | Asp | Asn | Ser | Lys | Asn | Thr | Leu | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Ala |
| | | | | 85 | | | | | 90 | | | | | 95 | |
| Lys | Gly | Trp | Leu | Gly | Asn | Phe | Asp | Tyr | Trp | Gly | Gln | Gly | Thr | Leu | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | 115 | | | | | 120 | | | | | 125 | | | |
| Pro | Ser | Ser | Lys | Ser | Thr | Ser | Gly | Gly | Thr | Ala | Ala | Leu | Gly | Cys | Leu |
| 130 | | | | | 135 | | | | | 140 | | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | 195 | | | | | 200 | | | | | 205 | | | |
| Lys | Val | Asp | Lys | Lys | Val | Glu | Pro | Lys | Ser | Cys | Asp | Lys | Thr | His | Thr |
| 210 | | | | | 215 | | | | | 220 | | | | | |
| Cys | Pro | Pro | Cys | Pro | Ala | Pro | Glu | Ala | Ala | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | 275 | | | | | 280 | | | | | 285 | | | |
| Lys | Pro | Arg | Glu | Glu | Gln | Tyr | Asn | Ser | Thr | Tyr | Arg | Val | Val | Ser | Val |
| 290 | | | | | 295 | | | | | 300 | | | | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Ala | Leu | Gly | Ala | Pro | Ile | Glu | Lys | Thr | Ile | Ser |
| | | | | 325 | | | | | 330 | | | | | 335 | |
| Lys | Ala | Lys | Gly | Gln | Pro | Arg | Glu | Pro | Gln | Val | Cys | Thr | Leu | Pro | Pro |
| | | | 340 | | | | | 345 | | | | | 350 | | |
| Ser | Arg | Asp | Glu | Leu | Thr | Lys | Asn | Gln | Val | Ser | Leu | Ser | Cys | Ala | Val |
| | | 355 | | | | | 360 | | | | | 365 | | | |
| Lys | Gly | Phe | Tyr | Pro | Ser | Asp | Ile | Ala | Val | Glu | Trp | Glu | Ser | Asn | Gly |
| 370 | | | | | 375 | | | | | 380 | | | | | |
| Gln | Pro | Glu | Asn | Asn | Tyr | Lys | Thr | Thr | Pro | Pro | Val | Leu | Asp | Ser | Asp |
| 385 | | | | | 390 | | | | | 395 | | | | | 400 |

```
Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 48
<211> LENGTH: 215
<212> TYPE: PRT
<213> ORGANISM: Artificial Sequence
<220> FEATURE:
<223> OTHER INFORMATION: anti-FAP (28H1) light chain

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 49
<211> LENGTH: 445
<212> TYPE: PRT
<213> ORGANISM: Artificial Sequence
<220> FEATURE:
<223> OTHER INFORMATION: DP47 Fc hole chain

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
                35                  40                  45
Ser Ala Ile Ser Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Gly Ser Gly Phe Asp Tyr Trp Gly Gln Gly Thr Leu Val Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
            130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
210                 215                 220
Pro Pro Cys Pro Ala Pro Glu Ala Ala Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Ala Leu Gly Ala Pro Ile Glu Lys Thr Ile Ser Lys
                325                 330                 335
Ala Lys Gly Gln Pro Arg Glu Pro Gln Val Cys Thr Leu Pro Pro Ser
            340                 345                 350
Arg Asp Glu Leu Thr Lys Asn Gln Val Ser Leu Ser Cys Ala Val Lys
            355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Val Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
            435                 440                 445

<210> SEQ ID NO 50
```

<211> LENGTH: 834
<212> TYPE: PRT
<213> ORGANISM: Artificial Sequence
<220> FEATURE:
<223> OTHER INFORMATION: anti-FAP (4B9) Fc hole chain fused to dimeric hu 4-1BBL (71-254)

<400> SEQUENCE: 50

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
```

```
              370                 375                 380
Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Gly Gly
                435                 440                 445

Gly Gly Ser Gly Gly Gly Ser Arg Glu Gly Pro Glu Leu Ser Pro
                450                 455                 460

Asp Asp Pro Ala Gly Leu Leu Asp Leu Arg Gln Gly Met Phe Ala Gln
465                 470                 475                 480

Leu Val Ala Gln Asn Val Leu Leu Ile Asp Gly Pro Leu Ser Trp Tyr
                485                 490                 495

Ser Asp Pro Gly Leu Ala Gly Val Ser Leu Thr Gly Gly Leu Ser Tyr
                500                 505                 510

Lys Glu Asp Thr Lys Glu Leu Val Val Ala Lys Ala Gly Val Tyr Tyr
                515                 520                 525

Val Phe Phe Gln Leu Glu Leu Arg Arg Val Val Ala Gly Glu Gly Ser
530                 535                 540

Gly Ser Val Ser Leu Ala Leu His Leu Gln Pro Leu Arg Ser Ala Ala
545                 550                 555                 560

Gly Ala Ala Ala Leu Ala Leu Thr Val Asp Leu Pro Pro Ala Ser Ser
                565                 570                 575

Glu Ala Arg Asn Ser Ala Phe Gly Phe Gln Gly Arg Leu Leu His Leu
                580                 585                 590

Ser Ala Gly Gln Arg Leu Gly Val His Leu His Thr Glu Ala Arg Ala
                595                 600                 605

Arg His Ala Trp Gln Leu Thr Gln Gly Ala Thr Val Leu Gly Leu Phe
                610                 615                 620

Arg Val Thr Pro Glu Ile Pro Ala Gly Leu Pro Ser Pro Arg Ser Glu
625                 630                 635                 640

Gly Gly Gly Gly Ser Gly Gly Gly Ser Arg Glu Gly Pro Glu Leu
                645                 650                 655

Ser Pro Asp Asp Pro Ala Gly Leu Leu Asp Leu Arg Gln Gly Met Phe
                660                 665                 670

Ala Gln Leu Val Ala Gln Asn Val Leu Leu Ile Asp Gly Pro Leu Ser
                675                 680                 685

Trp Tyr Ser Asp Pro Gly Leu Ala Gly Val Ser Leu Thr Gly Gly Leu
                690                 695                 700

Ser Tyr Lys Glu Asp Thr Lys Glu Leu Val Val Ala Lys Ala Gly Val
705                 710                 715                 720

Tyr Tyr Val Phe Phe Gln Leu Glu Leu Arg Arg Val Val Ala Gly Glu
                725                 730                 735

Gly Ser Gly Ser Val Ser Leu Ala Leu His Leu Gln Pro Leu Arg Ser
                740                 745                 750

Ala Ala Gly Ala Ala Ala Leu Ala Leu Thr Val Asp Leu Pro Pro Ala
                755                 760                 765

Ser Ser Glu Ala Arg Asn Ser Ala Phe Gly Phe Gln Gly Arg Leu Leu
                770                 775                 780

His Leu Ser Ala Gly Gln Arg Leu Gly Val His Leu His Thr Glu Ala
785                 790                 795                 800
```

-continued

```
Arg Ala Arg His Ala Trp Gln Leu Thr Gln Gly Ala Thr Val Leu Gly
                805                 810                 815

Leu Phe Arg Val Thr Pro Glu Ile Pro Ala Gly Leu Pro Ser Pro Arg
            820                 825                 830

Ser Glu

<210> SEQ ID NO 51
<211> LENGTH: 640
<212> TYPE: PRT
<213> ORGANISM: Artificial Sequence
<220> FEATURE:
<223> OTHER INFORMATION: anti-FAP (4B9) Fc knob chain fused to monomeric
      hu 4-1BBL (71-254)

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Arg Glu Gly Pro Glu Leu Ser Pro
    450                 455                 460

Asp Asp Pro Ala Gly Leu Leu Asp Leu Arg Gln Gly Met Phe Ala Gln
465                 470                 475                 480

Leu Val Ala Gln Asn Val Leu Leu Ile Asp Gly Pro Leu Ser Trp Tyr
                485                 490                 495

Ser Asp Pro Gly Leu Ala Gly Val Ser Leu Thr Gly Gly Leu Ser Tyr
            500                 505                 510

Lys Glu Asp Thr Lys Glu Leu Val Val Ala Lys Ala Gly Val Tyr Tyr
        515                 520                 525

Val Phe Phe Gln Leu Glu Leu Arg Arg Val Val Ala Gly Glu Gly Ser
    530                 535                 540

Gly Ser Val Ser Leu Ala Leu His Leu Gln Pro Leu Arg Ser Ala Ala
545                 550                 555                 560

Gly Ala Ala Ala Leu Ala Leu Thr Val Asp Leu Pro Pro Ala Ser Ser
                565                 570                 575

Glu Ala Arg Asn Ser Ala Phe Gly Phe Gln Gly Arg Leu Leu His Leu
            580                 585                 590

Ser Ala Gly Gln Arg Leu Gly Val His Leu His Thr Glu Ala Arg Ala
        595                 600                 605

Arg His Ala Trp Gln Leu Thr Gln Gly Ala Thr Val Leu Gly Leu Phe
    610                 615                 620

Arg Val Thr Pro Glu Ile Pro Ala Gly Leu Pro Ser Pro Arg Ser Glu
625                 630                 635                 640

<210> SEQ ID NO 52
<211> LENGTH: 833
<212> TYPE: PRT
<213> ORGANISM: Artificial Sequence
<220> FEATURE:
<223> OTHER INFORMATION: anti-FAP (28H1) Fc hole chain fused to dimeric
      hu 4-1BBL (71-254)

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val

```
                35                  40                  45
Ser Ala Ile Trp Ala Ser Gly Glu Gln Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Gly Trp Leu Gly Asn Phe Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
                340                 345                 350

Ser Arg Asp Glu Leu Thr Lys Asn Gln Val Ser Leu Ser Cys Ala Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Gly Gly Gly
                435                 440                 445

Gly Ser Gly Gly Gly Gly Ser Arg Glu Gly Pro Glu Leu Ser Pro Asp
450                 455                 460
```

Asp Pro Ala Gly Leu Leu Asp Leu Arg Gln Gly Met Phe Ala Gln Leu
465                 470                 475                 480

Val Ala Gln Asn Val Leu Leu Ile Asp Gly Pro Leu Ser Trp Tyr Ser
            485                 490                 495

Asp Pro Gly Leu Ala Gly Val Ser Leu Thr Gly Gly Leu Ser Tyr Lys
        500                 505                 510

Glu Asp Thr Lys Glu Leu Val Val Ala Lys Ala Gly Val Tyr Tyr Val
    515                 520                 525

Phe Phe Gln Leu Glu Leu Arg Arg Val Val Ala Gly Glu Gly Ser Gly
530                 535                 540

Ser Val Ser Leu Ala Leu His Leu Gln Pro Leu Arg Ser Ala Ala Gly
545                 550                 555                 560

Ala Ala Ala Leu Ala Leu Thr Val Asp Leu Pro Pro Ala Ser Ser Glu
                565                 570                 575

Ala Arg Asn Ser Ala Phe Gly Phe Gln Gly Arg Leu Leu His Leu Ser
            580                 585                 590

Ala Gly Gln Arg Leu Gly Val His Leu His Thr Glu Ala Arg Ala Arg
        595                 600                 605

His Ala Trp Gln Leu Thr Gln Gly Ala Thr Val Leu Gly Leu Phe Arg
610                 615                 620

Val Thr Pro Glu Ile Pro Ala Gly Leu Pro Ser Pro Arg Ser Glu Gly
625                 630                 635                 640

Gly Gly Gly Ser Gly Gly Gly Ser Arg Glu Gly Pro Glu Leu Ser
                645                 650                 655

Pro Asp Asp Pro Ala Gly Leu Leu Asp Leu Arg Gln Gly Met Phe Ala
                660                 665                 670

Gln Leu Val Ala Gln Asn Val Leu Leu Ile Asp Gly Pro Leu Ser Trp
            675                 680                 685

Tyr Ser Asp Pro Gly Leu Ala Gly Val Ser Leu Thr Gly Gly Leu Ser
690                 695                 700

Tyr Lys Glu Asp Thr Lys Glu Leu Val Val Ala Lys Ala Gly Val Tyr
705                 710                 715                 720

Tyr Val Phe Phe Gln Leu Glu Leu Arg Arg Val Val Ala Gly Glu Gly
                725                 730                 735

Ser Gly Ser Val Ser Leu Ala Leu His Leu Gln Pro Leu Arg Ser Ala
            740                 745                 750

Ala Gly Ala Ala Ala Leu Ala Leu Thr Val Asp Leu Pro Pro Ala Ser
        755                 760                 765

Ser Glu Ala Arg Asn Ser Ala Phe Gly Phe Gln Gly Arg Leu Leu His
    770                 775                 780

Leu Ser Ala Gly Gln Arg Leu Gly Val His Leu His Thr Glu Ala Arg
785                 790                 795                 800

Ala Arg His Ala Trp Gln Leu Thr Gln Gly Ala Thr Val Leu Gly Leu
                805                 810                 815

Phe Arg Val Thr Pro Glu Ile Pro Ala Gly Leu Pro Ser Pro Arg Ser
            820                 825                 830

Glu

<210> SEQ ID NO 53
<211> LENGTH: 639
<212> TYPE: PRT
<213> ORGANISM: Artificial Sequence
<220> FEATURE:
<223> OTHER INFORMATION: anti-FAP (28H1) Fc knob chain fused to monomeric hu 4-1BBL (71-254)

<400> SEQUENCE: 53

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
            435                 440                 445

Gly Ser Gly Gly Gly Gly Ser Arg Glu Gly Pro Glu Leu Ser Pro Asp
450                 455                 460

Asp Pro Ala Gly Leu Leu Asp Leu Arg Gln Gly Met Phe Ala Gln Leu
465                 470                 475                 480

Val Ala Gln Asn Val Leu Leu Ile Asp Gly Pro Leu Ser Trp Tyr Ser
            485                 490                 495

Asp Pro Gly Leu Ala Gly Val Ser Leu Thr Gly Gly Leu Ser Tyr Lys
            500                 505                 510

Glu Asp Thr Lys Glu Leu Val Val Ala Lys Ala Gly Val Tyr Tyr Val
            515                 520                 525

Phe Phe Gln Leu Glu Leu Arg Arg Val Val Ala Gly Glu Gly Ser Gly
            530                 535                 540

Ser Val Ser Leu Ala Leu His Leu Gln Pro Leu Arg Ser Ala Ala Gly
545                 550                 555                 560

Ala Ala Ala Leu Ala Leu Thr Val Asp Leu Pro Pro Ala Ser Ser Glu
                565                 570                 575

Ala Arg Asn Ser Ala Phe Gly Phe Gln Gly Arg Leu Leu His Leu Ser
            580                 585                 590

Ala Gly Gln Arg Leu Gly Val His Leu His Thr Glu Ala Arg Ala Arg
            595                 600                 605

His Ala Trp Gln Leu Thr Gln Gly Ala Thr Val Leu Gly Leu Phe Arg
610                 615                 620

Val Thr Pro Glu Ile Pro Ala Gly Leu Pro Ser Pro Arg Ser Glu
625                 630                 635

<210> SEQ ID NO 54
<211> LENGTH: 834
<212> TYPE: PRT
<213> ORGANISM: Artificial Sequence
<220> FEATURE:
<223> OTHER INFORMATION: DP47 Fc hole chain fused to dimeric hu 4-1BBL
      (71-254)

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125
```

```
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
210                 215                 220
Thr Cys Pro Pro Cys Pro Ala Pro Glu Ala Ala Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Gly Ala Pro Ile Glu Lys Thr Ile
                325                 330                 335
Ser Lys Ala Lys Gly Gln Pro Arg Glu Pro Gln Val Cys Thr Leu Pro
            340                 345                 350
Pro Ser Arg Asp Glu Leu Thr Lys Asn Gln Val Ser Leu Ser Cys Ala
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Val Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Gly Gly
        435                 440                 445
Gly Gly Ser Gly Gly Gly Ser Arg Glu Gly Pro Glu Leu Ser Pro
450                 455                 460
Asp Asp Pro Ala Gly Leu Leu Asp Leu Arg Gln Gly Met Phe Ala Gln
465                 470                 475                 480
Leu Val Ala Gln Asn Val Leu Leu Ile Asp Gly Pro Leu Ser Trp Tyr
                485                 490                 495
Ser Asp Pro Gly Leu Ala Gly Val Ser Leu Thr Gly Gly Leu Ser Tyr
            500                 505                 510
Lys Glu Asp Thr Lys Glu Leu Val Val Ala Lys Ala Gly Val Tyr Tyr
        515                 520                 525
Val Phe Phe Gln Leu Glu Leu Arg Arg Val Val Ala Gly Glu Gly Ser
530                 535                 540
```

-continued

Gly Ser Val Ser Leu Ala Leu His Leu Gln Pro Leu Arg Ser Ala Ala
545                 550                 555                 560

Gly Ala Ala Leu Ala Leu Thr Val Asp Leu Pro Pro Ala Ser Ser
            565                 570                 575

Glu Ala Arg Asn Ser Ala Phe Gly Phe Gln Gly Arg Leu Leu His Leu
            580                 585                 590

Ser Ala Gly Gln Arg Leu Gly Val His Leu His Thr Glu Ala Arg Ala
            595                 600                 605

Arg His Ala Trp Gln Leu Thr Gln Gly Ala Thr Val Leu Gly Leu Phe
610                 615                 620

Arg Val Thr Pro Glu Ile Pro Ala Gly Leu Pro Ser Pro Arg Ser Glu
625                 630                 635                 640

Gly Gly Gly Gly Ser Gly Gly Gly Ser Arg Glu Gly Pro Glu Leu
            645                 650                 655

Ser Pro Asp Asp Pro Ala Gly Leu Leu Asp Leu Arg Gln Gly Met Phe
            660                 665                 670

Ala Gln Leu Val Ala Gln Asn Val Leu Leu Ile Asp Gly Pro Leu Ser
            675                 680                 685

Trp Tyr Ser Asp Pro Gly Leu Ala Gly Val Ser Leu Thr Gly Gly Leu
690                 695                 700

Ser Tyr Lys Glu Asp Thr Lys Glu Leu Val Val Ala Lys Ala Gly Val
705                 710                 715                 720

Tyr Tyr Val Phe Phe Gln Leu Glu Leu Arg Arg Val Val Ala Gly Glu
            725                 730                 735

Gly Ser Gly Ser Val Ser Leu Ala Leu His Leu Gln Pro Leu Arg Ser
            740                 745                 750

Ala Ala Gly Ala Ala Leu Ala Leu Thr Val Asp Leu Pro Pro Ala
            755                 760                 765

Ser Ser Glu Ala Arg Asn Ser Ala Phe Gly Phe Gln Gly Arg Leu Leu
770                 775                 780

His Leu Ser Ala Gly Gln Arg Leu Gly Val His Leu His Thr Glu Ala
785                 790                 795                 800

Arg Ala Arg His Ala Trp Gln Leu Thr Gln Gly Ala Thr Val Leu Gly
            805                 810                 815

Leu Phe Arg Val Thr Pro Glu Ile Pro Ala Gly Leu Pro Ser Pro Arg
            820                 825                 830

Ser Glu

<210> SEQ ID NO 55
<211> LENGTH: 640
<212> TYPE: PRT
<213> ORGANISM: Artificial Sequence
<220> FEATURE:
<223> OTHER INFORMATION: DP47 Fc knob chain fused to monomeric hu 4-1BBL
      (71-254)

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ile Gly Ser Gly Ala Ser Thr Tyr Tyr Ala Asp Ser Val
            50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Gly Trp Phe Gly Gly Phe Asn Tyr Trp Gly Gln Gly Thr Leu
        100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
            435                 440                 445

Gly Gly Ser Gly Gly Gly Gly Ser Arg Glu Gly Pro Glu Leu Ser Pro
450                 455                 460

Asp Asp Pro Ala Gly Leu Leu Asp Leu Arg Gln Gly Met Phe Ala Gln
465                 470                 475                 480

Leu Val Ala Gln Asn Val Leu Leu Ile Asp Gly Pro Leu Ser Trp Tyr
```

```
                485                 490                 495
Ser Asp Pro Gly Leu Ala Gly Val Ser Leu Thr Gly Gly Leu Ser Tyr
            500                 505                 510

Lys Glu Asp Thr Lys Glu Leu Val Ala Lys Ala Gly Val Tyr Tyr
            515                 520                 525

Val Phe Phe Gln Leu Glu Leu Arg Arg Val Val Ala Gly Glu Gly Ser
            530                 535                 540

Gly Ser Val Ser Leu Ala Leu His Leu Gln Pro Leu Arg Ser Ala Ala
545                 550                 555                 560

Gly Ala Ala Ala Leu Ala Leu Thr Val Asp Leu Pro Pro Ala Ser Ser
                565                 570                 575

Glu Ala Arg Asn Ser Ala Phe Gly Phe Gln Gly Arg Leu Leu His Leu
                580                 585                 590

Ser Ala Gly Gln Arg Leu Gly Val His Leu His Thr Glu Ala Arg Ala
                595                 600                 605

Arg His Ala Trp Gln Leu Thr Gln Gly Ala Thr Val Leu Gly Leu Phe
                610                 615                 620

Arg Val Thr Pro Glu Ile Pro Ala Gly Leu Pro Ser Pro Arg Ser Glu
625                 630                 635                 640

<210> SEQ ID NO 56
<211> LENGTH: 760
<212> TYPE: PRT
<213> ORGANISM: Homo sapiens

<400> SEQUENCE: 56

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asn Ser Glu Glu Asn Thr Met Arg Ala Leu Thr Leu Lys Asp Ile Leu
            35                  40                  45

Asn Gly Thr Phe Ser Tyr Lys Thr Phe Phe Pro Asn Trp Ile Ser Gly
        50                  55                  60

Gln Glu Tyr Leu His Gln Ser Ala Asp Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asn Gly Lys Phe Leu Ala Tyr Ala
    210                 215                 220
```

```
Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
            245                 250                 255

Ala Lys Asn Pro Val Val Arg Ile Phe Ile Ile Asp Thr Thr Tyr Pro
        260                 265                 270

Ala Tyr Val Gly Pro Gln Glu Val Pro Val Pro Ala Met Ile Ala Ser
    275                 280                 285

Ser Asp Tyr Tyr Phe Ser Trp Leu Thr Trp Val Thr Asp Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
            325                 330                 335

Glu His Ile Glu Glu Ser Arg Thr Gly Trp Ala Gly Gly Phe Phe Val
        340                 345                 350

Ser Thr Pro Val Phe Ser Tyr Asp Ala Ile Ser Tyr Tyr Lys Ile Phe
    355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
            405                 410                 415

Glu Tyr Pro Gly Arg Arg Asn Ile Tyr Arg Ile Ser Ile Gly Ser Tyr
        420                 425                 430

Pro Pro Ser Lys Lys Cys Val Thr Cys His Leu Arg Lys Glu Arg Cys
    435                 440                 445

Gln Tyr Tyr Thr Ala Ser Phe Ser Asp Tyr Ala Lys Tyr Tyr Ala Leu
450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
            485                 490                 495

Ala Leu Lys Asn Ile Gln Leu Pro Lys Glu Ile Lys Lys Leu Glu
        500                 505                 510

Val Asp Glu Ile Thr Leu Trp Tyr Lys Met Ile Leu Pro Pro Gln Phe
    515                 520                 525

Asp Arg Ser Lys Lys Tyr Pro Leu Leu Ile Gln Val Tyr Gly Gly Pro
530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
            565                 570                 575

Thr Ala Phe Gln Gly Asp Lys Leu Leu Tyr Ala Val Tyr Arg Lys Leu
        580                 585                 590

Gly Val Tyr Glu Val Glu Asp Gln Ile Thr Ala Val Arg Lys Phe Ile
    595                 600                 605

Glu Met Gly Phe Ile Asp Glu Lys Arg Ile Ala Ile Trp Gly Trp Ser
610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
```

```
                        645                 650                 655
Ala Ser Val Tyr Thr Glu Arg Phe Met Gly Leu Pro Thr Lys Asp Asp
                660                 665                 670

Asn Leu Glu His Tyr Lys Asn Ser Thr Val Met Ala Arg Ala Glu Tyr
                675                 680                 685

Phe Arg Asn Val Asp Tyr Leu Leu Ile His Gly Thr Ala Asp Asp Asn
            690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
                740                 745                 750

Lys Gln Cys Phe Ser Leu Ser Asp
                755                 760
```

<210> SEQ ID NO 57
<211> LENGTH: 748
<212> TYPE: PRT
<213> ORGANISM: Artificial sequence
<220> FEATURE:
<223> OTHER INFORMATION: hu FAP ectodomain+poly-lys-tag+his6-tag

<400> SEQUENCE: 57

```
Arg Pro Ser Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
                20                  25                  30

Pro Asn Trp Ile Ser Gly Gln Glu Tyr Leu His Gln Ser Ala Asp Asn
                35                  40                  45

Asn Ile Val Leu Tyr Asn Ile Glu Thr Gly Gln Ser Tyr Thr Ile Leu
            50                  55                  60

Ser Asn Arg Thr Met Lys Ser Val Asn Ala Ser Asn Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Ser Asn Gly
                100                 105                 110

Glu Phe Val Arg Gly Asn Glu Leu Pro Arg Pro Ile Gln Tyr Leu Cys
            115                 120                 125

Trp Ser Pro Val Gly Ser Lys Leu Ala Tyr Val Tyr Gln Asn Asn Ile
130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
                180                 185                 190

Lys Phe Leu Ala Tyr Ala Glu Phe Asn Asp Thr Asp Ile Pro Val Ile
            195                 200                 205

Ala Tyr Ser Tyr Tyr Gly Asp Glu Gln Tyr Pro Arg Thr Ile Asn Ile
            210                 215                 220

Pro Tyr Pro Lys Ala Gly Ala Lys Asn Pro Val Val Arg Ile Phe Ile
225                 230                 235                 240

Ile Asp Thr Thr Tyr Pro Ala Tyr Val Gly Pro Gln Glu Val Pro Val
```

```
                    245                 250                 255
Pro Ala Met Ile Ala Ser Ser Asp Tyr Tyr Phe Ser Trp Leu Thr Trp
            260                 265                 270

Val Thr Asp Glu Arg Val Cys Leu Gln Trp Leu Lys Arg Val Gln Asn
            275                 280                 285

Val Ser Val Leu Ser Ile Cys Asp Phe Arg Glu Asp Trp Gln Thr Trp
            290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
                325                 330                 335

Ser Tyr Tyr Lys Ile Phe Ser Asp Lys Asp Gly Tyr Lys His Ile His
                340                 345                 350

Tyr Ile Lys Asp Thr Val Glu Asn Ala Ile Gln Ile Thr Ser Gly Lys
                355                 360                 365

Trp Glu Ala Ile Asn Ile Phe Arg Val Thr Gln Asp Ser Leu Phe Tyr
        370                 375                 380

Ser Ser Asn Glu Phe Glu Tyr Pro Gly Arg Arg Asn Ile Tyr Arg
385                 390                 395                 400

Ile Ser Ile Gly Ser Tyr Pro Pro Ser Lys Lys Cys Val Thr Cys His
                405                 410                 415

Leu Arg Lys Glu Arg Cys Gln Tyr Tyr Thr Ala Ser Phe Ser Asp Tyr
            420                 425                 430

Ala Lys Tyr Tyr Ala Leu Val Cys Tyr Gly Pro Gly Ile Pro Ile Ser
            435                 440                 445

Thr Leu His Asp Gly Arg Thr Asp Gln Glu Ile Lys Ile Leu Glu Glu
        450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
                485                 490                 495

Ile Leu Pro Pro Gln Phe Asp Arg Ser Lys Lys Tyr Pro Leu Leu Ile
                500                 505                 510

Gln Val Tyr Gly Gly Pro Cys Ser Gln Ser Val Arg Ser Val Phe Ala
            515                 520                 525

Val Asn Trp Ile Ser Tyr Leu Ala Ser Lys Glu Gly Met Val Ile Ala
            530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
                580                 585                 590

Ala Ile Trp Gly Trp Ser Tyr Gly Gly Tyr Val Ser Ser Leu Ala Leu
                595                 600                 605

Ala Ser Gly Thr Gly Leu Phe Lys Cys Gly Ile Ala Val Ala Pro Val
            610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670
```

```
Gly Thr Ala Asp Asp Asn Val His Phe Gln Asn Ser Ala Gln Ile Ala
            675                 680                 685

Lys Ala Leu Val Asn Ala Gln Val Asp Phe Gln Ala Met Trp Tyr Ser
        690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His
                740                 745

<210> SEQ ID NO 58
<211> LENGTH: 761
<212> TYPE: PRT
<213> ORGANISM: Mus musculus

<400> SEQUENCE: 58

Met Lys Thr Trp Leu Lys Thr Val Phe Gly Val Thr Thr Leu Ala Ala
1               5                   10                  15

Leu Ala Leu Val Val Ile Cys Ile Val Leu Arg Pro Ser Arg Val Tyr
            20                  25                  30

Lys Pro Glu Gly Asn Thr Lys Arg Ala Leu Thr Leu Lys Asp Ile Leu
        35                  40                  45

Asn Gly Thr Phe Ser Tyr Lys Thr Tyr Phe Pro Asn Trp Ile Ser Glu
    50                  55                  60

Gln Glu Tyr Leu His Gln Ser Glu Asp Asn Ile Val Phe Tyr Asn
65                  70                  75                  80

Ile Glu Thr Arg Glu Ser Tyr Ile Ile Leu Ser Asn Ser Thr Met Lys
                85                  90                  95

Ser Val Asn Ala Thr Asp Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Gln Asn Gly Glu Phe Val Arg Gly Tyr
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Tyr Thr Gly Arg Glu Asn Arg Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asp Gly Lys Phe Leu Ala Tyr Val
    210                 215                 220

Glu Phe Asn Asp Ser Asp Ile Pro Ile Ile Ala Tyr Ser Tyr Tyr Gly
225                 230                 235                 240

Asp Gly Gln Tyr Pro Arg Thr Ile Asn Ile Pro Tyr Pro Lys Ala Gly
                245                 250                 255

Ala Lys Asn Pro Val Val Arg Val Phe Ile Val Asp Thr Thr Tyr Pro
            260                 265                 270

His His Val Gly Pro Met Glu Val Pro Val Pro Glu Met Ile Ala Ser
        275                 280                 285

Ser Asp Tyr Tyr Phe Ser Trp Leu Thr Trp Val Ser Ser Glu Arg Val
```

```
            290                 295                 300
Cys Leu Gln Trp Leu Lys Arg Val Gln Asn Val Ser Val Leu Ser Ile
305                 310                 315                 320

Cys Asp Phe Arg Glu Asp Trp His Ala Trp Glu Cys Pro Lys Asn Gln
                    325                 330                 335

Glu His Val Glu Glu Ser Arg Thr Gly Trp Ala Gly Phe Phe Val
                340                 345                 350

Ser Thr Pro Ala Phe Ser Gln Asp Ala Thr Ser Tyr Tyr Lys Ile Phe
                355                 360                 365

Ser Asp Lys Asp Gly Tyr Lys His Ile His Tyr Ile Lys Asp Thr Val
            370                 375                 380

Glu Asn Ala Ile Gln Ile Thr Ser Gly Lys Trp Glu Ala Ile Tyr Ile
385                 390                 395                 400

Phe Arg Val Thr Gln Asp Ser Leu Phe Tyr Ser Ser Asn Glu Phe Glu
                    405                 410                 415

Gly Tyr Pro Gly Arg Arg Asn Ile Tyr Arg Ile Ser Ile Gly Asn Ser
                420                 425                 430

Pro Pro Ser Lys Lys Cys Val Thr Cys His Leu Arg Lys Glu Arg Cys
                435                 440                 445

Gln Tyr Tyr Thr Ala Ser Phe Ser Tyr Lys Ala Lys Tyr Tyr Ala Leu
            450                 455                 460

Val Cys Tyr Gly Pro Gly Leu Pro Ile Ser Thr Leu His Asp Gly Arg
465                 470                 475                 480

Thr Asp Gln Glu Ile Gln Val Leu Glu Glu Asn Lys Glu Leu Glu Asn
                    485                 490                 495

Ser Leu Arg Asn Ile Gln Leu Pro Lys Val Glu Ile Lys Lys Leu Lys
                500                 505                 510

Asp Gly Gly Leu Thr Phe Trp Tyr Lys Met Ile Leu Pro Pro Gln Phe
                515                 520                 525

Asp Arg Ser Lys Lys Tyr Pro Leu Leu Ile Gln Val Tyr Gly Gly Pro
            530                 535                 540

Cys Ser Gln Ser Val Lys Ser Val Phe Ala Val Asn Trp Ile Thr Tyr
545                 550                 555                 560

Leu Ala Ser Lys Glu Gly Ile Val Ile Ala Leu Val Asp Gly Arg Gly
                565                 570                 575

Thr Ala Phe Gln Gly Asp Lys Phe Leu His Ala Val Tyr Arg Lys Leu
                580                 585                 590

Gly Val Tyr Glu Val Glu Asp Gln Leu Thr Ala Val Arg Lys Phe Ile
            595                 600                 605

Glu Met Gly Phe Ile Asp Glu Arg Ile Ala Ile Trp Gly Trp Ser
610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Ile Tyr Ser Glu Arg Phe Met Gly Leu Pro Thr Lys Asp Asp
                660                 665                 670

Asn Leu Glu His Tyr Lys Asn Ser Thr Val Met Ala Arg Ala Glu Tyr
            675                 680                 685

Phe Arg Asn Val Asp Tyr Leu Leu Ile His Gly Thr Ala Asp Asp Asn
            690                 695                 700

Val His Phe Gln Asn Ser Ala Gln Ile Ala Lys Ala Leu Val Asn Ala
705                 710                 715                 720
```

-continued

```
Gln Val Asp Phe Gln Ala Met Trp Tyr Ser Asp Gln Asn His Gly Ile
            725                 730                 735

Ser Ser Gly Arg Ser Gln Asn His Leu Tyr Thr His Met Thr His Phe
        740                 745                 750

Leu Lys Gln Cys Phe Ser Leu Ser Asp
        755                 760

<210> SEQ ID NO 59
<211> LENGTH: 749
<212> TYPE: PRT
<213> ORGANISM: Artificial sequence
<220> FEATURE:
<223> OTHER INFORMATION: Murine FAP ectodomain+poly-lys-tag+his6-tag

<400> SEQUENCE: 59

Arg Pro Ser Arg Val Tyr Lys Pro Glu Gly Asn Thr Lys Arg Ala Leu
1               5                   10                  15

Thr Leu Lys Asp Ile Leu Asn Gly Thr Phe Ser Tyr Lys Thr Tyr Phe
            20                  25                  30

Pro Asn Trp Ile Ser Glu Gln Glu Tyr Leu His Gln Ser Glu Asp Asp
        35                  40                  45

Asn Ile Val Phe Tyr Asn Ile Glu Thr Arg Glu Ser Tyr Ile Ile Leu
50                  55                  60

Ser Asn Ser Thr Met Lys Ser Val Asn Ala Thr Asp Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Gln Asn Gly
            100                 105                 110

Glu Phe Val Arg Gly Tyr Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
130                 135                 140

Tyr Leu Lys Gln Arg Pro Gly Asp Pro Pro Phe Gln Ile Thr Tyr Thr
145                 150                 155                 160

Gly Arg Glu Asn Arg Ile Phe Asn Gly Ile Pro Asp Trp Val Tyr Glu
                165                 170                 175

Glu Glu Met Leu Ala Thr Lys Tyr Ala Leu Trp Trp Ser Pro Asp Gly
            180                 185                 190

Lys Phe Leu Ala Tyr Val Glu Phe Asn Asp Ser Asp Ile Pro Ile Ile
        195                 200                 205

Ala Tyr Ser Tyr Tyr Gly Asp Gly Gln Tyr Pro Arg Thr Ile Asn Ile
210                 215                 220

Pro Tyr Pro Lys Ala Gly Ala Lys Asn Pro Val Val Arg Val Phe Ile
225                 230                 235                 240

Val Asp Thr Thr Tyr Pro His His Val Gly Pro Met Glu Val Pro Val
                245                 250                 255

Pro Glu Met Ile Ala Ser Ser Asp Tyr Tyr Phe Ser Trp Leu Thr Trp
            260                 265                 270

Val Ser Ser Glu Arg Val Cys Leu Gln Trp Leu Lys Arg Val Gln Asn
        275                 280                 285

Val Ser Val Leu Ser Ile Cys Asp Phe Arg Glu Asp Trp His Ala Trp
290                 295                 300

Glu Cys Pro Lys Asn Gln Glu His Val Glu Glu Ser Arg Thr Gly Trp
305                 310                 315                 320
```

```
Ala Gly Gly Phe Phe Val Ser Thr Pro Ala Phe Ser Gln Asp Ala Thr
            325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
            355                 360                 365

Trp Glu Ala Ile Tyr Ile Phe Arg Val Thr Gln Asp Ser Leu Phe Tyr
            370                 375                 380

Ser Ser Asn Glu Phe Glu Gly Tyr Pro Gly Arg Arg Asn Ile Tyr Arg
385                 390                 395                 400

Ile Ser Ile Gly Asn Ser Pro Pro Ser Lys Lys Cys Val Thr Cys His
            405                 410                 415

Leu Arg Lys Glu Arg Cys Gln Tyr Tyr Thr Ala Ser Phe Ser Tyr Lys
            420                 425                 430

Ala Lys Tyr Tyr Ala Leu Val Cys Tyr Gly Pro Gly Leu Pro Ile Ser
            435                 440                 445

Thr Leu His Asp Gly Arg Thr Asp Gln Glu Ile Gln Val Leu Glu Glu
            450                 455                 460

Asn Lys Glu Leu Glu Asn Ser Leu Arg Asn Ile Gln Leu Pro Lys Val
465                 470                 475                 480

Glu Ile Lys Lys Leu Lys Asp Gly Gly Leu Thr Phe Trp Tyr Lys Met
            485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Lys Ser Val Phe Ala
            515                 520                 525

Val Asn Trp Ile Thr Tyr Leu Ala Ser Lys Glu Gly Ile Val Ile Ala
            530                 535                 540

Leu Val Asp Gly Arg Gly Thr Ala Phe Gln Gly Asp Lys Phe Leu His
545                 550                 555                 560

Ala Val Tyr Arg Lys Leu Gly Val Tyr Glu Val Asp Gln Leu Thr
            565                 570                 575

Ala Val Arg Lys Phe Ile Glu Met Gly Phe Ile Asp Glu Glu Arg Ile
            580                 585                 590

Ala Ile Trp Gly Trp Ser Tyr Gly Gly Tyr Val Ser Ser Leu Ala Leu
            595                 600                 605

Ala Ser Gly Thr Gly Leu Phe Lys Cys Gly Ile Ala Val Ala Pro Val
610                 615                 620

Ser Ser Trp Glu Tyr Tyr Ala Ser Ile Tyr Ser Glu Arg Phe Met Gly
625                 630                 635                 640

Leu Pro Thr Lys Asp Asp Asn Leu Glu His Tyr Lys Asn Ser Thr Val
            645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
            675                 680                 685

Lys Ala Leu Val Asn Ala Gln Val Asp Phe Gln Ala Met Trp Tyr Ser
            690                 695                 700

Asp Gln Asn His Gly Ile Leu Ser Gly Arg Ser Gln Asn His Leu Tyr
705                 710                 715                 720

Thr His Met Thr His Phe Leu Lys Gln Cys Phe Ser Leu Ser Asp Gly
            725                 730                 735
```

Lys Lys Lys Lys Lys Lys Gly His His His His His
            740                 745

<210> SEQ ID NO 60
<211> LENGTH: 748
<212> TYPE: PRT
<213> ORGANISM: Artificial sequence
<220> FEATURE:
<223> OTHER INFORMATION: Cynomolgus FAP ectodomain+poly-lys-tag+his6-tag

<400> SEQUENCE: 60

Arg Pro Pro Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Val Leu Tyr Asn Ile Glu Thr Gly Gln Ser Tyr Thr Ile Leu
    50                  55                  60

Ser Asn Arg Thr Met Lys Ser Val Asn Ala Ser Asn Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Ser Asn Gly
            100                 105                 110

Glu Phe Val Arg Gly Asn Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
    130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Tyr Gly Asp Glu Gln Tyr Pro Arg Thr Ile Asn Ile
    210                 215                 220

Pro Tyr Pro Lys Ala Gly Ala Lys Asn Pro Phe Val Arg Ile Phe Ile
225                 230                 235                 240

Ile Asp Thr Thr Tyr Pro Ala Tyr Val Gly Pro Gln Glu Val Pro Val
                245                 250                 255

Pro Ala Met Ile Ala Ser Ser Asp Tyr Tyr Phe Ser Trp Leu Thr Trp
            260                 265                 270

Val Thr Asp Glu Arg Val Cys Leu Gln Trp Leu Lys Arg Val Gln Asn
        275                 280                 285

Val Ser Val Leu Ser Ile Cys Asp Phe Arg Glu Asp Trp Gln Thr Trp
    290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
                325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
355                 360                 365

Trp Glu Ala Ile Asn Ile Phe Arg Val Thr Gln Asp Ser Leu Phe Tyr
370                 375                 380

Ser Ser Asn Glu Phe Glu Asp Tyr Pro Gly Arg Arg Asn Ile Tyr Arg
385                 390                 395                 400

Ile Ser Ile Gly Ser Tyr Pro Pro Ser Lys Lys Cys Val Thr Cys His
            405                 410                 415

Leu Arg Lys Glu Arg Cys Gln Tyr Tyr Thr Ala Ser Phe Ser Asp Tyr
            420                 425                 430

Ala Lys Tyr Tyr Ala Leu Val Cys Tyr Gly Pro Gly Ile Pro Ile Ser
        435                 440                 445

Thr Leu His Asp Gly Arg Thr Asp Gln Glu Ile Lys Ile Leu Glu Glu
        450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
            485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
        515                 520                 525

Val Asn Trp Ile Ser Tyr Leu Ala Ser Lys Glu Gly Met Val Ile Ala
        530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
            565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
        610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
            645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
            725                 730                 735

Lys Lys Lys Lys Lys Gly His His His His His
            740                 745

<210> SEQ ID NO 61
<211> LENGTH: 702
<212> TYPE: PRT

```
<213> ORGANISM: Homo sapiens

<400> SEQUENCE: 61

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Leu Val His Asn Leu Pro Gln His Leu Phe Gly
        50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Lys Leu Ser
385                 390                 395                 400
```

```
Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
    595                 600                 605

Ala Asn Leu Asn Leu Ser Cys His Ser Ala Ser Asn Pro Ser Pro Gln
610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
    675                 680                 685

Val Gly Ile Met Ile Gly Val Leu Val Gly Val Ala Leu Ile
690                 695                 700

<210> SEQ ID NO 62
<211> LENGTH: 254
<212> TYPE: PRT
<213> ORGANISM: Homo sapiens

<400> SEQUENCE: 62

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80
```

```
Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 63
<211> LENGTH: 205
<212> TYPE: PRT
<213> ORGANISM: Homo sapiens

<400> SEQUENCE: 63

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
    130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
```

```
        195                 200                 205
```

<210> SEQ ID NO 64
<211> LENGTH: 163
<212> TYPE: PRT
<213> ORGANISM: Homo sapiens

<400> SEQUENCE: 64

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln
```

<210> SEQ ID NO 65
<211> LENGTH: 256
<212> TYPE: PRT
<213> ORGANISM: Mus musculus

<400> SEQUENCE: 65

```
Met Gly Asn Asn Cys Tyr Asn Val Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
130                 135                 140

Ser Val Leu Lys Thr Gly Thr Thr Glu Lys Asp Val Val Cys Gly Pro
145                 150                 155                 160
```

```
Pro Val Val Ser Phe Ser Pro Ser Thr Thr Ile Ser Val Thr Pro Glu
            165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
            195                 200                 205

Ser Val Leu Lys Trp Ile Arg Lys Lys Phe Pro His Ile Phe Lys Gln
            210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255

<210> SEQ ID NO 66
<211> LENGTH: 254
<212> TYPE: PRT
<213> ORGANISM: cynomolgus

<400> SEQUENCE: 66

Met Gly Asn Ser Cys Tyr Asn Ile Val Ala Thr Leu Leu Leu Val Leu
1               5                   10                  15

Asn Phe Glu Arg Thr Arg Ser Leu Gln Asp Leu Cys Ser Asn Cys Pro
            20                  25                  30

Ala Gly Thr Phe Cys Asp Asn Asn Arg Ser Gln Ile Cys Ser Pro Cys
            35                  40                  45

Pro Pro Asn Ser Phe Ser Ser Ala Gly Gly Gln Arg Thr Cys Asp Ile
50                  55                  60

Cys Arg Gln Cys Lys Gly Val Phe Lys Thr Arg Lys Glu Cys Ser Ser
65                  70                  75                  80

Thr Ser Asn Ala Glu Cys Asp Cys Ile Ser Gly Tyr His Cys Leu Gly
            85                  90                  95

Ala Glu Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Ala Thr Pro Pro Ala
            165                 170                 175

Pro Ala Arg Glu Pro Gly His Ser Pro Gln Ile Ile Phe Phe Leu Ala
            180                 185                 190

Leu Thr Ser Thr Val Val Leu Phe Leu Phe Phe Leu Val Leu Arg
            195                 200                 205

Phe Ser Val Val Lys Arg Ser Arg Lys Lys Leu Leu Tyr Ile Phe Lys
            210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu
                245                 250

<210> SEQ ID NO 67
<211> LENGTH: 5
<212> TYPE: PRT
```

```
<213> ORGANISM: Artificial Sequence
<220> FEATURE:
<223> OTHER INFORMATION: G4S peptide linker

<400> SEQUENCE: 67

Gly Gly Gly Gly Ser
1               5

<210> SEQ ID NO 68
<211> LENGTH: 10
<212> TYPE: PRT
<213> ORGANISM: Artificial Sequence
<220> FEATURE:
<223> OTHER INFORMATION: (G4S)2

<400> SEQUENCE: 68

Gly Gly Gly Gly Ser Gly Gly Gly Gly Ser
1               5                   10

<210> SEQ ID NO 69
<211> LENGTH: 10
<212> TYPE: PRT
<213> ORGANISM: Artificial Sequence
<220> FEATURE:
<223> OTHER INFORMATION: (SG4)2

<400> SEQUENCE: 69

Ser Gly Gly Gly Gly Ser Gly Gly Gly Gly
1               5                   10

<210> SEQ ID NO 70
<211> LENGTH: 14
<212> TYPE: PRT
<213> ORGANISM: Artificial Sequence
<220> FEATURE:
<223> OTHER INFORMATION: peptide linker

<400> SEQUENCE: 70

Gly Gly Gly Gly Ser Gly Gly Gly Gly Ser Gly Gly Gly Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: peptide linker

<400> SEQUENCE: 71

Gly Ser Pro Gly Ser Ser Ser Ser Gly Ser
1               5                   10

<210> SEQ ID NO 72
<211> LENGTH: 15
<212> TYPE: PRT
<213> ORGANISM: Artificial Sequence
<220> FEATURE:
<223> OTHER INFORMATION: peptide linker 2

<400> SEQUENCE: 72

Gly Gly Gly Gly Ser Gly Gly Gly Gly Ser Gly Gly Gly Gly Ser
1               5                   10                  15

<210> SEQ ID NO 73
<211> LENGTH: 20
<212> TYPE: PRT
<213> ORGANISM: Artificial Sequence
```

```
<220> FEATURE:
<223> OTHER INFORMATION: peptide linker 3

<400> SEQUENCE: 73

Gly Gly Gly Gly Ser Gly Gly Gly Ser Gly Gly Gly Gly Ser Gly
1               5                   10                  15

Gly Gly Gly Ser
            20

<210> SEQ ID NO 74
<211> LENGTH: 8
<212> TYPE: PRT
<213> ORGANISM: Artificial Sequence
<220> FEATURE:
<223> OTHER INFORMATION: peptide linker 4

<400> SEQUENCE: 74

Gly Ser Gly Ser Gly Ser Gly Ser
1               5

<210> SEQ ID NO 75
<211> LENGTH: 8
<212> TYPE: PRT
<213> ORGANISM: Artificial Sequence
<220> FEATURE:
<223> OTHER INFORMATION: peptide linker 5

<400> SEQUENCE: 75

Gly Ser Gly Ser Gly Asn Gly Ser
1               5

<210> SEQ ID NO 76
<211> LENGTH: 8
<212> TYPE: PRT
<213> ORGANISM: Artificial Sequence
<220> FEATURE:
<223> OTHER INFORMATION: peptide linker 6

<400> SEQUENCE: 76

Gly Gly Ser Gly Ser Gly Ser Gly
1               5

<210> SEQ ID NO 77
<211> LENGTH: 6
<212> TYPE: PRT
<213> ORGANISM: Artificial Sequence
<220> FEATURE:
<223> OTHER INFORMATION: peptide linker 7

<400> SEQUENCE: 77

Gly Gly Ser Gly Ser Gly
1               5

<210> SEQ ID NO 78
<211> LENGTH: 4
<212> TYPE: PRT
<213> ORGANISM: Artificial Sequence
<220> FEATURE:
<223> OTHER INFORMATION: peptide linker 8

<400> SEQUENCE: 78

Gly Gly Ser Gly
1

<210> SEQ ID NO 79
<211> LENGTH: 8
```

```
<212> TYPE: PRT
<213> ORGANISM: Artificial Sequence
<220> FEATURE:
<223> OTHER INFORMATION: peptide linker 9

<400> SEQUENCE: 79

Gly Gly Ser Gly Asn Gly Ser Gly
1               5

<210> SEQ ID NO 80
<211> LENGTH: 8
<212> TYPE: PRT
<213> ORGANISM: Artificial Sequence
<220> FEATURE:
<223> OTHER INFORMATION: peptide linker 10

<400> SEQUENCE: 80

Gly Gly Asn Gly Ser Gly Ser Gly
1               5

<210> SEQ ID NO 81
<211> LENGTH: 6
<212> TYPE: PRT
<213> ORGANISM: Artificial Sequence
<220> FEATURE:
<223> OTHER INFORMATION: peptide linker 11

<400> SEQUENCE: 81

Gly Gly Asn Gly Ser Gly
1               5

<210> SEQ ID NO 82
<211> LENGTH: 451
<212> TYPE: PRT
<213> ORGANISM: Artificial Sequence
<220> FEATURE:
<223> OTHER INFORMATION: anti-CEACAM5 Fc hole chain

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 83
<211> LENGTH: 218
<212> TYPE: PRT
<213> ORGANISM: Artificial Sequence
<220> FEATURE:
<223> OTHER INFORMATION: anti-CEACAM5 light chain

<400> SEQUENCE: 83

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80
```

-continued

```
Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 84
<211> LENGTH: 215
<212> TYPE: PRT
<213> ORGANISM: Artificial Sequence
<220> FEATURE:
<223> OTHER INFORMATION: DP47 light chain

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 85
<211> LENGTH: 297
<212> TYPE: PRT
<213> ORGANISM: Homo sapiens

<400> SEQUENCE: 85

Met Thr Thr Pro Arg Asn Ser Val Asn Gly Thr Phe Pro Ala Glu Pro
1               5                   10                  15

Met Lys Gly Pro Ile Ala Met Gln Ser Gly Lys Pro Leu Phe Arg
            20                  25                  30

Arg Met Ser Ser Leu Val Gly Pro Thr Gln Ser Phe Phe Met Arg Glu
            35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Ile Met Tyr Ile Ile
                85                  90                  95

Ser Gly Ser Leu Leu Ala Ala Thr Glu Lys Asn Ser Arg Lys Cys Leu
                100                 105                 110

Val Lys Gly Lys Met Ile Met Asn Ser Leu Ser Leu Phe Ala Ala Ile
            115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 86
<211> LENGTH: 766
<212> TYPE: PRT
<213> ORGANISM: Artificial Sequence
<220> FEATURE:
<223> OTHER INFORMATION: di-mu4-1BBL-CL Fc knob chain

<400> SEQUENCE: 86

Arg Thr Glu Pro Arg Pro Ala Leu Thr Ile Thr Thr Ser Pro Asn Leu
1               5                   10                  15

Gly Thr Arg Glu Asn Asn Ala Asp Gln Val Thr Pro Val Ser His Ile

```
                 20                  25                  30
Gly Cys Pro Asn Thr Thr Gln Gln Gly Ser Pro Val Phe Ala Lys Leu
             35                  40                  45

Leu Ala Lys Asn Gln Ala Ser Leu Ser Asn Thr Thr Leu Asn Trp His
         50                  55                  60

Ser Gln Asp Gly Ala Gly Ser Ser Tyr Leu Ser Gln Gly Leu Arg Tyr
 65                  70                  75                  80

Glu Glu Asp Lys Lys Glu Leu Val Val Asp Ser Pro Gly Leu Tyr Tyr
                 85                  90                  95

Val Phe Leu Glu Leu Lys Leu Ser Pro Thr Phe Thr Asn Thr Gly His
             100                 105                 110

Lys Val Gln Gly Trp Val Ser Leu Val Leu Gln Ala Lys Pro Gln Val
             115                 120                 125

Asp Asp Phe Asp Asn Leu Ala Leu Thr Val Glu Leu Phe Pro Cys Ser
             130                 135                 140

Met Glu Asn Lys Leu Val Asp Arg Ser Trp Ser Gln Leu Leu Leu Leu
145                 150                 155                 160

Lys Ala Gly His Arg Leu Ser Val Gly Leu Arg Ala Tyr Leu His Gly
                 165                 170                 175

Ala Gln Asp Ala Tyr Arg Asp Trp Glu Leu Ser Tyr Pro Asn Thr Thr
             180                 185                 190

Ser Phe Gly Leu Phe Leu Val Lys Pro Asp Asn Pro Trp Glu Gly Gly
             195                 200                 205

Gly Gly Ser Gly Gly Gly Ser Arg Thr Glu Pro Arg Pro Ala Leu
             210                 215                 220

Thr Ile Thr Thr Ser Pro Asn Leu Gly Thr Arg Glu Asn Asn Ala Asp
225                 230                 235                 240

Gln Val Thr Pro Val Ser His Ile Gly Cys Pro Asn Thr Thr Gln Gln
                 245                 250                 255

Gly Ser Pro Val Phe Ala Lys Leu Leu Ala Lys Asn Gln Ala Ser Leu
             260                 265                 270

Ser Asn Thr Thr Leu Asn Trp His Ser Gln Asp Gly Ala Gly Ser Ser
             275                 280                 285

Tyr Leu Ser Gln Gly Leu Arg Tyr Glu Glu Asp Lys Lys Glu Leu Val
             290                 295                 300

Val Asp Ser Pro Gly Leu Tyr Tyr Val Phe Leu Glu Leu Lys Leu Ser
305                 310                 315                 320

Pro Thr Phe Thr Asn Thr Gly His Lys Val Gln Gly Trp Val Ser Leu
                 325                 330                 335

Val Leu Gln Ala Lys Pro Gln Val Asp Asp Phe Asp Asn Leu Ala Leu
             340                 345                 350

Thr Val Glu Leu Phe Pro Cys Ser Met Glu Asn Lys Leu Val Asp Arg
             355                 360                 365

Ser Trp Ser Gln Leu Leu Leu Leu Lys Ala Gly His Arg Leu Ser Val
             370                 375                 380

Gly Leu Arg Ala Tyr Leu His Gly Ala Gln Asp Ala Tyr Arg Asp Trp
385                 390                 395                 400

Glu Leu Ser Tyr Pro Asn Thr Thr Ser Phe Gly Leu Phe Leu Val Lys
                 405                 410                 415

Pro Asp Asn Pro Trp Glu Gly Gly Gly Ser Gly Gly Gly Ser
             420                 425                 430

Arg Thr Val Ala Ala Pro Ser Val Phe Ile Phe Pro Pro Ser Asp Arg
             435                 440                 445
```

```
Lys Leu Lys Ser Gly Thr Ala Ser Val Val Cys Leu Leu Asn Asn Phe
            450                 455                 460

Tyr Pro Arg Glu Ala Lys Val Gln Trp Lys Val Asp Asn Ala Leu Gln
465                 470                 475                 480

Ser Gly Asn Ser Gln Glu Ser Val Thr Glu Gln Asp Ser Lys Asp Ser
                485                 490                 495

Thr Tyr Ser Leu Ser Ser Thr Leu Thr Leu Ser Lys Ala Asp Tyr Glu
                500                 505                 510

Lys His Lys Val Tyr Ala Cys Glu Val Thr His Gln Gly Leu Ser Ser
            515                 520                 525

Pro Val Thr Lys Ser Phe Asn Arg Gly Glu Cys Asp Lys Thr His Thr
            530                 535                 540

Cys Pro Pro Cys Pro Ala Pro Glu Ala Ala Gly Gly Pro Ser Val Phe
545                 550                 555                 560

Leu Phe Pro Pro Lys Pro Lys Asp Thr Leu Met Ile Ser Arg Thr Pro
                565                 570                 575

Glu Val Thr Cys Val Val Val Asp Val Ser His Glu Asp Pro Glu Val
                580                 585                 590

Lys Phe Asn Trp Tyr Val Asp Gly Val Glu Val His Asn Ala Lys Thr
            595                 600                 605

Lys Pro Arg Glu Glu Gln Tyr Asn Ser Thr Tyr Arg Val Val Ser Val
            610                 615                 620

Leu Thr Val Leu His Gln Asp Trp Leu Asn Gly Lys Glu Tyr Lys Cys
625                 630                 635                 640

Lys Val Ser Asn Lys Ala Leu Gly Ala Pro Ile Glu Lys Thr Ile Ser
                645                 650                 655

Lys Ala Lys Gly Gln Pro Arg Glu Pro Gln Val Tyr Thr Leu Pro Pro
            660                 665                 670

Cys Arg Asp Glu Leu Thr Lys Asn Gln Val Ser Leu Trp Cys Leu Val
            675                 680                 685

Lys Gly Phe Tyr Pro Ser Asp Ile Ala Val Glu Trp Glu Ser Asn Gly
            690                 695                 700

Gln Pro Glu Asn Asn Tyr Lys Thr Thr Pro Pro Val Leu Asp Ser Asp
705                 710                 715                 720

Gly Ser Phe Phe Leu Tyr Ser Lys Leu Thr Val Asp Lys Ser Arg Trp
                725                 730                 735

Gln Gln Gly Asn Val Phe Ser Cys Ser Val Met His Glu Ala Leu His
                740                 745                 750

Asn His Tyr Thr Gln Lys Ser Leu Ser Leu Ser Pro Gly Lys
            755                 760                 765

<210> SEQ ID NO 87
<211> LENGTH: 319
<212> TYPE: PRT
<213> ORGANISM: Artificial Sequence
<220> FEATURE:
<223> OTHER INFORMATION: mono-mu4-1BBL-CH1 chain

<400> SEQUENCE: 87

Arg Thr Glu Pro Arg Pro Ala Leu Thr Ile Thr Thr Ser Pro Asn Leu
1               5                   10                  15

Gly Thr Arg Glu Asn Asn Ala Asp Gln Val Thr Pro Val Ser His Ile
                20                  25                  30

Gly Cys Pro Asn Thr Thr Gln Gln Gly Ser Pro Val Phe Ala Lys Leu
            35                  40                  45
```

```
Leu Ala Lys Asn Gln Ala Ser Leu Ser Asn Thr Thr Leu Asn Trp His
     50                  55                  60

Ser Gln Asp Gly Ala Gly Ser Ser Tyr Leu Ser Gln Gly Leu Arg Tyr
 65                  70                  75                  80

Glu Glu Asp Lys Lys Glu Leu Val Val Asp Ser Pro Gly Leu Tyr Tyr
                 85                  90                  95

Val Phe Leu Glu Leu Lys Leu Ser Pro Thr Phe Thr Asn Thr Gly His
            100                 105                 110

Lys Val Gln Gly Trp Val Ser Leu Val Leu Gln Ala Lys Pro Gln Val
        115                 120                 125

Asp Asp Phe Asp Asn Leu Ala Leu Thr Val Glu Leu Phe Pro Cys Ser
130                 135                 140

Met Glu Asn Lys Leu Val Asp Arg Ser Trp Ser Gln Leu Leu Leu Leu
145                 150                 155                 160

Lys Ala Gly His Arg Leu Ser Val Gly Leu Arg Ala Tyr Leu His Gly
                165                 170                 175

Ala Gln Asp Ala Tyr Arg Asp Trp Glu Leu Ser Tyr Pro Asn Thr Thr
            180                 185                 190

Ser Phe Gly Leu Phe Leu Val Lys Pro Asp Asn Pro Trp Glu Gly Gly
        195                 200                 205

Gly Gly Ser Gly Gly Gly Gly Ser Ala Ser Thr Lys Gly Pro Ser Val
    210                 215                 220

Phe Pro Leu Ala Pro Ser Ser Lys Ser Thr Ser Gly Gly Thr Ala Ala
225                 230                 235                 240

Leu Gly Cys Leu Val Glu Asp Tyr Phe Pro Glu Pro Val Thr Val Ser
                245                 250                 255

Trp Asn Ser Gly Ala Leu Thr Ser Gly Val His Thr Phe Pro Ala Val
            260                 265                 270

Leu Gln Ser Ser Gly Leu Tyr Ser Leu Ser Ser Val Val Thr Val Pro
        275                 280                 285

Ser Ser Ser Leu Gly Thr Gln Thr Tyr Ile Cys Asn Val Asn His Lys
    290                 295                 300

Pro Ser Asn Thr Lys Val Asp Glu Lys Val Glu Pro Lys Ser Cys
305                 310                 315

<210> SEQ ID NO 88
<211> LENGTH: 447
<212> TYPE: PRT
<213> ORGANISM: Artificial Sequence
<220> FEATURE:
<223> OTHER INFORMATION: VHCH1 (4B9) Fc hole chain

<400> SEQUENCE: 88

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ile Gly Ser Gly Ala Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

```
Ala Lys Gly Trp Phe Gly Gly Phe Asn Tyr Trp Gln Gly Thr Leu
            100                 105                 110
Val Thr Val Ser Ser Ala Ser Thr Lys Gly Pro Ser Val Phe Pro Leu
    115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Ala Ala Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Gly Ala Pro Ile Glu Lys Thr Ile
                325                 330                 335
Ser Lys Ala Lys Gly Gln Pro Arg Glu Pro Gln Val Cys Thr Leu Pro
            340                 345                 350
Pro Ser Arg Asp Glu Leu Thr Lys Asn Gln Val Ser Leu Ser Cys Ala
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Val Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 89
<211> LENGTH: 215
<212> TYPE: PRT
<213> ORGANISM: Artificial Sequence
<220> FEATURE:
<223> OTHER INFORMATION: VLCL(4B9) Light chain

<400> SEQUENCE: 89

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
                35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 90
<211> LENGTH: 571
<212> TYPE: PRT
<213> ORGANISM: Artificial Sequence
<220> FEATURE:
<223> OTHER INFORMATION: VHCH1 (MU137-1)-Heavy chain Fc-DD-VL (28H1)

<400> SEQUENCE: 90

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Ile Phe Ser Tyr Phe
            20                  25                  30

Asp Met Ala Trp Val Arg Gln Ala Pro Thr Lys Gly Leu Glu Trp Val
                35                  40                  45

Ala Ser Ile Ser Pro Ser Gly Asp Ile Pro Tyr Tyr Arg Asp Ser Val
    50                  55                  60

Lys Gly Arg Phe Thr Val Ser Arg Glu Asn Ala Lys Ser Ser Leu Tyr
65                  70                  75                  80

Leu Gln Met Asp Ser Leu Arg Ser Glu Asp Thr Ala Thr Tyr Tyr Cys
                85                  90                  95

Ala Arg Arg Ser Tyr Gly Gly Tyr Ser Glu Leu Asp Tyr Trp Gly Gln
                100                 105                 110

Gly Val Met Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

-continued

```
Trp Asn Ser Gly Ser Leu Ser Ser Gly Val His Thr Phe Pro Ala Val
            165                 170                 175

Leu Gln Ser Asp Leu Tyr Thr Leu Ser Ser Val Thr Val Pro Ser
            180                 185                 190

Ser Thr Trp Pro Ser Gln Thr Val Thr Cys Asn Val Ala His Pro Ala
            195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Ala Ile Ser Lys Asp Asp Pro Glu Val Gln Phe
                    260                 265                 270

Ser Trp Phe Val Asp Asp Val Glu Val His Thr Ala Gln Thr Lys Pro
            275                 280                 285

Arg Glu Glu Gln Ile Asn Ser Thr Phe Arg Ser Val Ser Glu Leu Pro
            290                 295                 300

Ile Met His Gln Asp Trp Leu Asn Gly Lys Glu Phe Lys Cys Arg Val
305                 310                 315                 320

Asn Ser Ala Ala Phe Gly Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asn
            355                 360                 365

Phe Phe Pro Glu Asp Ile Thr Val Glu Trp Gln Trp Asn Gly Gln Pro
            370                 375                 380

Ala Glu Asn Tyr Asp Asn Thr Gln Pro Ile Met Asp Thr Asp Gly Ser
385                 390                 395                 400

Tyr Phe Val Tyr Ser Asp Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Gly Gly Gly Ser
            435                 440                 445

Gly Gly Gly Gly Ser Gly Gly Gly Ser Gly Gly Gly Ser Glu
    450                 455                 460

Ile Val Leu Thr Gln Ser Pro Gly Thr Leu Ser Leu Ser Pro Gly Glu
465                 470                 475                 480

Arg Ala Thr Leu Ser Cys Arg Ala Ser Gln Ser Val Ser Arg Ser Tyr
                485                 490                 495

Leu Ala Trp Tyr Gln Gln Lys Pro Gly Gln Ala Pro Arg Leu Leu Ile
            500                 505                 510

Ile Gly Ala Ser Thr Arg Ala Thr Gly Ile Pro Asp Arg Phe Ser Gly
            515                 520                 525

Ser Gly Ser Gly Thr Asp Phe Thr Leu Thr Ile Ser Arg Leu Glu Pro
    530                 535                 540

Glu Asp Phe Ala Val Tyr Tyr Cys Gln Gln Gly Gln Val Ile Pro Pro
545                 550                 555                 560

Thr Phe Gly Gln Gly Thr Lys Val Glu Ile Lys
                565                 570
```

<210> SEQ ID NO 91
<211> LENGTH: 579
<212> TYPE: PRT
<213> ORGANISM: Artificial Sequence
<220> FEATURE:
<223> OTHER INFORMATION: VHCH1 (20H4.9)-Heavy chain Fc-KK-VH (28H1)

<400> SEQUENCE: 91

```
Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Ile Phe Ser Tyr Phe
            20                  25                  30

Asp Met Ala Trp Val Arg Gln Ala Pro Thr Lys Gly Leu Glu Trp Val
        35                  40                  45

Ala Ser Ile Ser Pro Ser Gly Asp Ile Pro Tyr Tyr Arg Asp Ser Val
    50                  55                  60

Lys Gly Arg Phe Thr Val Ser Arg Glu Asn Ala Lys Ser Ser Leu Tyr
65                  70                  75                  80

Leu Gln Met Asp Ser Leu Arg Ser Glu Asp Thr Ala Thr Tyr Tyr Cys
                85                  90                  95

Ala Arg Arg Ser Tyr Gly Gly Tyr Ser Glu Leu Asp Tyr Trp Gly Gln
            100                 105                 110

Gly Val Met Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Ala Ile Ser Lys Asp Asp Pro Glu Val Gln Phe
            260                 265                 270

Ser Trp Phe Val Asp Asp Val Glu Val His Thr Ala Gln Thr Lys Pro
        275                 280                 285

Arg Glu Glu Gln Ile Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Gly Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Lys Gln Met Ala Lys Asp Lys Val Ser Leu Thr Cys Met Ile Thr Asn
        355                 360                 365
```

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Lys Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Gly Gly Gly Ser
                435                 440                 445

Gly Gly Gly Gly Ser Gly Gly Gly Ser Gly Gly Gly Ser Glu
450                 455                 460

Val Gln Leu Leu Glu Ser Gly Gly Leu Val Gln Pro Gly Gly Ser
465                 470                 475                 480

Leu Arg Leu Ser Cys Ala Ala Ser Gly Phe Thr Phe Ser Ser His Ala
                485                 490                 495

Met Ser Trp Val Arg Gln Ala Pro Gly Lys Gly Leu Glu Trp Val Ser
                500                 505                 510

Ala Ile Trp Ala Ser Gly Glu Gln Tyr Tyr Ala Asp Ser Val Lys Gly
                515                 520                 525

Arg Phe Thr Ile Ser Arg Asp Asn Ser Lys Asn Thr Leu Tyr Leu Gln
                530                 535                 540

Met Asn Ser Leu Arg Ala Glu Asp Thr Ala Val Tyr Tyr Cys Ala Lys
545                 550                 555                 560

Gly Trp Leu Gly Asn Phe Asp Tyr Trp Gly Gln Gly Thr Leu Val Thr
                565                 570                 575

Val Ser Ser

<210> SEQ ID NO 92
<211> LENGTH: 214
<212> TYPE: PRT
<213> ORGANISM: Artificial Sequence
<220> FEATURE:
<223> OTHER INFORMATION: VLCL-Light chain (MU137-1)

<400> SEQUENCE: 92

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
                20                  25                  30

Leu Ala Trp Tyr His Gln Lys Pro Gly Lys Ser Pro Gln Leu Leu Ile
                35                  40                  45

Tyr Gly Thr Ser Ser Leu Ala Asp Gly Val Pro Ser Arg Phe Ser Gly
            50                  55                  60

Ser Ser Ser Gly Ser Gln Tyr Ser Leu Lys Ile Ser Arg Leu Gln Val
65                  70                  75                  80

Glu Asp Ile Gly Ile Tyr Tyr Cys Leu Gln Ala Tyr Gly Ala Pro Trp
                85                  90                  95

Thr Phe Gly Gly Gly Thr Lys Leu Glu Leu Lys Arg Ala Asp Ala Ala
                100                 105                 110

Pro Thr Val Ser Ile Phe Pro Pro Ser Ser Glu Gln Leu Thr Ser Gly
                115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu

```
                 145                 150                 155                 160
Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 93
<211> LENGTH: 579
<212> TYPE: PRT
<213> ORGANISM: Artificial Sequence
<220> FEATURE:
<223> OTHER INFORMATION: VHCH1 (MU137-1)-Heavy chain Fc-DD-VH (28H1)

<400> SEQUENCE: 93

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Ile Phe Ser Tyr Phe
            20                  25                  30

Asp Met Ala Trp Val Arg Gln Ala Pro Thr Lys Gly Leu Glu Trp Val
        35                  40                  45

Ala Ser Ile Ser Pro Ser Gly Asp Ile Pro Tyr Tyr Arg Asp Ser Val
    50                  55                  60

Lys Gly Arg Phe Thr Val Ser Arg Glu Asn Ala Lys Ser Ser Leu Tyr
65                  70                  75                  80

Leu Gln Met Asp Ser Leu Arg Ser Glu Asp Thr Ala Thr Tyr Tyr Cys
                85                  90                  95

Ala Arg Arg Ser Tyr Gly Gly Tyr Ser Glu Leu Asp Tyr Trp Gly Gln
            100                 105                 110

Gly Val Met Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Ala Ile Ser Lys Asp Asp Pro Glu Val Gln Phe
            260                 265                 270

Ser Trp Phe Val Asp Asp Val Glu Val His Thr Ala Gln Thr Lys Pro
        275                 280                 285

Arg Glu Glu Gln Ile Asn Ser Thr Phe Arg Ser Val Ser Glu Leu Pro
```

```
                290                 295                 300
Ile Met His Gln Asp Trp Leu Asn Gly Lys Glu Phe Lys Cys Arg Val
305                 310                 315                 320

Asn Ser Ala Ala Phe Gly Ala Pro Ile Glu Lys Thr Ile Ser Lys Thr
                325                 330                 335

Lys Gly Arg Pro Lys Ala Pro Gln Val Tyr Thr Ile Pro Pro Pro Lys
                340                 345                 350

Glu Gln Met Ala Lys Asp Lys Val Ser Leu Thr Cys Met Ile Thr Asn
                355                 360                 365

Phe Phe Pro Glu Asp Ile Thr Val Glu Trp Gln Trp Asn Gly Gln Pro
370                 375                 380

Ala Glu Asn Tyr Asp Asn Thr Gln Pro Ile Met Asp Thr Asp Gly Ser
385                 390                 395                 400

Tyr Phe Val Tyr Ser Asp Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Gly Gly Gly Gly Ser
                435                 440                 445

Gly Gly Gly Gly Ser Gly Gly Gly Ser Gly Gly Gly Gly Ser Glu
                450                 455                 460

Val Gln Leu Leu Glu Ser Gly Gly Gly Leu Val Gln Pro Gly Gly Ser
465                 470                 475                 480

Leu Arg Leu Ser Cys Ala Ala Ser Gly Phe Thr Phe Ser Ser His Ala
                485                 490                 495

Met Ser Trp Val Arg Gln Ala Pro Gly Lys Gly Leu Glu Trp Val Ser
                500                 505                 510

Ala Ile Trp Ala Ser Gly Glu Gln Tyr Tyr Ala Asp Ser Val Lys Gly
                515                 520                 525

Arg Phe Thr Ile Ser Arg Asp Asn Ser Lys Asn Thr Leu Tyr Leu Gln
                530                 535                 540

Met Asn Ser Leu Arg Ala Glu Asp Thr Ala Val Tyr Tyr Cys Ala Lys
545                 550                 555                 560

Gly Trp Leu Gly Asn Phe Asp Tyr Trp Gly Gln Gly Thr Leu Val Thr
                565                 570                 575

Val Ser Ser

<210> SEQ ID NO 94
<211> LENGTH: 571
<212> TYPE: PRT
<213> ORGANISM: Artificial Sequence
<220> FEATURE:
<223> OTHER INFORMATION: VHCH1 (MU137-1)-Heavy chain Fc-KK-VL (28H1)

<400> SEQUENCE: 94

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Ile Phe Ser Tyr Phe
                20                  25                  30

Asp Met Ala Trp Val Arg Gln Ala Pro Thr Lys Gly Leu Glu Trp Val
                35                  40                  45

Ala Ser Ile Ser Pro Ser Gly Asp Ile Pro Tyr Tyr Arg Asp Ser Val
                50                  55                  60

Lys Gly Arg Phe Thr Val Ser Arg Glu Asn Ala Lys Ser Ser Leu Tyr
65                  70                  75                  80
```

```
Leu Gln Met Asp Ser Leu Arg Ser Glu Asp Thr Ala Thr Tyr Tyr Cys
                85                  90                  95

Ala Arg Arg Ser Tyr Gly Gly Tyr Ser Glu Leu Asp Tyr Trp Gly Gln
            100                 105                 110

Gly Val Met Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asp Cys Gly Cys
210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Ala Ile Ser Lys Asp Asp Pro Glu Val Gln Phe
            260                 265                 270

Ser Trp Phe Val Asp Asp Val Glu Val His Thr Ala Gln Thr Lys Pro
        275                 280                 285

Arg Glu Glu Gln Ile Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Gly Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Lys Gln Met Ala Lys Asp Lys Val Ser Leu Thr Cys Met Ile Thr Asn
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Lys Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Gly Gly Gly Gly Ser
            435                 440                 445

Gly Gly Gly Gly Ser Gly Gly Gly Ser Gly Gly Gly Ser Glu
450                 455                 460

Ile Val Leu Thr Gln Ser Pro Gly Thr Leu Ser Leu Ser Pro Gly Glu
465                 470                 475                 480

Arg Ala Thr Leu Ser Cys Arg Ala Ser Gln Ser Val Ser Arg Ser Tyr
                485                 490                 495
```

```
Leu Ala Trp Tyr Gln Gln Lys Pro Gly Gln Ala Pro Arg Leu Leu Ile
            500                 505                 510

Ile Gly Ala Ser Thr Arg Ala Thr Gly Ile Pro Asp Arg Phe Ser Gly
            515                 520                 525

Ser Gly Ser Gly Thr Asp Phe Thr Leu Thr Ile Ser Arg Leu Glu Pro
            530                 535                 540

Glu Asp Phe Ala Val Tyr Tyr Cys Gln Gln Gly Gln Val Ile Pro Pro
545                 550                 555                 560

Thr Phe Gly Gln Gly Thr Lys Val Glu Ile Lys
            565                 570

<210> SEQ ID NO 95
<211> LENGTH: 1245
<212> TYPE: PRT
<213> ORGANISM: Homo sapiens

<400> SEQUENCE: 95

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300
```

```
Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
        340                 345                 350

Val Arg Ala Val Thr Ser Ala Asn Ile Gln Glu Phe Ala Gly Cys Lys
    355                 360                 365

Lys Ile Phe Gly Ser Leu Ala Phe Leu Pro Glu Ser Phe Asp Gly Asp
370                 375                 380

Pro Ala Ser Asn Thr Ala Glu Thr Leu Glu Glu Ile Thr Gly Tyr Leu
385                 390                 395                 400

Tyr Ile Ser Ala Trp Pro Asp Ser Leu Pro Asp Leu Ser Val Phe Gln
                405                 410                 415

Asn Leu Gln Val Ile Arg Gly Arg Ile Leu His Asn Gly Ala Tyr Ser
            420                 425                 430

Leu Thr Leu Gln Gly Leu Gly Ile Ser Trp Leu Gly Leu Arg Ser Leu
        435                 440                 445

Arg Glu Leu Gly Ser Gly Leu Ala Leu Ile His His Asn Thr His Leu
    450                 455                 460

Cys Phe Val His Thr Val Pro Trp Asp Gln Leu Phe Arg Asn Pro His
465                 470                 475                 480

Gln Ala Leu Leu His Thr Ala Asn Arg Pro Glu Asp Glu Cys Val Gly
                485                 490                 495

Glu Gly Leu Ala Cys His Gln Leu Cys Ala Arg Gly His Cys Trp Gly
            500                 505                 510

Pro Gly Pro Thr Gln Cys Val Asn Cys Ser Gln Phe Leu Arg Gly Gln
        515                 520                 525

Glu Cys Val Glu Glu Cys Arg Val Leu Gln Gly Leu Pro Arg Glu Tyr
    530                 535                 540

Val Asn Ala Arg His Cys Leu Pro Cys His Pro Glu Cys Gln Pro Gln
545                 550                 555                 560

Asn Gly Ser Val Thr Cys Phe Gly Pro Glu Ala Asp Gln Cys Val Ala
                565                 570                 575

Cys Ala His Tyr Lys Asp Pro Pro Phe Cys Val Ala Arg Cys Pro Ser
            580                 585                 590

Gly Val Lys Pro Asp Leu Ser Tyr Met Pro Ile Trp Lys Phe Pro Asp
        595                 600                 605

Glu Glu Gly Ala Cys Gln Pro Cys Pro Ile Asn Cys Thr His Ser Cys
    610                 615                 620

Val Asp Leu Asp Asp Lys Gly Cys Pro Ala Glu Gln Arg Ala Ser Pro
625                 630                 635                 640

Leu Thr Ser Ile Ile Ser Ala Val Val Gly Ile Leu Leu Val Val Val
                645                 650                 655

Leu Gly Val Val Phe Gly Ile Leu Ile Lys Arg Arg Gln Gln Lys Ile
            660                 665                 670

Arg Lys Tyr Thr Met Arg Arg Leu Leu Gln Glu Thr Glu Leu Val Glu
        675                 680                 685

Pro Leu Thr Pro Ser Gly Ala Met Pro Asn Gln Ala Gln Met Arg Ile
    690                 695                 700

Leu Lys Glu Thr Glu Leu Arg Lys Val Lys Val Leu Gly Ser Gly Ala
705                 710                 715                 720
```

-continued

```
Phe Gly Thr Val Tyr Lys Gly Ile Trp Ile Pro Asp Gly Glu Asn Val
                725                 730                 735

Lys Ile Pro Val Ala Ile Lys Val Leu Arg Glu Asn Thr Ser Pro Lys
            740                 745                 750

Ala Asn Lys Glu Ile Leu Asp Glu Ala Tyr Val Met Ala Gly Val Gly
        755                 760                 765

Ser Pro Tyr Val Ser Arg Leu Leu Gly Ile Cys Leu Thr Ser Thr Val
    770                 775                 780

Gln Leu Val Thr Gln Leu Met Pro Tyr Gly Cys Leu Leu Asp His Val
785                 790                 795                 800

Arg Glu Asn Arg Gly Arg Leu Gly Ser Gln Asp Leu Leu Asn Trp Cys
                805                 810                 815

Met Gln Ile Ala Lys Gly Met Ser Tyr Leu Glu Asp Val Arg Leu Val
            820                 825                 830

His Arg Asp Leu Ala Ala Arg Asn Val Leu Val Lys Ser Pro Asn His
        835                 840                 845

Val Lys Ile Thr Asp Phe Gly Leu Ala Arg Leu Leu Asp Ile Asp Glu
    850                 855                 860

Thr Glu Tyr His Ala Asp Gly Gly Lys Val Pro Ile Lys Trp Met Ala
865                 870                 875                 880

Leu Glu Ser Ile Leu Arg Arg Arg Phe Thr His Gln Ser Asp Val Trp
                885                 890                 895

Ser Tyr Gly Val Thr Val Trp Glu Leu Met Thr Phe Gly Ala Lys Pro
            900                 905                 910

Tyr Asp Gly Ile Pro Ala Arg Glu Ile Pro Asp Leu Leu Glu Lys Gly
        915                 920                 925

Glu Arg Leu Pro Gln Pro Pro Ile Cys Thr Ile Asp Val Tyr Met Ile
    930                 935                 940

Met Val Lys Cys Trp Met Ile Asp Ser Glu Cys Arg Pro Arg Phe Arg
945                 950                 955                 960

Glu Leu Val Ser Glu Phe Ser Arg Met Ala Arg Asp Pro Gln Arg Phe
                965                 970                 975

Val Val Ile Gln Asn Glu Asp Leu Gly Pro Ala Ser Pro Leu Asp Ser
            980                 985                 990

Thr Phe Tyr Arg Ser Leu Leu Glu Asp Asp Asp Met Gly Asp Leu Val
        995                 1000                1005

Asp Ala Glu Glu Tyr Leu Val Pro Gln Gln Gly Phe Phe Cys Pro
    1010                1015                1020

Asp Pro Ala Pro Gly Ala Gly Gly Met Val His His Arg His Arg
    1025                1030                1035

Ser Ser Ser Thr Arg Ser Gly Gly Gly Asp Leu Thr Leu Gly Leu
    1040                1045                1050

Glu Pro Ser Glu Glu Glu Ala Pro Arg Ser Pro Leu Ala Pro Ser
    1055                1060                1065

Glu Gly Ala Gly Ser Asp Val Phe Asp Gly Asp Leu Gly Met Gly
    1070                1075                1080

Ala Ala Lys Gly Leu Gln Ser Leu Pro Thr His Asp Pro Ser Pro
    1085                1090                1095

Leu Gln Arg Tyr Ser Glu Asp Pro Thr Val Pro Leu Pro Ser Glu
    1100                1105                1110

Thr Asp Gly Tyr Val Ala Pro Leu Thr Cys Ser Pro Gln Pro Glu
    1115                1120                1125

Tyr Val Asn Gln Pro Asp Val Arg Pro Gln Pro Pro Ser Pro Arg
```

```
                      1130              1135              1140

Glu  Gly  Pro  Leu  Pro  Ala  Ala  Arg  Pro  Ala  Gly  Ala  Thr  Leu  Glu
          1145                    1150                    1155

Arg  Pro  Lys  Thr  Leu  Ser  Pro  Gly  Lys  Asn  Gly  Val  Val  Lys  Asp
     1160                    1165                    1170

Val  Phe  Ala  Phe  Gly  Gly  Ala  Val  Glu  Asn  Pro  Glu  Tyr  Leu  Thr
1175                     1180                    1185

Pro  Gln  Gly  Gly  Ala  Ala  Pro  Gln  Pro  His  Pro  Pro  Pro  Ala  Phe
     1190                    1195                    1200

Ser  Pro  Ala  Phe  Asp  Asn  Leu  Tyr  Tyr  Trp  Asp  Gln  Asp  Pro  Pro
1205                     1210                    1215

Glu  Arg  Gly  Ala  Pro  Pro  Ser  Thr  Phe  Lys  Gly  Thr  Pro  Thr  Ala
     1220                    1225                    1230

Glu  Asn  Pro  Glu  Tyr  Leu  Gly  Leu  Asp  Val  Pro  Val
     1235                    1240                    1245

<210> SEQ ID NO 96
<211> LENGTH: 120
<212> TYPE: PRT
<213> ORGANISM: Artificial Sequence
<220> FEATURE:
<223> OTHER INFORMATION: VH trastuzumab

<400> SEQUENCE: 96

Glu  Val  Gln  Leu  Val  Glu  Ser  Gly  Gly  Gly  Leu  Val  Gln  Pro  Gly  Gly
1                   5                   10                  15

Ser  Leu  Arg  Leu  Ser  Cys  Ala  Ala  Ser  Gly  Phe  Asn  Ile  Lys  Asp  Thr
            20                  25                  30

Tyr  Ile  His  Trp  Val  Arg  Gln  Ala  Pro  Gly  Lys  Gly  Leu  Glu  Trp  Val
        35                  40                  45

Ala  Arg  Ile  Tyr  Pro  Thr  Asn  Gly  Tyr  Thr  Arg  Tyr  Ala  Asp  Ser  Val
    50                  55                  60

Lys  Gly  Arg  Phe  Thr  Ile  Ser  Ala  Asp  Thr  Ser  Lys  Asn  Thr  Ala  Tyr
65                  70                  75                  80

Leu  Gln  Met  Asn  Ser  Leu  Arg  Ala  Glu  Asp  Thr  Ala  Val  Tyr  Tyr  Cys
                85                  90                  95

Ser  Arg  Trp  Gly  Gly  Asp  Gly  Phe  Tyr  Ala  Met  Asp  Tyr  Trp  Gly  Gln
            100                 105                 110

Gly  Thr  Leu  Val  Thr  Val  Ser  Ser
        115                 120

<210> SEQ ID NO 97
<211> LENGTH: 107
<212> TYPE: PRT
<213> ORGANISM: Artificial Sequence
<220> FEATURE:
<223> OTHER INFORMATION: VL trastuzumab

<400> SEQUENCE: 97

Asp  Ile  Gln  Met  Thr  Gln  Ser  Pro  Ser  Ser  Leu  Ser  Ala  Ser  Val  Gly
1                   5                   10                  15

Asp  Arg  Val  Thr  Ile  Thr  Cys  Arg  Ala  Ser  Gln  Asp  Val  Asn  Thr  Ala
            20                  25                  30

Val  Ala  Trp  Tyr  Gln  Gln  Lys  Pro  Gly  Lys  Ala  Pro  Lys  Leu  Leu  Ile
        35                  40                  45

Tyr  Ser  Ala  Ser  Phe  Leu  Tyr  Ser  Gly  Val  Pro  Ser  Arg  Phe  Ser  Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105
```

<210> SEQ ID NO 98
<211> LENGTH: 119
<212> TYPE: PRT
<213> ORGANISM: Artificial Sequence
<220> FEATURE:
<223> OTHER INFORMATION: VH pertuzumab

<400> SEQUENCE: 98

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Thr Met Asp Trp Val Arg Gln Ala Pro Gly Lys Gly Leu Glu Trp Val
         35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 99
<211> LENGTH: 107
<212> TYPE: PRT
<213> ORGANISM: Artificial Sequence
<220> FEATURE:
<223> OTHER INFORMATION: VL pertuzumab

<400> SEQUENCE: 99

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Val Ser Ile Gly
             20                  25                  30

Val Ala Trp Tyr Gln Gln Lys Pro Gly Lys Ala Pro Lys Leu Leu Ile
         35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys
            100                 105
```

COMBINATION THERAPY WITH TARGETED 4-1BB (CD137) AGONISTS

CROSS-REFERENCE TO RELATED APPLICATIONS

This application is a Continuation of International Application No. PCT/EP2019/056067, filed Mar. 12, 2019, which claims priority from EP Application No. 18161340.7 filed Mar. 13, 2018. The contents of each of the foregoing applications are incorporated herein by reference in its entirety.

SEQUENCE LISTING

This application contains a Sequence Listing which has been submitted electronically in ASCII format and is hereby incorporated by reference in its entirety. Said ASCII copy, created on Sep. 8, 2020, is named P34719-US_SeqListing.txt and is 236,004 bytes in size.

FIELD OF THE INVENTION

The present invention relates to combination therapies employing 4-1BB (CD137) agonists, in particular 4-1BBL trimer containing antigen binding molecules, and a HER-2 targeting agent, and the use of these combination therapies for the treatment of cancer and methods of using the combination therapies.

BACKGROUND

Cancer is one of the leading causes of death worldwide. Despite advances in treatment options, prognosis of patients with advanced cancer remains poor. Consequently, there is a persisting and urgent medical need for optimal therapies to increase survival of cancer patients without causing unacceptable toxicity. Recent results from clinical trials have shown that immune therapies can extend the overall survival of cancer patients and lead to durable responses. Despite these promising results, current immune-based therapies are only effective in a proportion of patients and combination strategies are needed to improve therapeutic benefit.

The human epidermal growth factor receptor-2 (HER-2; ErbB2) is a receptor tyrosine kinase and a member of the epidermal growth factor receptor (EGFR) family of transmembrane receptors. HER-2 is overexpressed in a range of tumor types and it has been implicated in disease initiation and progression. It is associated with poor prognosis. For example, overexpression of HER-2 is observed in approximately 30% of human breast cancers and it is implicated in the aggressive growth and poor clinical outcomes associated with these tumors (Slamon et al (1987) Science 235:177-182).

The humanized anti-HER-2 monoclonal antibody trastuzumab (CAS 180288-69-1, HERCEPTIN®, huMAb4D5-8, rhuMAb HER2, Genentech) targets the extracellular domain of HER-2 (U.S. Pat. Nos. 5,677,171; 5,821,337; 6,054,297; 6,165,464; 6,339,142; 6,407,213; 6,639,055; 6,719,971; 6,800,738; 7,074,404; Coussens et al (1985) Science 230:1 132-9; Slamon et al (1989) Science 244:707-12; Slamon et al (2001) New Engl. J. Med. 344: 783-792). Trastuzumab has been shown to inhibit the proliferation of human tumor cells that overexpress HER-2 and is a mediator of antibody-dependent cellular cytotoxicity, ADCC (Hudziak et al (1989) Mol Cell Biol 9:1 165-72; Lewis et al (1993) Cancer Immunol Immunother; 37:255-63; Baselga et al (1998) Cancer Res. 58:2825-2831; Hotaling et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137).

HERCEPTIN® (trastuzumab, Genentech Inc.) was approved in 1998 for the treatment of of patients with HER2-overexpressing metastatic breast cancers (Baselga et al, (1996) J. Clin. Oncol. 14:737-744). In 2006, the FDA approved HERCEPTIN® as part of a treatment regimen containing doxorubicin, cyclophosphamide and paclitaxel for the adjuvant treatment of patients with HER2-positive, node-positive breast cancer.

Trastuzumab-MCC-DM1 (T-DM1, trastuzumab emtansine, ado-trastuzumab emtansine, KADCYLA®), a novel antibody-drug conjugate (ADC) for the treatment of HER2-positive breast cancer, is composed of the cytotoxic agent DM1 (a thiol-containing maytansinoid anti-microtubule agent) conjugated to trastuzumab at lysine side chains via an MCC linker, with an average drug load (drug to antibody ratio) of about 3.5. After binding to HER2 expressed on tumor cells, T-DM1 undergoes receptor-mediated internalization, resulting in intracellular release of cytotoxic catabolites containing DM1 and subsequent cell death. The FDA approved ado-trastuzumab emtansine, marketed under the tradename KADCYLA®, in 2013 for the treatment of patients with HER2-positive, metastatic breast cancer who previously received treatment with trastuzumab and a taxane.

Pertuzumab (also known as recombinant humanized monoclonal antibody 2C4, rhuMAb 2C4, PERJETA®, Genentech, Inc, South San Francisco) is another antibody treatment targeting HER-2. Pertuzumab is a HER dimerization inhibitor (HDI) and functions to inhibit the ability of HER2 to form active heterodimers or homodimers with other HER receptors (such as EGFR/HER1, HER2, HER3 and HER4). See, for example, Harari and Yarden Oncogene 19:6102-14 (2000); Yarden and Sliwkowski. Nat Rev Mol Cell Biol 2:127-37 (2001); Sliwkowski Nat Struct Biol 10:158-9 (2003); Cho et al. Nature 421:756-60 (2003); and Malik et al. Pro Am Soc Cancer Res 44:176-7 (2003); U.S. Pat. No. 7,560,111. PERJETA®, was first approved in 2012 in combination with trastuzumab and docetaxel for the treatment of patients with advanced or late-stage (metastatic) HER2-positive breast cancer. The combination therapy using trastuzumab and pertuzumab is meanwhile also approved for the neoadjuvant (before surgery) treatment off HER2-positive, locally advanced, inflammatory, or early stage breast cancer and for adjuvant (after surgery) treatment of HER2-positive early breast cancer (EBC) at high risk of recurrence. The mechanisms of action of Perjeta and Herceptin are believed to complement each other, as both bind to the HER2 receptor, but to different places. The combination of Perjeta and Herceptin is thought to provide a more comprehensive, dual blockade of HER signaling pathways, thus preventing tumor cell growth and survival.

Bispecific, bivalent HER-2 antibodies that are directed against domains II, III and IV of human ErbB2 are disclosed in WO 2012/143523. Bispecific HER-2 antibodies comprising optimized variants of the antibodies rhuMab 2C4 and hu4D5, called Herceptarg, have been described in WO 2015/091738.

Although the therapeutic efficacy of trastuzumab in breast carcinoma is well demonstrated, there are many patients who do not benefit from trastuzumab because of resistance.

Given the lack of an effective anti-HER2 therapy in specific cancers expressing low levels of HER2, the resistance to the current therapies, and the prevalence of HER-2 related cancers, new therapies are required to treat such cancers.

4-1BB (CD137), a member of the TNF receptor superfamily, was first identified as an inducible molecule expressed by activated by T cells (Kwon and Weissman, 1989, Proc Natl Acad Sci USA 86, 1963-1967). Subsequent studies demonstrated that many other immune cells also express 4-1BB, including NK cells, B cells, NKT cells, monocytes, neutrophils, mast cells, dendritic cells (DCs) and cells of non-hematopoietic origin such as endothelial and smooth muscle cells (Vinay and Kwon, 2011, Cell Mol Immunol 8, 281-284). Expression of 4-1BB in different cell types is mostly inducible and driven by various stimulatory signals, such as T-cell receptor (TCR) or B-cell receptor triggering, as well as signaling induced through co-stimulatory molecules or receptors of pro-inflammatory cytokines (Diehl et al., 2002, J Immunol 168, 3755-3762; Zhang et al., 2010, Clin Cancer Res 13, 2758-2767).

4-1BB ligand (4-1BBL or CD137L) was identified in 1993 (Goodwin et al., 1993, Eur J Immunol 23, 2631-2641). It has been shown that expression of 4-1BBL was restricted on professional antigen presenting cells (APC) such as B-cells, DCs and macrophages. Inducible expression of 4-1BBL is characteristic for T-cells, including both $\alpha\beta$ and $\gamma\delta$ T-cell subsets, and endothelial cells (Shao and Schwarz, 2011, J Leukoc Biol 89, 21-29).

Co-stimulation through the 4-1BB receptor (for example by 4-1BBL ligation) activates multiple signaling cascades within the T cell (both $CD4^+$ and $CD8^+$ subsets), powerfully augmenting T cell activation (Bartkowiak and Curran, 2015). In combination with TCR triggering, agonistic 4-1BB-specific antibodies enhance proliferation of T-cells, stimulate lymphokine secretion and decrease sensitivity of T-lymphocytes to activation-induced cells death (Snell et al., 2011, Immunol Rev 244, 197-217). This mechanism was further advanced as the first proof of concept in cancer immunotherapy. In a preclinical model administration of an agonistic antibody against 4-1BB in tumor bearing mice led to potent anti-tumor effect (Melero et al., 1997, Nat Med 3, 682-685). Later, accumulating evidence indicated that 4-1BB usually exhibits its potency as an anti-tumor agent only when administered in combination with other immunomodulatory compounds, chemotherapeutic reagents, tumor-specific vaccination or radiotherapy (Bartkowiak and Curran, 2015, Front Oncol 5, 117).

Signaling of the TNFR-superfamily needs cross-linking of the trimerized ligands to engage with the receptors, so does the 4-1BB agonistic antibodies which require wild type Fc-binding (Li and Ravetch, 2011, Science 333, 1030-1034). However, systemic administration of 4-1BB-specific agonistic antibodies with the functionally active Fc domain resulted in influx of $CD8^+$ T-cells associated with liver toxicity (Dubrot et al., 2010, Cancer Immunol Immunother 59, 1223-1233) that is diminished or significantly ameliorated in the absence of functional Fc-receptors in mice. In the clinic, an Fc-competent 4-1BB agonistic Ab (BMS-663513) (NCT00612664) caused a grade 4 hepatitis leading to termination of the trial (Simeone and Ascierto, 2012, J Immunotoxicol 9, 241-247). Therefore, there is a need for effective and safer 4-1BB agonists.

Fusion proteins composed of one extracellular domain of a 4-1BB ligand and a single chain antibody fragment (Hornig et al., 2012, J Immunother 35, 418-429; Müller et al., 2008, J Immunother 31, 714-722) or a single 4-1BB ligand fused to the C-terminus of a heavy chain (Zhang et al., 2007, Clin Cancer Res 13, 2758-2767) have been made. WO 2010/010051 discloses the generation of fusion proteins that consist of three TNF ligand ectodomains linked to each other and fused to an antibody part. In the present invention, antigen binding molecules composed of a trimeric and thus biologically active 4-1BB ligand and an antigen binding domain specific for the tumor-associated antigen and an Fc inactive domain, are shown particularly stable and robust. For tumor specific co-stimulation via 4-1BB (CD137) a molecule comprising an antigen binding domain targeting FAP in the tumor-stroma and a trimer of 4-1BB ligands is shown to be particularly useful, hereinafter named FAP-4-1BBL. The FAP antigen binding domain replaces the unspecific FcγR-mediated crosslinking that is responsible for Fc-mediated toxicity in particular in the liver, by a FAP-targeted specific crosslinking, thus reducing the risk of toxicity.

We herein describe a novel combination therapy for tumors expressing HER-2.

SUMMARY OF THE INVENTION

The present invention relates to 4-1BB (CD137) agonists, in particular 4-1BBL trimer containing antigen binding molecules, and their use in combination with HER-2 targeting therapy, in particular to their use in a method for treating or delaying progression of cancer. It has been found that the combination therapy described herein is more effective in inhibiting tumor growth and eliminating tumor cells than treatment with the 4-1BB agonists or known HER-2 targeting therapies alone.

In some aspects, the invention provides a 4-1BB (CD137) agonist for use in a method for treating or delaying progression of cancer, wherein the 4-1BB agonist is used in combination with a HER-2 targeting agent and wherein the 4-1BB agonist is an antigen binding molecule comprising at least one antigen binding domain capable of specific binding to a tumor-associated antigen.

In some aspects, the HER-2 targeting agent comprises a HER-2 antibody, a bispecific HER-2 antibody and/or a HER-2 antibody drug conjugate. In some aspects, the HER-2 targeting agent comprises trastuzumab, pertuzumab, and/or trastuzumab emtansine. In some aspects, the HER-2 targeting agent is trastuzumab, pertuzumab, and/or trastuzumab emtansine. In some aspects, the HER-2 targeting agent is selected from the group consisting of trastuzumab, pertuzumab, and trastuzumab emtansine. In some aspects, the HER-2 targeting agent comprises a combination of trastuzumab, pertuzumab, and/or trastuzumab emtansine. In some aspects, the HER-2 targeting agent comprises a HER-2 antibody selected from the group consisting of trastuzumab, pertuzumab and margetuximab. In one aspect, the HER-2 targeting agent is trastuzumab or pertuzumab. More particularly, the HER-2 targeting agent is trastuzumab. In some aspects, the HER-2 targeting is a glycoengineered HER-2 antibody, e.g. TrasGex. In some aspects, the HER-2 targeting agent is a bispecific HER-2 antibody, e.g. Herceptarg. In some aspects, the HER-2 targeting agent is a HER-2 antibody drug conjugate, in particular trastuzmab emtansine (ado-trastuzumab emtansine).

In some aspects, the 4-1BB agonist comprises three ectodomains of 4-1BBL or fragments thereof. In some aspects, the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

In further aspects, the 4-1BB agonist is an antigen binding molecule comprising at least one antigen binding domain capable of specific binding to a tumor-associated antigen. In some aspects, the 4-1BB agonist is an antigen binding molecule comprising three ectodomains of 4-1BBL or fragments thereof and at least one antigen binding domain capable of specific binding to a tumor-associated antigen. In one aspect, the tumor-associated antigen selected from the group consisting of Fibroblast activation protein (FAP) and CEA.

In further aspects, the 4-1BB agonist is an antigen binding molecule comprising an IgG Fc domain, specifically an IgG1 Fc domain or an IgG4 Fc domain. In some aspects, the 4-1BB agonist is an antigen binding molecule comprising a Fc domain that comprises one or more amino acid substitution that reduces binding to an Fc receptor and/or effector function. In a particular aspect, the 4-1BB agonist is an antigen binding molecule comprising a Fc domain with modifications reducing Fcγ receptor binding and/or effector function. The crosslinking by a tumor associated antigen makes it possible to avoid unspecific FcγR-mediated crosslinking and thus higher and more efficacious doses of the 4-1BB agonists may be administered in comparison to common 4-1BB antibodies.

In some aspects, the 4-1BB agonist is an antigen binding molecule comprising three ectodomains of 4-1BBL or fragments thereof and at least one antigen binding domain capable of specific binding to Fibroblast activation protein (FAP). In some aspects, the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises
(a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
(b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In another aspect, the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

In some aspects, the 4-1BB agonist is an antigen binding molecule comprising
(a) at least one antigen binding domain capable of specific binding to FAP, and
(b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof. In some aspects, the 4-1BB agonist is an antigen binding molecule comprising (a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In another aspect, the 4-1BB agonist is an antigen binding molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:43 and a second light chain comprising the amino acid sequence of SEQ ID NO:44.

In some aspects, the 4-1BB agonist is an anti-FAP/anti-4-1BB bispecific antibody.

In another aspect, the 4-1BB agonist is an antigen binding molecule comprising three ectodomains of 4-1BBL or fragments thereof and at least one antigen binding domain capable of specific binding to CEA. In some aspects, the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises (a) a heavy chain variable region ($V_H$CEA) comprising (i) CDR-H1 comprising the amino acid sequence of SEQ ID NO:33, (ii) CDR-H2 comprising the amino acid sequence of SEQ ID NO:34, and (iii) CDR-H3 comprising the amino acid sequence of SEQ ID NO:35, and a light chain variable region ($V_L$CEA) comprising (iv) CDR-L1 comprising the amino acid sequence of SEQ ID NO:36, (v) CDR-L2 comprising the amino acid sequence of SEQ ID NO:37, and (vi) CDR-L3 comprising the amino acid sequence of SEQ ID NO:38.

In another aspect, the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:39 and a light chain variable region ($V_L$CEA) comprising an amino acid sequence of SEQ ID NO:40.

In another aspect, the 4-1BB agonist is an antigen binding molecule comprising
(a) at least one antigen binding domain capable of specific binding to CEA, and
(b) a first and a second polypeptide that are linked to each other by a disulfide bond,
wherein the first polypeptide comprises two ectodomains of 4-1BBL or fragments thereof that are connected to each other by a peptide linker and in that the second polypeptide comprises one ectodomain of 4-1BBL or a fragment thereof.

In some aspects, the 4-1BB agonist is an antigen binding molecule comprising
(a) at least one Fab domain capable of specific binding to CEA comprising a heavy chain variable region ($V_H$-CEA) comprising the amino acid sequence of SEQ ID NO:39 and a light chain variable region ($V_L$CEA) comprising the amino acid sequence of SEQ ID NO:40, and
(b) a first and a second polypeptide that are linked to each other by a disulfide bond,
wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In a further aspect, the 4-1BB agonist is an anti-CEA/anti-4-1BB bispecific antibody.

In other aspects, the 4-1BB agonist and the HER-2 targeting agent are administered together in a single composition or administered separately in two or more different compositions. In further aspects, the 4-1BB agonist acts synergistically with the HER-2 targeting agent. In other aspects, the 4-1BB agonist is administered concurrently with, prior to, or subsequently to the HER-2 targeting agent.

In further aspects, provided is a combination comprising a 4-1BB agonist and a HER-2 targeting agent. In one aspect, the combination is for use as a medicament, wherein the 4-1BB agonist and a HER-2 targeting agent are for simultaneous administration. In other aspects, the combination is for use as a medicament, wherein the 4-1BB agonist and a HER-2 targeting agent are for sequential administration.

In another aspect, there is provided a pharmaceutical product comprising (A) a first composition comprising as active ingredient a 4-1BB agonist and a pharmaceutically acceptable carrier; and (B) a second composition comprising as active ingredient a HER-2 targeting agent and a pharmaceutically acceptable carrier, for use in the combined, sequential or simultaneous, treatment of a disease, in particular cancer.

In a further aspect, there is provided a pharmaceutical composition comprising a 4-1BB agonist and a HER-2 targeting agent. In some aspects, the HER-2 targeting agent comprises trastuzumab, pertuzumab, and/or trastuzumab emtansine. In some aspects, the HER-2 targeting agent is selected from the group consisting of trastuzumab, pertuzumab, and trastuzumab emtansine. In some aspects, the HER-2 targeting agent is a combination of trastuzumab, pertuzumab, and/or trastuzumab emtansine. In further aspects, there is provided the pharmaceutical composition for use in treating or delaying progression of cancer, in particular for the treatment of advanced and/or metastatic solid tumors.

In a further aspect, the invention relates to the use of a combination of a 4-1BB agonist and a HER-2 targeting agent in the manufacture of a medicament for treating or delaying progression of a proliferative disease, in particular cancer. In some aspects, the HER-2 targeting agent comprises trastuzumab, pertuzumab, and/or trastuzumab emtansine. In some aspects, the HER-2 targeting agent is selected from the group consisting of trastuzumab, pertuzumab, and trastuzumab emtansine. In some aspects, the HER-2 targeting agent is a combination of trastuzumab, pertuzumab, and/or trastuzumab emtansine.

In another aspect, the invention provides a method for treating or delaying progression of cancer in a subject comprising administering to the subject an effective amount of a 4-1BB agonist and an effective amount of a HER-2 targeting agent. In some aspects, the HER-2 targeting agent comprises trastuzumab, pertuzumab, and/or trastuzumab emtansine. In some aspects, the HER-2 targeting agent is selected from the group consisting of trastuzumab, pertuzumab, and trastuzumab emtansine. In some aspects, the HER-2 targeting agent is a combination of trastuzumab, pertuzumab, and/or trastuzumab emtansine.

In some aspects, the invention relates to a method for treating or delaying progression of cancer in a subject, comprising administering to the subject an effective amount of a 4-1BB agonist and an effective amount of a HER-2 targeting agent, wherein the 4-1BB agonist comprises three ectodomains of 4-1BBL or fragments thereof. In some aspects, the 4-1BB agonist is any 4-1BB agonist provided herein. In some aspects, the 4-1BB agonist and the HER-2 targeting agent are administered together in a single composition or administered separately in two or more different compositions. In some aspects, the 4-1BB agonist and the HER-2 targeting agent are administered intravenously or subcutaneously. In some aspects, the 4-1BB agonist is administered concurrently with, prior to, or subsequently to the HER-2 targeting agent.

In further aspects, the invention relates to a 4-1BB agonist in combination with a HER-2 targeting agent or pharmaceutical composition for use in treating or delaying progression of cancer, a use of a combination of a 4-1BB agonist and a HER-2 targeting agent in the manufacture of a medicament for treating or delaying progression of a proliferative disease, in particular cancer, or a method for treating or delaying progression of cancer in a subject, wherein the cancer cancer is a HER-2 positive cancer. In some aspects, the cancer is breast cancer, ovarian cancer, stomach cancer, gastric cancer, oesophageal cancer, lung cancer, uterine cancer, salivary duct carcinoma, bladder cancer, endometrial cancer, pancreatic cancer, colon cancer, prostate cancer, and/or head and neck cancer.

BRIEF DESCRIPTION OF THE DRAWINGS

FIG. 1A shows a monovalent FAP 4-1BBL-trimer containing antigen binding molecule with modifications in the CH1 and CL domain adjacent to the 4-1BBL dimer and 4-1BBL monomer. As it comprised the FAP binder 4B9, it was named mono FAP(4B9)-4-1BBL herein. FIG. 1B shows the bivalent construct with binder FAP(4B9), termed bi FAP(4B9)-4-1BBL. FIG. 1C and FIG. 1D show untargeted control molecules (the FAP binder has been replaced by a non-binding DP47 Fab).

FIG. 4A and FIG. 4B show the treatment schedule and treatment groups of huCD16TgScid mice as described in Example 5.

DETAILED DESCRIPTION OF THE INVENTION

Definitions

Figure 1A:
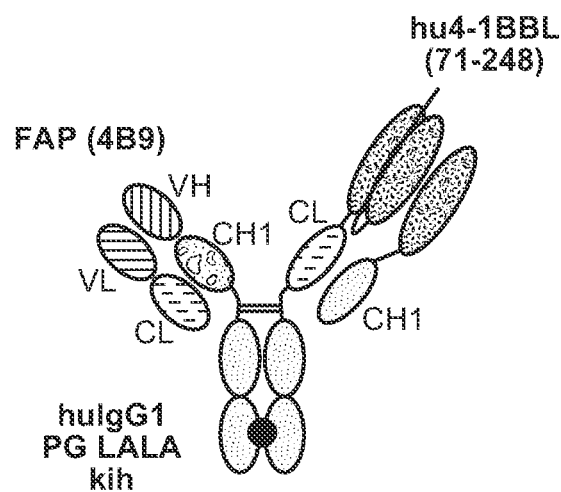
FIG. 1A, FIG. 1B, FIG. 1C, and FIG. 1D shows particular FAP-4-1BBL antigen binding molecules. These molecules are described in more detail in Example 1. The thick black point stands for the knob-into-hole modification.

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteines from the antibody hinge region. Fab'-SH are Fab' fragments in which the cysteine residue(s) of the constant domains bear a free thiol group. Pepsin treatment yields an F(ab')$_2$ fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin).

Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633.

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation).

For further details see J. Mol. Biol. 332, 489-503 (2003), PNAS 100(4), 1700-1705 (2003) and J. Mol. Biol. 369, 1015-1028 (2007) and US20040132028A1.

A single-domain antibody is an antibody fragment consisting of a single monomeric variable antibody domain. The first single domains were derived from the variable domain of the antibody heavy chain from camelids (nanobodies or $V_HH$ fragments). Furthermore, the term single-domain antibody includes an autonomous human heavy chain variable domain (aVH) or $V_{NAR}$ fragments derived from sharks.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, a molecule that binds to the antigen has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

The term "tumor-associated antigen" means any antigen that is highly expressed by tumor cells or in the tumor stroma. Particular tumor-associated antigens are CEA or FAP.

The term "Fibroblast activation protein (FAP)", also known as Prolyl endopeptidase FAP or Seprase (EC 3.4.21), refers to any native FAP from any vertebrate source, including mammals such as primates (e.g. humans) non-human primates (e.g. cynomolgus monkeys) and rodents (e.g. mice and rats), unless otherwise indicated. The term encompasses "full-length," unprocessed FAP as well as any form of FAP which results from processing in the cell. The term also encompasses naturally occurring variants of FAP, e.g., splice variants or allelic variants. In one embodiment, the antigen binding molecule of the invention is capable of specific binding to human, mouse and/or cynomolgus FAP. The amino acid sequence of human FAP is shown in UniProt (www.uniprot.org) accession no. Q12884 (version 149, SEQ ID NO:56), or NCBI (www.ncbi.nlm.nih.gov/) RefSeq NP_004451.2. The extracellular domain (ECD) of human FAP extends from amino acid position 26 to 760. The amino acid sequence of a His-tagged human FAP ECD is shown in SEQ ID NO: 81. The amino acid sequence of mouse FAP is shown in UniProt accession no. P97321 (version 126, SEQ ID NO:58), or NCBI RefSeq NP_032012.1. The extracellular domain (ECD) of mouse FAP extends from amino acid position 26 to 761. SEQ ID NO: 83 shows the amino acid sequence of a His-tagged mouse FAP ECD. SEQ ID NO: 84 shows the amino acid sequence of a His-tagged cynomolgus FAP ECD. Preferably, an anti-FAP binding molecule of the invention binds to the extracellular domain of FAP. Exemplary anti-FAP binding molecules are described in International Patent Application No. WO 2012/020006 A2.

The term "Carcinoembroynic antigen (CEA)", also known as Carcinoembryonic antigen-related cell adhesion molecule 5 (CEACAM5), refers to any native CEA from any vertebrate source, including mammals such as primates (e.g. humans) non-human primates (e.g. cynomolgus monkeys) and rodents (e.g. mice and rats), unless otherwise indicated. The amino acid sequence of human CEA is shown in UniProt accession no. P06731 (version 151, SEQ ID NO:61). CEA has long been identified as a tumor-associated antigen (Gold and Freedman, J Exp Med., 121:439-462, 1965; Berinstein N. L., J Clin Oncol., 20:2197-2207, 2002). Originally classified as a protein expressed only in fetal tissue, CEA has now been identified in several normal adult tissues. These tissues are primarily epithelial in origin, including cells of the gastrointestinal, respiratory, and urogential tracts, and cells of colon, cervix, sweat glands, and prostate (Nap et al., Tumour Biol., 9(2-3):145-53, 1988; Nap et al., Cancer Res., 52(8):2329-23339, 1992). Tumors of epithelial origin, as well as their metastases, contain CEA as a tumor associated antigen. While the presence of CEA itself does not indicate transformation to a cancerous cell, the distribution of CEA is indicative. In normal tissue, CEA is generally expressed on the apical surface of the cell (Hammarström S., Semin Cancer Biol. 9(2):67-81 (1999)), making it inaccessible to antibody in the blood stream. In contrast to normal tissue, CEA tends to be expressed over the entire surface of cancerous cells (Hammarström S., Semin Cancer Biol. 9(2):67-81 (1999)). This change of expression pattern makes CEA accessible to antibody binding in cancerous cells. In addition, CEA expression increases in cancerous cells. Furthermore, increased CEA expression promotes increased intercellular adhesions, which may lead to metastasis (Marshall J., Semin Oncol., 30(a Suppl. 8):30-6, 2003). The prevalence of CEA expression in various tumor entities is generally very high. In concordance with published data, own analyses performed in tissue samples confirmed its high prevalence, with approximately 95% in colorectal carcinoma (CRC), 90% in pancreatic cancer, 80% in gastric cancer, 60% in non-small cell lung cancer (NSCLC, where it is co-expressed with HER3), and 40% in breast cancer; low expression was found in small cell lung cancer and glioblastoma.

CEA is readily cleaved from the cell surface and shed into the blood stream from tumors, either directly or via the lymphatics. Because of this property, the level of serum CEA has been used as a clinical marker for diagnosis of cancers and screening for recurrence of cancers, particularly colorectal cancer (Goldenberg D M., The International Journal of Biological Markers, 7:183-188, 1992; Chau I., et al., J Clin Oncol., 22:1420-1429, 2004; Flamini et al., Clin Cancer Res; 12(23):6985-6988, 2006).

A "T-cell antigen" as used herein refers to an antigenic determinant presented on the surface of a T lymphocyte, particularly a cytotoxic T lymphocyte.

A "T cell activating therapeutic agent" as used herein refers to a therapeutic agent capable of inducing T cell activation in a subject, particularly a therapeutic agent designed for inducing T-cell activation in a subject.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, MD (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., J. Mol. Biol. 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table B as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The "knob-into-hole" technology is described e.g. in U.S. Pat. Nos. 5,731,168, 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

An "ectodomain" is the domain of a membrane protein that extends into the extracellular space (i.e. the space outside the target cell). Ectodomains are usually the parts of proteins that initiate contact with surfaces, which leads to signal transduction. The ectodomain of 4-1BBL as defined herein thus refers to the part of the 4-1BBL that extends into the extracellular space (the extracellular domain), but also includes shorter parts or fragments thereof that are responsible for the trimerization and for the binding to the corresponding receptor 4-1BB. The term "ectodomain of 4-1BBL or a fragment thereof" thus refers to the extracellular domain of 4-1BBL that forms the extracellular domain or to parts thereof that are still able to bind to the receptor (receptor binding domain).

"4-1BBL" or "4-1BB ligand" or "CD137L" is a costimulatory TNF ligand family member, which is able to costimulate proliferation and cytokine production of T-cells. Costimulatory TNF family ligands can costimulate TCR signals upon interaction with their corresponding TNF receptors and the interaction with their receptors leads to recruitment of TNFR-associated factors (TRAF), which initiate signalling cascades that result in T-cell activation. 4-1BBL is a type II transmembrane protein. Complete or full length 4-1BBL having the amino acid sequence of SEQ ID NO:62 has been described to form trimers on the surface of cells. The formation of trimers is enabled by specific motives of the ectodomain of 4-1BBL. Said motives are designated herein as "trimerization region". The amino acids 50-254 of the human 4-1BBL sequence (SEQ ID NO:63) form the extracellular domain of 4-1BBL, but even fragments thereof are able to form the trimers. In specific embodiments of the invention, the term "ectodomain of 4-1BBL or a fragment thereof" refers to a polypeptide having an amino acid sequence selected from SEQ ID NO:4 (amino acids 52-254 of human 4-1BBL), SEQ ID NO:1 (amino acids 71-254 of human 4-1BBL), SEQ ID NO:3 (amino acids 80-254 of human 4-1BBL), SEQ ID NO:2 (amino acids 85-254 of human 4-1BBL), SEQ ID NO:5 (amino acids 71-248 of human 4-1BBL), SEQ ID NO:6 (amino acids 85-248 of human 4-1BBL), SEQ ID NO:7 (amino acids 80-248 of human 4-1BBL) and SEQ ID NO:8 (amino acids 52-248 of human 4-1BBL), but also other fragments of the ectodomain capable of trimerization are included herein.

The term "4-1BB" or "CD137", as used herein, refers to any native 4-1BB from any vertebrate source, including mammals such as primates (e.g. humans) and rodents (e.g., mice and rats), unless otherwise indicated. The term encompasses "full-length," unprocessed 4-1BB as well as any form of 4-1BB that results from processing in the cell. The term also encompasses naturally occurring variants of 4-1BB, e.g., splice variants or allelic variants. The amino acid sequence of an exemplary human 4-1BB is shown in SEQ ID NO: 88 (Uniprot accession no. Q07011), the amino acid sequence of an exemplary murine 4-1BB is shown in SEQ ID NO: 89 (Uniprot accession no. P20334) and the amino acid sequence of an exemplary cynomolgous 4-1BB (from Macaca mulatta) is shown in SEQ ID NO:66 (Uniprot accession no. F6W5G6).

The terms "anti-4-1BB antibody", "anti-4-1BB", "4-1BB antibody and "an antibody that specifically binds to 4-1BB" refer to an antibody that is capable of binding 4-1BB with sufficient affinity such that the antibody is useful as a diagnostic and/or therapeutic agent in targeting 4-1BB. In one embodiment, the extent of binding of an anti-4-1BB antibody to an unrelated, non-4-1BB protein is less than about 10% of the binding of the antibody to 4-1BB as measured, e.g., by a radioimmunoassay (RIA) or flow cytometry (FACS). In certain embodiments, an antibody that binds to 4-1BB has a dissociation constant ($K_D$) of ≤1 μM, ≤100 nM, ≤10 nM, ≤1 nM, ≤0.1 nM, ≤0.01 nM, or ≤0.001 nM (e.g. $10^{-6}$ M or less, e.g. from $10^{-68}$ M to $10^{-13}$ M, e.g., from $10^{-8}$ M to $10^{-10}$ M).

The term "HER-2", also known as "ErbB2", "ErbB2 receptor", or "c-Erb-B2", refers to any native, mature HER-2 which results from processing of a HER-2 precursor protein in a cell. The term includes HER-2 from any vertebrate source, including mammals such as primates (e.g. humans and cynomolgus monkeys) and rodents (e.g., mice and rats), unless otherwise indicated. The term also includes naturally occurring variants of HER-2, e.g., splice variants or allelic variants. The amino acid sequence of an exemplary human HER-2 protein is shown in SEQ ID NO:95.

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 2 and 4, in particular 2, i.e. the peptides selected from the group consisting of GGGGS (SEQ ID NO:67) GGGGSGGGGS (SEQ ID NO:68), SGGGGSGGGG (SEQ ID NO:69) and GGGGSGGGGSGGGG (SEQ ID NO:70), but also include the sequences GSPGSSSSGS (SEQ ID NO:71), $(G4S)_3$ (SEQ ID NO:72), $(G4S)_4$ (SEQ ID NO:73), GSGSGSGS (SEQ ID NO:74), GSGSGNGS (SEQ ID NO:75), GGSGSGSG (SEQ ID NO:76), GGSGSG (SEQ ID NO:77), GGSG (SEQ ID NO:78), GGSGNGSG (SEQ ID NO:79), GGNGSGSG (SEQ ID NO:80) and GGNGSG (SEQ ID NO:81). Peptide linkers of particular interest are (G4S) (SEQ ID NO:67), (G$_4$S)$_2$ and GGGGSGGGGS (SEQ ID NO:68).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a polypeptide and an ectodomain of 4-1BBL) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the antigen binding molecules provided herein are contemplated. For example, it may be desirable to improve the binding affinity and/or other biological properties of the antigen binding molecules. Amino acid sequence variants of the antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table C under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE B

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more CDR residues are mutated and the variant antigen binding molecules displayed on phage and screened for a particular biological activity (e.g. binding affinity). In certain embodiments, substitutions, insertions, or deletions may occur within one or more CDRs so long as such alterations do not substantially reduce the ability of the antigen binding molecule to bind antigen. For example, conservative alterations (e.g., conservative substitutions as provided herein) that do not substantially reduce binding affinity may be made in CDRs. A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antigen binding molecules with an N-terminal methionyl residue. Other insertional variants of the molecule include the fusion to the N- or C-terminus to a polypeptide which increases the serum half-life of the antigen binding molecules.

In certain embodiments, the antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antigen binding molecules may be made in order to create variants with certain improved properties. In one aspect, variants of antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the antigen binding molecules of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed. In another aspect, immunoconjugates of the 4-1BBL-containing antigen binding molecules provided herein maybe obtained. An "immunoconjugate" is an antibody conjugated to one or more heterologous molecule(s), including but not limited to a cytotoxic agent.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

The combination therapies in accordance with the invention have a synergistic effect. A "synergistic effect" of two compounds is one in which the effect of the combination of the two agents is greater than the sum of their individual effects and is statistically different from the controls and the single drugs. In another embodiment, the combination therapies disclosed herein have an additive effect. An "additive effect" of two compounds is one in which the effect of the combination of the two agents is the sum of their individual effects and is statistically different from either the controls and/or the single drugs.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The terms "cancer" and "cancerous" refer to or describe the physiological condition in mammals that is typically characterized by unregulated cell growth, i.e proliferative diseases, such as solid tumors or melanoma. A "tumor" comprises one or more cancerous cells. The term "solid tumor" as used herein refers to an abnormal mass of tissue that usually does not contain cysts or liquid areas. Solid tumors may be benign or malignant. Examples of cancer include, but are not limited to, carcinoma, lymphoma, blastoma, sarcoma, and leukemia or lymphoid malignancies. More particular examples of such cancers include breast cancer, squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. In a preferred embodiment, the cancer is breast cancer. In another preferred embodiment, the cancer is gastric cancer.

Reference to a tumor or cancer as a "Stage 0," "Stage I," "Stage II," "Stage III," or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor is known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

An "advanced" cancer is one which has spread outside the site or organ of origin, either by local invasion or metastasis. Accordingly, the term "advanced" cancer includes both locally advanced and metastatic disease. A "refractory" cancer is one which progresses even though an anti-tumor agent, such as a chemotherapy, is being administered to the cancer patient. An example of a refractory cancer is one which is platinum refractory. A "recurrent" cancer is one which has regrown, either at the initial site or at a distant site, after a response to initial therapy, such as surgery. A "locally recurrent" cancer is cancer that returns after treatment in the same place as a previously treated cancer. An "operable" or "resectable" cancer is cancer which is confined to the primary organ and suitable for surgery (resection). A "non-resectable" or "unresectable" cancer is not able to be removed (resected) by surgery.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

The terms "HER-2-positive" and "HER-2 expressing" are used herein interchangeably. A "HER-2-positive" cancer comprises cancer cells which have higher than normal levels of HER-2. Examples of HER-2-positive cancer include HER-2-positive breast cancer and HER2-positive gastric cancer. Optionally, HER2-positive is a HER-2 overexpressing cancer, and in certain embodiments the HER-2 positive cancer has an immunohistochemistry (HC) score of 2+ or 3+ and/or an in situ hybridization (ISH) amplification ratio ≥2.0.

In situ hybridization (ISH) determines the number of her2 copies using a DNA probe coupled to a fluorescent, chromogenic, or silver detection system (ie, FISH, CISH, or SISH), or a combination of CISH and SISH systems (brightfield double ISH (BDISH) or dual-hapten, dual-color ISH (DDISH)). ISH may be conducted using a single probe to enumerate her2 copies per nucleus only or as a dual-probe technique where hybridization of a chromosome 17 centromere probe (chromosome enumeration probe 17, CEP17) allows determination of the her2:CEP17 ratio. The two-probe approach may be performed as a dual-color technique, with cohybridization of the two probes on the same slide, or as a monochrome assay where each probe is used on sequential slides. The her2:CEP17 ratio is sometimes regarded as a better reflection of her2 amplification status than mean her2 copy number, as the latter is also dependent on other parameters, such as the mitotic index of the tumor, section thickness, nuclear truncation effects, and abnormal chromosome copy number (aneusomy). The phrase "situ hybridization (ISH) amplification ratio ≥2.0" refers to her2:CEP17 ratio ≥2.0. For further details see, e.g. Sauter G, et al.

Guidelines for human epidermal growth factor receptor 2 testing: biologic and methodologic considerations. *J Clin Oncol* 2009; 27: 1323-1333, and the review article by Hanna et al. *Modern Pathology* (2014) 27, 4-18.

Herein, a "patient" or "subject" is a human patient. The patient may be a "cancer patient," i.e. one who is suffering or at risk for suffering from one or more symptoms of cancer, in particular gastric or breast cancer.

A "patient population" refers to a group of cancer patients. Such populations can be used to demonstrate statistically significant efficacy and/or safety of a drug, such as Pertuzumab. A "relapsed" patient is one who has signs or symptoms of cancer after remission. Optionally, the patient has relapsed after adjuvant or neoadjuvant therapy.

"Neoadjuvant therapy" or "preoperative therapy" herein refers to therapy given prior to surgery. The goal of neoadjuvant therapy is to provide immediate systemic treatment, potentially eradicating micrometastases that would otherwise proliferate if the standard sequence of surgery followed by systemic therapy were followed. Neoadjuvant therapy may also help to reduce tumor size thereby allowing complete resection of initially unresectable tumors or preserving portions of the organ and its functions. Furthermore, neoadjuvant therapy permits an in vivo assessment of drug efficacy, which may guide the choice of subsequent treatments.

"Adjuvant therapy" herein refers to therapy given after definitive surgery, where no evidence of residual disease can be detected, so as to reduce the risk of disease recurrence. The goal of adjuvant therapy is to prevent recurrence of the cancer, and therefore to reduce the chance of cancer-related death. Adjuvant therapy herein specifically excludes neoadjuvant therapy.

"Chemotherapy" refers to the use of a chemotherapeutic agent useful in the treatment of cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors.

"CD20" refers to B-lymphocyte antigen CD20, also known as B-lymphocyte surface antigen B1 or Leukocyte surface antigen Leu-16, and includes any native CD20 from any vertebrate source, including mammals such as primates (e.g. humans) non-human primates (e.g. cynomolgus monkeys) and rodents (e.g. mice and rats), unless otherwise indicated. The amino acid sequence of human CD20 is shown in Uniprot accession no. P11836 (version 149, SEQ ID NO:85). CD20 is a hydrophobic transmembrane protein with a molecular weight of approximately 35 kD expressed on pre-B and mature B lymphocytes. The corresponding human gene is membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein. The term "CD20" encompasses "full-length," unprocessed CD20 as well as any form of CD20 that results from processing in the cell. The term also encompasses naturally occurring variants of CD20, e.g., splice variants or allelic variants.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-CD20 antibody binds to an epitope of CD20 that is conserved among CD20 from different species.

By "Type II anti-CD20 antibody" is meant an anti-CD20 antibody having binding properties and biological activities of Type II anti-CD20 antibodies as described in Cragg et al., Blood 103 (2004) 2738-2743; Cragg et al., Blood 101 (2003) 1045-1052, Klein et al., mAbs 5 (2013), 22-33. A type II anti-CD20 antibody binds to class II epitope on CD20, it does not localize CD20 to lipid rafts, shows ADCC activity, but low CDC if it is a IgG1 isotype antibody, has less binding capacity to B cells compared with antibodies binding to the Class I CD20 epitope, shows homotypic aggregation and strong death induction. Examples of type II anti-CD20 antibodies include e.g. obinutuzumab (GA101), tositumumab (B1), humanized B-Ly1 antibody IgG1 (a chimeric humanized IgG1 antibody as disclosed in WO 2005/044859), 11B8 IgG1 (as disclosed in WO 2004/035607) and AT80 IgG1. In a particular aspect, the Type II anti-CD20 antibody is obinutuzumab (recommended INN, WHO Drug Information, Vol. 26, No. 4, 2012, p. 453). As used herein, obinutuzumab is synonymous for GA101. The tradename is GAZYVA® or GAZYVARO®. This replaces all previous versions (e.g. Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124). In one aspect, the Type II anti-CD20 antibody is tositumomab.

Exemplary 4-1BB Agonists for Use in the Invention

The present invention relates to 4-1BB agonists and their use in combination with HER-2 targeting therapy, in particular their use in a method for treating or delaying progression of cancer. In some embodiments, the 4-1BB agonists and their use in combination with HER-2 targeting therapy is in a method for treating or delaying progression of solid tumors.

In particular, the 4-1BB agonists as used in combination with HER-2 targeting therapy are molecules comprising 4-1BBL. In particular, the 4-1BB agonist used in the invention comprises three ectodomains of 4-1BBL or fragments thereof.

In a particular aspect, the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

The 4-1BB agonist is especially useful if it comprises an antigen binding domain that is specific for a tumor-associated antigen, in particular for a target on cancer cells or in the stroma. Thus, in a particular aspect, the 4-1BB agonist is an antigen binding molecule comprising three ectodomains of 4-1BBL or fragments thereof and at least one antigen binding domain capable of specific binding to Fibroblast activation protein (FAP) or CEA.

In a further aspect, the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises
(a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
(b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In a particular aspect, the antigen binding domain capable of specific binding to FAP comprises a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In a further aspect, the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24. More particularly, the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

In another aspect, the 4-1BB agonist is an antigen binding molecule further comprising a Fc domain composed of a first and a second subunit capable of stable association. In one aspect, the 4-1BB agonist is an antigen binding molecule comprising an IgG Fc domain, specifically an IgG1 Fc domain or an IgG4 Fc domain. Particularly, the 4-1BB agonist is an antigen binding molecule comprising a Fc domain that comprises one or more amino acid substitution that reduces binding to an Fc receptor and/or effector function. In a particular aspect, the 4-1BB agonist is an antigen binding molecule comprising an IgG1 Fc domain comprising the amino acid substitutions L234A, L235A and P329G.

In one aspect, the 4-1BB agonist is an antigen binding molecule comprising
(a) at least one antigen binding domain capable of specific binding to FAP,
(b) a first and a second polypeptide that are linked to each other by a disulfide bond,
wherein the first polypeptide comprises two ectodomains of 4-1BBL or fragments thereof that are connected to each other by a peptide linker and in that the second polypeptide comprises one ectodomain of 4-1BBL or a fragment thereof.

In a particular aspect, the 4-1BB agonist is an antigen binding molecule comprising
(a) at least one Fab domain capable of specific binding to FAP, and
(b) a first and a second polypeptide that are linked to each other by a disulfide bond,
wherein the antigen binding molecule is characterized in that
  (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or
  (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
  (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

In another aspect, the 4-1BB agonist is an antigen binding molecule comprising
(a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region (V$_L$FAP) comprising the amino acid sequence of SEQ ID (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In a particular aspect, the 4-1BB agonist is an antigen binding molecule selected from the group consisting of a) a molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:43 and a second light chain comprising the amino acid sequence of SEQ ID NO:44; and b) a molecule comprising a first heavy chain comprising the amino acid sequence of SEQ ID NO:45, a first light chain comprising the amino acid sequence of SEQ ID NO:46, a second heavy chain comprising the amino acid sequence of SEQ ID NO:47 and a second light chain comprising the amino acid sequence of SEQ ID NO:48.

Particularly, the 4-1BB agonist is an antigen binding molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:43 and a second light chain comprising the amino acid sequence of SEQ ID NO:44.

In another aspect, the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

In one aspect, the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

Particular bispecific antibodies are described in PCT publication No. WO 2016/075278 A1 or in PCT publication No. WO 2016/156291A1.

In a further aspect, the 4-1BB agonist is an anti-FAP/anti-4-1BB bispecific antibody.

In another aspect, the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region (V$_H$CEA) comprising (i) CDR-H1 comprising the amino acid sequence of SEQ ID NO:33, (ii) CDR-H2 comprising the amino acid sequence of SEQ ID NO:34, and (iii) CDR-H3 comprising the amino acid sequence of SEQ ID NO:35, and a light chain variable region (V$_L$CEA) comprising (iv) CDR-L1 comprising the amino acid sequence of SEQ ID NO:36, (v) CDR-L2 comprising the amino acid sequence of SEQ ID NO:37, and (vi) CDR-L3 comprising the amino acid sequence of SEQ ID NO:38.

In a further aspect, the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region (V$_H$CEA) comprising an amino acid sequence of SEQ ID NO:39 and a light chain variable region (V$_L$CEA) comprising an amino acid sequence of SEQ ID NO:40.

In another aspect, the 4-1BB agonist is an antigen binding molecule further comprising a Fc domain composed of a first and a second subunit capable of stable association. In one aspect, the 4-1BB agonist is an antigen binding molecule comprising an IgG Fc domain, specifically an IgG1 Fc domain or an IgG4 Fc domain. Particularly, the 4-1BB agonist is an antigen binding molecule comprising a Fc domain that comprises one or more amino acid substitution that reduces binding to an Fc receptor and/or effector function. In a particular aspect, the 4-1BB agonist is an antigen binding molecule comprising an IgG1 Fc domain comprising the amino acid substitutions L234A, L235A and P329G.

In one aspect, the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

In a particular aspect, the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

In another aspect, the 4-1BB agonist is an antigen binding molecule comprising (a) at least one Fab domain capable of specific binding to CEA comprising a heavy chain variable region ($V_H$ CEA) comprising the amino acid sequence of SEQ ID NO:39 and a light chain variable region ($V_L$CEA) comprising the amino acid sequence of SEQ ID NO:40, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In a particular aspect, the 4-1BB agonist is an antigen binding molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:82 and a second light chain comprising the amino acid sequence of SEQ ID NO:83.

In another aspect, the 4-1BB agonist is an antigen binding molecule comprising
(a) at least one antigen binding domain capable of specific binding to CEA,
(b) a polypeptide comprising three ectodomains of 4-1BBL or fragments thereof that are connected to each other by peptide linkers.

In one aspect, the 4-1BB agonist is an antigen binding molecule comprising
(a) at least one antigen binding domain capable of specific binding to CEA,
(b) a polypeptide comprising three ectodomains of 4-1BBL or fragments thereof that are connected to each other by peptide linkers, and
(c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

In another aspect, the 4-1BB agonist comprises an anti-CEA/anti-4-1BB bispecific antibody.

Agents Targeting HER-2

In aspects of the present invention, a 4-1BB agonist described herein is used in combination with HER-2 targeting therapy.

In some aspects of the present invention, the 4-1BB agonist is used in combination with a HER-2 targeting agent. In some embodiments, the agent interacts with HER-2. In some embodiments, the agent is a HER-2 antagonist. In some aspects, the HER-2 targeting agent comprises a HER-2 antibody, a bispecific HER-2 antibody and/or a HER-2 antibody drug conjugate. In some embodiments, the agent is an antibody or antigen binding fragment, in particular an anti-HER-2 antibody. In some embodiments, the agent is a bispecific HER-2 antibody. In some embodiments, the agent is an antibody-drug conjugate.

In some aspects, the HER-2 targeting agent comprises trastuzumab, pertuzumab, and/or trastuzumab emtansine. In some aspects, the HER-2 targeting agent is trastuzumab, pertuzumab, and/or trastuzumab emtansine. In some aspects, the HER-2 targeting agent is selected from the group consisting of trastuzumab, pertuzumab, and trastuzumab emtansine. In some aspects, the HER-2 targeting agent comprises a combination of trastuzumab, pertuzumab, and/or trastuzumab emtansine. In some aspects, the HER-2 targeting agent comprises a HER-2 antibody selected from the group consisting of trastuzumab, pertuzumab and margetuximab. In one aspect, the HER-2 targeting agent is trastuzumab or pertuzumab. More particularly, the HER-2 targeting agent is trastuzumab. In some aspects, the HER-2 targeting is a glycoengineered HER-2 antibody, e.g. TrasGex. In some aspects, the HER-2 targeting agent is a bispecific HER-2 antibody, e.g. Herceptarg. In some aspects, the HER-2 targeting agent is a HER-2 antibody drug conjugate, in particular trastuzmab emtansine (ado-trastuzumab emtansine).

In some aspects, the HER-2 targeting agent comprises an antibody comprising a heavy chain variable domain (VH) of SEQ ID NO:96 and a light chain variable domain (VL) of SEQ ID NO:97. In some aspects, the HER-2 targeting agent comprises an antibody comprising a heavy chain variable domain (VH) of SEQ ID NO:98 and a light chain variable domain (VL) of SEQ ID NO:99.

In some embodiments, and for any use described herein, the agent comprises trastuzumab (CAS 180288-69-1, HERCEPTIN®, huMAb4D5-8, rhuMAb HER2, Genentech), pertuzumab (rhuMAb 2C4, PERJETA®, Genentech, Inc, South San Francisco) or trastuzumab emtansine (Trastuzumab-MCC-DM1, T-DM1, ado-trastuzumab emtansine, KADCYLA®). In some embodiments, the HER-2 targeting agent is trastuzumab, pertuzumab, and/or trastuzumab emtansine. In some embodiments, the HER-2 targeting agent is selected from the group consisting of trastuzumab, pertuzumab, and trastuzumab emtansine. In some embodiments, the HER-2 targeting agent comprises or consists of a combination of trastuzumab, pertuzumab, and/or trastuzumab emtansine. In some embodiments, the HER-2 targeting agent comprises or consists of a combination of trastuzumab and pertuzumab. More particularly, the agent is trastuzumab.

Trastuzumab is a recombinant DNA-derived, IgG1 kappa, monoclonal antibody that is a humanized version of a murine anti-HER-2 antibody (4D5) that selectively binds with high affinity in a cell-based assay (Kd=5 nM) to the extracellular domain of HER-2. Trastuzumab is an antibody that has antigen binding residues of, or derived from, the murine 4D5 antibody (ATCC CRL 10463, deposited with American Type Culture Collection, 12301 Parklawn Drive, Rockville, Md. 20852 under the Budapest Treaty on May 24, 1990). Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337.

Pertuzumab is a recombinant humanized monoclonal antibody, generated based on human IgG1(K) framework, see for example U.S. Pat. No. 7,560,111. Pertuzumab differs from trastuzumab in the epitope binding regions of the light chain (12 amino acid differences) and the heavy chain (30 amino acid differences). As a result of these differences, pertuzumab binds to a completely different epitope on the HER2 receptor. Binding of pertuzumab to the HER2 receptor on human epithelial cells prevents it from forming complexes with other members of the HER receptor family (Agus et al., Cancer Cell 2:127-137 (2002)). By blocking complex formation, pertuzumab prevents the growth-stimulatory effects of ligands for the complexes (e.g., EGF and heregulin).

Trastuzumab emtansine is an antibody-drug conjugate where trastuzumab is linked through linker moiety MCC to the maytansinoid dru moiety DM1 (U.S. Pat. Nos. 5,208,020; 6,441,163). The drug to antibody ratio or drug loading ranges in integer values from 1 to about 8. Trastuzumab-MCC-DM1 includes all mixtures of variously loaded and attached antibody-drug conjugates where 1, 2, 3, 4, 5, 6, 7, and 8 drug moieties are covalently attached to the antibody trastuzumab (U.S. Pat. No. 7,097,840; US 2005/0276812; US 2005/0166993). Average drug load is about 3.5.

Trastuzumab, pertuzumab and trastuzumab emtansine may be used in any combination. In some embodiments, the HER-2 targeting agent comprises trastuzumab and pertuzumab.

The terms "HER-2 targeting therapy", "HER-2 targeting agent" and "agent that interacts with HER-2" as used herein refers to an agent or agents which target the HER-2 (ErbB2) receptor tyrosine kinase. In particular, the term refers to an agent or agents which selectively bind to HER-2. The agent(s) may be an antibody, in particular a monoclonal antibody. In some cases, the agent(s) selectively binds to HER-2 with high affinity, for example in the nM or pM range. In some cases, the agent(s) binds to the extracellular domain of the HER-2 receptor. An agent(s) may cause: downregulation of HER-2 receptor expression, inhibition of proliferation of human tumour cells that overexpress HER-2 protein, enhancement of immune recruitment and ADCC against tumour cells that overexpress HER-2 protein, and/or downregulation of angiogenesis factors. In some aspects, the HER-2 targeting agent is a glycoengineered HER-2 antibody, e.g. TrasGex. In some aspects, the HER-2 targeting agent is a bispecific HER-2 antibody, e.g. Herceptarg. The term "anti-HER-2 antibody" or "antibody binding to human HER-2" or "antibody that specifically binds to human HER-2" or "antagonistic anti-HER2" refers to an antibody specifically binding to the human HER-2. The antibody may bind the human HER-2 antigen with a binding affinity of Kd-value of <10 nM, <5 nM, <2 nM, <1 nM, <0.5 nM, or lower. The binding affinity can be determined with a standard binding assay, such as surface plasmon resonance technique (BIAcore®, GE-Healthcare Uppsala, Sweden).

Preparation of Bispecific Antibodies for Use in the Invention

In certain aspects, the therapeutic agents used in the combination comprise multispecific antibodies, e.g. bispecific antibodies. Multispecific antibodies are monoclonal antibodies that have binding specificities for at least two different sites. In certain aspects, the binding specificities are for different antigens. In certain aspects, the binding specificities are for different epitopes on the same antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking of two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tuft et al. J. Immunol. 147: 60 (1991).

Engineered antibodies with three or more functional antigen binding sites, including "Octopus antibodies," are also included herein (see, e.g. US 2006/0025576A1).

The antibodies or fragments herein also include a "Dual Acting FAb" or "DAF" comprising an antigen binding site that binds to two different antigens (see, US 2008/0069820, for example). "Crossmab" antibodies are also included herein (see e.g. WO 2009/080251, WO 2009/080252, WO2009/080253, or WO2009/080254).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain (VH) and a variable light chain (VL) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell.

As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species. In one aspect, the bispecific bispecific antibodies used in the invention are composed of a single polypeptide chain comprising two single chain FV fragments (scFV) fused to each other by a peptide linker.

Fc Domain Modifications Reducing Fc Receptor Binding and/or Effector Function

The Fc domain of the antigen binding molecules of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

The Fc domain confers favorable pharmacokinetic properties to the antigen binding molecules of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular aspects, the Fc domain of the antigen binding molecules of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In a particular aspect, the invention provides an antibody, wherein the Fc domain comprises one or more amino acid substitution that reduces binding to an Fc receptor, in particular towards Fcγ receptor.

In one aspect, the Fc domain of the antibody of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is an antibody according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or cell activating antibodies comprising an Fc domain for Fc receptors may be evaluated using cell lines known to express particular Fc receptors, such as human NK cells expressing FcγIIIa receptor.

Effector function of an Fc domain, or antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some aspects, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antibodies of the invention are able to bind C1q and hence have CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Fc Domain Modifications Promoting Heterodimerization

The bispecific antigen binding molecules of the invention comprise different antigen-binding sites, fused to one or the other of the two subunits of the Fc domain, thus the two subunits of the Fc domain may be comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc domain of the bispecific antigen binding molecules of the invention a modification promoting the association of the desired polypeptides.

Accordingly, in particular aspects the invention relates to the bispecific antigen binding molecule comprising (a) at least one antigen binding domain capable of specific binding to a tumor-associated antigen, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of said 4-1BBL or a fragment thereof, and (c) a Fc domain composed of a first and a second subunit capable of stable association, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect said modification is a so-called "knob-into-hole" modification, comprising a "knob" modification in one of the two subunits of the Fc domain and a "hole" modification in the other one of the two subunits of the Fc domain. Thus, the invention relates to an antigen binding molecule comprising (a) at least one antigen binding domain capable of specific binding to a tumor-associated antigen, (b) a first and a second polypeptide that are linked to each other by a disulfide bond,
wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and (c) a Fc domain composed of a first and a second subunit capable of stable association, wherein the first subunit of the Fc domain comprises knobs and the second subunit of the Fc domain comprises holes according to the knobs into holes method. In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

The knob-into-hole technology is described e.g. in U.S. Pat. Nos. 5,731,168, 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc domain of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A).

In yet a further aspect, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter (2001), J Immunol Methods 248, 7-15). In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

The C-terminus of the heavy chain of the bispecific antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, a bispecific antibody comprising a heavy chain including a C-terminal CH3 domain as specified herein, comprises the C-terminal glycine-lysine dipeptide (G446 and K447, numbering according to Kabat EU index). In one embodiment of all aspects as reported herein, a bispecific antibody comprising a heavy chain including a C-terminal CH3 domain, as specified herein, comprises a C-terminal glycine residue (G446, numbering according to Kabat EU index).

Modifications in the Fab Domains

In one aspect, the invention relates to a 4-1BBL-containing antigen binding molecule, comprising (a) a Fab fragment capable of specific binding to a tumor-associated antigen, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and (c) a Fc domain composed of a first and a second subunit capable of stable association, wherein in one of the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In one aspect, the invention relates to a bispecific antigen binding molecule comprising (a) a first Fab fragment capable of specific binding to a tumor associated antigen, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and wherein each of them is linked to a CH1 or CL domain, and (c) a Fc domain composed of a first and a second subunit capable of stable association, wherein the constant domains CL and CH1 adjacent to 4-1BBL are replaced by each other so that the CH1 domain is part of the light chain and the CL domain is part of the heavy chain.

In another aspect, the invention relates to a bispecific antigen binding molecule, comprising (a) two light chains and two heavy chains of an antibody comprising two Fab fragments capable of specific binding to 4-1BB and the Fc domain, and (b) two additional Fab fragments capable of specific binding to a tumor associated antigen, wherein said additional Fab fragments are each connected via a peptide linker to the C-terminus of the heavy chains of (a). In a particular aspect, the additional Fab fragments are Fab fragments, wherein the variable domains VL and VH are replaced by each other so that the VH domain is part of the light chain and the VL domain is part of the heavy chain.

In another aspect, and to further improve correct pairing, the bispecific antigen binding molecule comprising (a) a first Fab fragment capable of specific binding to a tumor associated antigen, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and wherein each of them is linked to a CH1 or CL domain, and (c) a Fc domain composed of a first and a second subunit capable of stable association, can contain different charged amino acid substitutions (so-called "charged residues"). These modifications are introduced in the crossed or non-crossed CH1 and CL domains. In a particular aspect, the invention relates to a bispecific antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E).

More particularly, the invention relates to a bispecific binding molecule comprising a Fab, wherein in the CL domain adjacent to 4-1BBL the amino acid at position 123 (EU numbering) has been replaced by arginine (R) and the amino acid at position 124 (EU numbering) has been substituted by lysine (K), and wherein in the CH1 domain adjacent to 4-1BBL the amino acids at position 147 (EU numbering) and at position 213 (EU numbering) have been substituted by glutamic acid (E).

Polynucleotides

The invention further provides isolated polynucleotides encoding an antibody as described herein or a fragment thereof.

The isolated polynucleotides encoding the antibodies of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated polynucleotide encodes the entire antibody according to the invention as described herein. In other embodiments, the isolated polynucleotide encodes a polypeptide comprised in the antibody according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Bispecific antibodies as used in the invention may be obtained, for example, by solid-state peptide synthesis (e.g. Merrifield solid phase synthesis) or recombinant production. For recombinant production one or more polynucleotide encoding the antibody or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the antibody (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the antibody or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody or polypeptide fragments thereof is desired, DNA encoding a signal sequence may be placed upstream of the nucleic acid an antibody of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding an antibody of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) an antibody of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr− CHO cells (Urlaub et al., Proc Natl Acad Sci USA 77, 4216 (1980)); and myeloma cell lines such as Y0, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing an antibody of the invention or polypeptide fragments thereof is provided, wherein the method comprises culturing a host cell comprising polynucleotides encoding the antibody of the invention or polypeptide fragments thereof, as provided herein, under conditions suitable for expression of the antibody of the invention or polypeptide fragments thereof, and recovering the antibody of the invention or polypeptide fragments thereof from the host cell (or host cell culture medium).

In certain embodiments the moieties capable of specific binding to a target cell antigen (e.g. Fab fragments) forming part of the antigen binding molecule comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005)

(describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, NJ, 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the antibodies are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, NJ). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch. 14 (Cold Spring Harbor Laboratory, Cold Spring Harbor, NY).

Antibodies of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the antigen binding molecule or fragments thereof can be determined by any of a variety of well-known analytical methods including gel electrophoresis, high pressure liquid chromatography, and the like. For example, the 4-1BBL-containing antigen binding molecules expressed as described in the Examples were shown to be intact and properly assembled as demonstrated by reducing and non-reducing SDS-PAGE.

Assays

The antigen binding molecules provided herein may be identified, screened for, or characterized for their physical/chemical properties and/or biological activities by various assays known in the art.

1. Affinity Assays

The affinity of the bispecific antigen binding molecules provided herein for the corresponding receptor can be determined in accordance with the methods set forth in the Examples by surface plasmon resonance (SPR), using standard instrumentation such as a BIAcore instrument (GE Healthcare), and receptors or target proteins such as may be obtained by recombinant expression. The affinity of the bispecific antigen binding molecule for the target cell antigen can also be determined by surface plasmon resonance (SPR), using standard instrumentation such as a BIAcore instrument (GE Healthcare), and receptors or target proteins such as may be obtained by recombinant expression. For the FAP-4-1BBL antigen binding molecules the methods have been described in more detail in International Patent Appl. Publ. No. WO 2016/075278 A1. According to one aspect, $K_D$ is measured by surface plasmon resonance using a BIACORE® T100 machine (GE Healthcare) at 25° C.

2. Binding Assays and Other Assays

In one aspect, the FAP-4-1BBL antigen binding molecules as reported herein are tested for its antigen binding activity as described in more detail in International Patent Appl. Publ. No. WO 2016/075278 A1.

3. Activity Assays

In one aspect, assays are provided for identifying the biological activity of FAP-4-1BBL antigen binding molecules.

In certain embodiments, an antibody as reported herein is tested for such biological activity in in vitro co-culture assays with human immune effector cells.

Pharmaceutical Compositions, Formulations and Routes of Administration

In a further aspect, the invention provides pharmaceutical compositions comprising the 4-1BB agonists provided herein and a HER-2 targeting therapy or agent provided herein, e.g., for use in any of the below therapeutic methods.

In some aspects, the HER-2 targeting agent comprises a HER-2 antibody, a bispecific HER-2 antibody and/or a HER-2 antibody drug conjugate. In some aspects, the HER-2 targeting agent comprises trastuzumab, pertuzumab, and/or trastuzumab emtansine. In some aspects, the HER-2 targeting agent is trastuzumab, pertuzumab, and/or trastuzumab emtansine. In some aspects, the HER-2 targeting agent is selected from the group consisting of trastuzumab, pertuzumab, and trastuzumab emtansine. In some aspects, the HER-2 targeting agent comprises a combination of trastuzumab, pertuzumab, and/or trastuzumab emtansine. In some aspects, the HER-2 targeting agent comprises a HER-2 antibody selected from the group consisting of trastuzumab, pertuzumab and margetuximab. In one aspect, the HER-2 targeting agent is trastuzumab or pertuzumab. More particularly, the HER-2 targeting agent is trastuzumab. In some aspects, the HER-2 targeting is a glycoengineered HER-2 antibody, e.g. TrasGex. In some aspects, the HER-2 targeting agent is a bispecific HER-2 antibody, e.g. Herceptarg. In some aspects, the HER-2 targeting agent is a HER-2 antibody drug conjugate, in particular trastuzmab emtansine (ado-trastuzumab emtansine).

In some aspects, a pharmaceutical composition comprises a 4-1BB agonist provided herein and at least one pharmaceutically acceptable excipient. In other embodiments, a pharmaceutical composition comprises a 4-1BB agonist provided herein and at least one additional therapeutic agent, e.g., as described below. In some embodiments, there is provided a pharmaceutical composition comprising a HER-2 targeting agent and at least one pharmaceutically acceptable excipient.

Pharmaceutical compositions of the present invention comprise a therapeutically effective amount of one or more antibodies or agents dissolved or dispersed in a pharmaceutically acceptable excipient, carrier, adjuvant or diluent. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one antibody and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the antigen binding molecules may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antibodies of the invention may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

Administration of the 4-1BB Agonist and the HER-2 Targeting Therapy

Both the 4-1BB agonist and the HER-2 targeting therapy/agent (both called substance herein) can be administered by any suitable means, including parenteral, intrapulmonary, and intranasal, and, if desired for local treatment, intralesional administration. The methods of the present invention are particularly useful, however, in relation to therapeutic agents administered by parenteral, particularly intravenous, infusion. In some aspects, the HER-2 targeting agent comprises a HER-2 antibody, a bispecific HER-2 antibody and/or a HER-2 antibody drug conjugate. In some aspects, the HER-2 targeting agent comprises trastuzumab, pertuzumab, and/or trastuzumab emtansine. In some aspects, the HER-2 targeting agent is trastuzumab, pertuzumab, and/or trastuzumab emtansine. In some aspects, the HER-2 targeting agent is selected from the group consisting of trastuzumab, pertuzumab, and trastuzumab emtansine. In some aspects, the HER-2 targeting agent comprises a combination of trastuzumab, pertuzumab, and/or trastuzumab emtansine. In some aspects, the HER-2 targeting agent comprises a HER-2 antibody selected from the group consisting of trastuzumab, pertuzumab and margetuximab. In one aspect, the HER-2 targeting agent is trastuzumab or pertuzumab. More particularly, the HER-2 targeting agent is trastuzumab. In some aspects, the HER-2 targeting is a glycoengineered HER-2 antibody, e.g. TrasGex. In some aspects, the HER-2 targeting agent is a bispecific HER-2 antibody, e.g. Herceptarg. In some aspects, the HER-2 targeting agent is a HER-2 antibody drug conjugate, in particular trastuzmab emtansine (ado-trastuzumab emtansine).

Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein. In one embodiment, the therapeutic agent is administered parenterally, particularly intravenously. In a particular embodiment, the therapeutic agent is administered by intravenous infusion.

In some aspects, the 4-1BB agonist and the HER-2 targeting agent are administered together in a single composition. In some embodiments, the 4-1BB agonist and the HER-2 targeting agent are administered separately in two or more different compositions.

Both the 4-1BB agonist and the HER-2 targeting therapy/agent would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. Both the 4-1BB agonist and the HER-2 targeting therapy/agent need not be, but are optionally formulated with one or more agents currently used to prevent or treat the disorder in question. The effective amount of such other agents depends on the amount of therapeutic agent present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of the 4-1BB agonist and the HER-2 targeting therapy/agent (when used in their combination or with one or more other additional therapeutic agents) will depend on the type of disease to be treated, the type of 4-1BB agent, the severity and course of the disease, whether both agents are administered for preventive or therapeutic purposes, previous therapy, the patient's clinical history and response to the therapeutic agent, and the discretion of the attending physician. Each substance is suitably administered to the patient at one time or over a series of treatments. Depending on the type and severity of the disease, about 1 µg/kg to 15 mg/kg (e.g. 0.1 mg/kg-10 mg/kg) of the substance can be an initial candidate dosage for administration to the subject, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of each substance would be in the range from about 0.05 mg/kg to about 10 mg/kg. Thus, one or more doses of about 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg or 10 mg/kg (or any combination thereof) may be administered to the subject. Such doses may be administered intermittently, e.g. every week, every two weeks, or every three weeks (e.g. such that the subject receives from about two to about twenty, or e.g. about six doses of the therapeutic agent). An initial higher loading dose, followed by one or more lower doses, or an initial lower dose, followed by one or more higher doses may be administered. An exemplary dosing regimen comprises administering an initial dose of about 10 mg, followed by a bi-weekly dose of about 20 mg of the therapeutic agent. However, other dosage regimens may be useful. The progress of this therapy is easily monitored by conventional techniques and assays.

In one aspect, the administration of both the 4-1BB agonist and the HER-2 targeting therapy/agent is a single administration. In some embodiments, the 4-1BB agonist and the HER-2 targeting therapy/agent are administered simultaneously. The term "simultaneously" means at the same time or within a short period of time, usually less than 1 hour. In certain aspects, the administration of the therapeutic agent is two or more administrations. A drug that is administered "concurrently" with one or more other drugs is administered during the same treatment cycle, on the same day of treatment as the one or more other drugs, and, optionally, at the same time as the one or more other drugs. For instance, for therapies given every 3 weeks, the concurrently administered drugs are each administered on day-1 of a 3-week cycle. In one particular aspect, the substances are administered every week, every two weeks, or every three weeks, particularly every two weeks. In one aspect, the substance is administered in a therapeutically effective amount. In one aspect the substance is administered at a dose of about 50 µg/kg, about 100 µg/kg, about 200 µg/kg, about 300 µg/kg, about 400 µg/kg, about 500 µg/kg, about 600 µg/kg, about 700 µg/kg, about 800 µg/kg, about 900 µg/kg or about 1000 µg/kg. In one embodiment, the 4-1BB agonist is administered at a dose which is higher than the dose of the 4-1BB agonist in a corresponding treatment regimen without the administration of the Her-2 targeting therapy/agent. In one embodiment, the HER-2 targeting therapy/agent is administered at a dose which is higher than the dose of the HER-2 targeting therapy/agent in a corresponding treatment regimen without the administration of the 4-1BB agonist. In one aspect, the administration of the 4-1BB agonist comprises an initial administration of a first dose of the 4-1BB agonist, and one or more subsequent administrations of a second dose of the 4-1BB agonist, wherein the second dose is higher than the first dose. In one aspect, the administration of the 4-1BB agonist comprises an initial administration of a first dose of the 4-1BB agonist and one or more subsequent administrations of a second dose of the 4-1BB agonist wherein the first dose is not lower than the second dose.

When both therapeutic agents are co-administered sequentially the agents are administered in two separate administrations that are separated by a "specific period of time". The term specific period of time is meant anywhere from 1 hour to 15 days. For example, one of the agents can be administered within about 1, 2, 3, 4, 5, 6 or 7 days or 1 to 24 hours from the administration of the other agent, and, in one embodiment, the specific period time is 1 to 3 days, or 2 to 8 hours.

In one aspect, the 4-1BB agonist is administered prior to the administration of the HER-2 targeting therapy/agent. In another aspect, the HER-2 targeting therapy/agent is administered prior to the administration of the 4-1BB agonist.

In some aspects, the initial pharmaceutically effective amount of trastuzumab emtansine administered per dose will be in the range of about 0.3 to 15 mg/kg/day of patient body weight. A commercial T-DM1 formulation (KADCYLA®, ado-trastuzumab emtansine) is a sterile, white to off-white preservative free lyophilized powder in single-use vials. Each vial contains 100 mg or 160 mg ado-trastuzumab emtansine. Following reconstitution, each single use vial contains ado-trastuzumab emtansine (20 mg/mL), polysorbate 20 [0.02% (w/v)], sodium succinate (10 mM), and sucrose [6%>(w/v)] with a pH of 5.0 and density of 1.026 g/mL. The resulting solution containing 20 mg/mL ado-trastuzumab emtansine is administered by intravenous infusion following dilution.

A commercial formulation of pertuzumab (PERJETA®) contains pertuzumab 420 mg/14 mL (30 mg/mL) in the form of a preservative-free solution for IV infusion, and may be administered in a fixed dose of approximately 420 mg (equivalent to doses of 6 mg/kg for a 70-kg subject), approximately 525 mg, approximately 840 mg, and/or approximately 1050 mg. Treatment may start with a higher loading dose (e.g. 840 mg, equivalent to 12 mg/kg of body weight). A suitable pertuzumab formulation for therapeutic use comprises 30 mg/mL pertuzumab in 20 mM histidine acetate, 120 mM sucrose, 0.02% polysorbate 20, at pH 6.0. An alternate pertuzumab formulation comprises 25 mg/mL pertuzumab, 10 mM histidine-HCl buffer, 240 mM sucrose, 0.02% polysorbate 20, pH 6.0.

In another aspect, the 4-1BB agonist is for use with the HER-2 targeting therapy/agent, wherein a pretreatment with a Type II anti-CD20 antibody, preferably obinutuzumab, is performed prior to the combination treatment, wherein the period of time between the pretreatment and the combination treatment is sufficient for the reduction of B-cells in the individual in response to the Type II anti-CD20 antibody, preferably obinutuzumab.

Activation of T cells can lead to severe cytokine release syndrome (CRS). In a phase 1 study conducted by TeGenero (Suntharalingam et al., N Engl J Med (2006) 355, 1018-1028), all 6 healthy volunteers experienced near fatal, severe cytokine release syndrome (CRS) rapidly post-infusion of an inappropriately-dosed, T-cell stimulating super-agonist anti-CD28 monoclonal antibody. The cytokine release associated with administration of a T-cell activating therapeutic agent, such as the 4-1BB agonists described herein, to a subject can be significantly reduced by pre-treatment of said subject with a Type II anti-CD20 antibody, such as obinutuzumab. The use of GAZYVA® pre-treatment (Gpt) should aid in the rapid depletion of B cells, both in the peripheral blood and in secondary lymphoid organs, such that the risk of highly relevant adverse events (AEs) from strong systemic T cell activation by T-cell activating therapeutic agents (e.g. CRS) is reduced, while supporting exposure levels of T-cell activating therapeutic agents that are high enough from the start of dosing to mediate tumour cell elimination. To date, the safety profile of obinutuzumab (including cytokine release) has been assessed and managed in hundreds of patients in ongoing obinutuzumab clinical trials. Finally, in addition to supporting the safety profile of T-cell activating antibodies, Gpt should also help prevent the formation of anti-drug antibodies (ADAs) to these unique molecules.

In the present invention, the combination of the 4-1BB agonist and the HER-2 targeting therapy/agent can be used in combination with further agents in a therapy. For instance, at least one additional therapeutic agent may be co-administered. In certain aspects, an additional therapeutic agent is an immunotherapeutic agent. In some embodiments, the additional therapeutic agent is a chemotherapeutic agent. Suitable chemotherapeutic agents include one or more: anthracycline drugs, such as doxorubicin and epirubicin (Pharmorubicin®); taxane drugs, such as paclitaxel (Taxol®) and docetaxel (Taxotere®); fluorouracil (5FU); cyclophosphamide; methotrexate; cisplatin; and capecitabine. Other additional therapeutic agents include the kinase inhibitors lapatinib (Tykerb) and neratinib (Nerlynx).

Such combination therapies noted above encompass combined administration (where two or more therapeutic agents are included in the same or separate formulations), and separate administration, in which case, administration of the therapeutic agent can occur prior to, simultaneously, and/or following, administration of an additional therapeutic agent or agents. In one embodiment, administration of the therapeutic agent and administration of an additional therapeutic agent occur within about one month, or within about one, two or three weeks, or within about one, two, three, four, five, or six days, of each other.

Therapeutic Methods and Compositions

In one aspect, provided is a method for treating or delaying progression of cancer in an individual comprising administering to the subject an effective amount of a 4-1BB agonist described herein and an effective amount of a HER-2 targeting agent described herein. In various aspects, the HER-2 targeting agent comprises a HER-2 antibody, a bispecific HER-2 antibody and/or a HER-2 antibody drug conjugate. In some aspects, the HER-2 targeting agent comprises trastuzumab, pertuzumab, and/or trastuzumab emtansine. In some aspects, the HER-2 targeting agent is trastuzumab, pertuzumab, and/or trastuzumab emtansine. In some aspects, the HER-2 targeting agent is selected from the group consisting of trastuzumab, pertuzumab, and trastuzumab emtansine. In some aspects, the HER-2 targeting agent comprises a combination of trastuzumab, pertuzumab, and/or trastuzumab emtansine. In some aspects, the HER-2 targeting agent comprises a HER-2 antibody selected from the group consisting of trastuzumab, pertuzumab and margetuximab. In one aspect, the HER-2 targeting agent is trastuzumab or pertuzumab. More particularly, the HER-2 targeting agent is trastuzumab. In some aspects, the HER-2 targeting is a glycoengineered HER-2 antibody, e.g. TrasGex. In some aspects, the HER-2 targeting agent is a bispecific HER-2 antibody, e.g. Herceptarg. In some aspects, the HER-2 targeting agent is a HER-2 antibody drug conjugate, in particular trastuzmab emtansine (ado-trastuzumab emtansine).

In one such aspect, the method further comprises administering to the individual an effective amount of at least one additional therapeutic agent. Suitable additional agents include one or more: anthracycline drugs, such as doxorubicin and epirubicin (Pharmorubicin®); taxane drugs, such as paclitaxel (Taxol®) and docetaxel (Taxotere®); fluorouracil (5FU); cyclophosphamide; methotrexate; cisplatin; and capecitabine. Other suitable additional therapeutic agents include the kinase inhibitors lapatinib (Tykerb) and neratinib (Nerlynx). In further embodiments, herein is provided a method for tumor shrinkage comprising administering to the subject an effective amount of a 4-1BB agonist and a HER-2 targeting agent, as described herein. An "individual" or a "subject" according to any of the above aspects is preferably a human.

In one aspect, the invention provides a 4-1BB agonist for use in a method for treating or delaying progression of cancer, wherein the 4-1BB agonist is used in combination with a HER-2 targeting agent. In another aspect, the invention provides a 4-1BB agonist and a HER-2 targeting agent for use in a method for treating or delaying progression of cancer. In some embodiments, the 4-1BB agonist and/or the HER-2 targeting agent are combined with an additional therapeutic agent.

In further aspects, a composition for use in cancer immunotherapy is provided comprising a 4-1BB agonist and a HER-2 targeting agent. In certain embodiments, a composition comprising a 4-1BB agonist and a HER-2 targeting agent for use in a method of cancer immunotherapy is provided.

In a further aspect, herein is provided for the use of a composition comprising a 4-1BB agonist and a HER-2 targeting agent in the manufacture or preparation of a medicament. In some embodiments, the medicament is for treatment of cancer. In some embodiments, the medicament is for treatment of solid tumors. In some embodiments, the medicament is for use in a method of tumor shrinkage comprising administering to an individual having a solid tumor an effective amount of the medicament. In one such embodiment, the method further comprises administering to the individual an effective amount of at least one additional therapeutic agent. In some embodiments, the medicament is for treating solid tumors.

In particular aspects, the individual has HER-2 positive cancer. In some embodiments, the cancer may comprise cells overexpressing HER-2. In some embodiments, the cancer comprises a solid tumor. In some embodiments, the solid tumor is an advanced and/or metastatic solid tumor. In some aspects, HER-2 positive cancer is breast cancer, ovarian cancer, stomach cancer, gastric cancer, oesophageal cancer, lung cancer e.g. adenocarcinoma of the lung or non-small-cell lung cancer (NSCLC), uterine cancer e.g. uterine serous endometrial carcinoma, salivary duct carcinoma, bladder cancer, endometrial cancer, pancreatic cancer, colon cancer, prostate cancer, and/or head and neck cancer. In some aspects, the breast cancer is a breast carcinoma or a breast adenocarcinoma. In some aspects, the breast carcinoma is an invasive ductal carcinoma. In some aspects, the lung cancer is a lung adenocarcinoma. In some embodiments, the colon cancer is a colorectal adenocarcinoma. An "individual" according to any of the above embodiments may be a human.

In some aspects, the cancer is HER-2 positive breast cancer, in particular metastatic breast cancer (stage IV breast cancer). In some aspects, the cancer is a Stage II or III HER-2 positive breast cancer. In some aspects, the cancer is a HER-2 positive early breast cancer. In some aspects, the cancer is HER-2 positive gastric cancer.

The treatment may be aimed at prevention of the development or progression of a cancer. As such, subjects may be prophylactically treated against development of a disease state using the 4-1BB agonists and HER-2 targeting agents described herein. This may take place before the onset of symptoms of the disease state, and/or may be given to subjects considered to be at greater risk of development or progression of cancer.

In some embodiments, the 4-1BB agonist acts synergistically with the HER-2 targeting agent.

The combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one embodiment, administration of a 4-1BB agonist and a HER-2 targeting agent and optionally the administration of an additional therapeutic agent occur within about one month, or within about one, two or three weeks, or within about one, two, three, four, five, or six days, of each other.

Both the 4-1BB agonist and the HER-2 targeting agent as described herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Both the 4-1BB agonist and the HER-2 targeting agent as described herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibodies need not be, but are optionally formulated with one or more agents currently used to prevent or treat the disorder in question. The effective amount of such other agents depends on the amount of antibodies present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

Articles of Manufacture (Kits)

In another aspect of the invention, a kit containing materials useful for the treatment, prevention and/or diagnosis of the disorders described above is provided. The kit comprises at least one container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least two active agents in the kit are a 4-1BB agonist and a HER-2 targeting agent of the invention. In some aspects, the HER-2 targeting agent comprises a HER-2 antibody, a bispecific HER-2 antibody and/or a HER-2 antibody drug conjugate. In some aspects, the HER-2 targeting agent comprises trastuzumab, pertuzumab, and/or trastuzumab emtansine. In some aspects, the HER-2 targeting agent is trastuzumab, pertuzumab, and/or trastuzumab emtansine. In some aspects, the HER-2 targeting agent is selected from the group consisting of trastuzumab, pertuzumab, and trastuzumab emtansine. In some aspects, the HER-2 targeting agent comprises a combination of trastuzumab, pertuzumab, and/or trastuzumab emtansine. In some aspects, the HER-2 targeting agent comprises a HER-2 antibody selected from the group consisting of trastuzumab, pertuzumab and margetuximab. In one aspect, the HER-2 targeting agent is trastuzumab or pertuzumab. More particularly, the HER-2 targeting agent is trastuzumab. In some aspects, the HER-2 targeting is a glycoengineered HER-2 antibody, e.g. TrasGex. In some aspects, the HER-2 targeting agent is a bispecific HER-2 antibody, e.g. Herceptarg. In some aspects, the HER-2 targeting agent is a HER-2 antibody drug conjugate, in particular trastuzmab emtansine (ado-trastuzumab emtansine).

In a particular aspect, provided is a kit for treating or delaying progression of cancer in a subject, comprising a package comprising (A) a first composition comprising as active ingredient a 4-1BB agonist and a pharmaceutically acceptable carrier; (B) a second composition comprising as active ingredient a HER-2 targeting agent and a pharmaceutically acceptable carrier, and (C) instructions for using the compositions in a combination therapy.

The label or package insert indicates how the composition is used for treating the condition of choice and provides the instructions for using the compositions in a combination therapy. Moreover, the kit may comprise (a) a first container with a composition contained therein, wherein the composition comprises a 4-1BB agonist of the invention; and (b) a second container with a composition contained therein, wherein the composition comprises a HER-2 targeting agent of the invention. In addition, the kit may comprise one or more further containers comprising further active ingredients that can be used in combination. The article of manufacture in this embodiment of the invention may further comprise a package insert indicating that the compositions can be used to treat a particular condition.

Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE C (Sequences):

| SEQ ID NO: | Name | Sequence |
|---|---|---|
| 1 | Human (hu) 4-1BBL (71-254) | REGPELSPDDPAGLLDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGLPSPRSE |
| 2 | hu 4-1BBL (85-254) | LDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGLPSPRSE |
| 3 | hu 4-1BBL (80-254) | DPAGLLDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGLPSPRSE |
| 4 | hu 4-1BBL (52-254) | PWAVSGARASPGSAASPRLREGPELSPDDPAGLLDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGLPSPRSE |
| 5 | Human (hu) 4-1BBL (71-248) | REGPELSPDDPAGLLDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGL |
| 6 | hu 4-1BBL (85-248) | LDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGL |
| 7 | hu 4-1BBL (80-248) | DPAGLLDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGL |
| 8 | hu 4-1BBL (52-248) | PWAVSGARASPGSAASPRLREGPELSPDDPAGLLDLRQGMFAQLVAQNVLLIDGPLSWYSDPGLAGVSLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPEIPAGL |
| 9 | FAP (28H1) CDR-H1 | SHAMS |
| 10 | FAP (28H1) CDR-H2 | AIWASGEQYYADSVKG |
| 11 | FAP (28H1) CDR-H3 | GWLGNFDY |
| 12 | FAP (28H1) CDR-L1 | RASQSVSRSYLA |
| 13 | FAP (28H1) CDR-L2 | GASTRAT |
| 14 | FAP (28H1) CDR-L3 | QQGQVIPPT |
| 15 | FAP(4B9) CDR-H1 | SYAMS |
| 16 | FAP(4B9) CDR-H2 | AIIGSGASTYYADSVKG |
| 17 | FAP(4B9) CDR-H3 | GWFGGFNY |

TABLE C-continued (Sequences):

| SEQ ID NO: | Name | Sequence |
|---|---|---|
| 18 | FAP(4B9) CDR-L1 | RASQSVTSSYLA |
| 19 | FAP(4B9) CDR-L2 | VGSRRAT |
| 20 | FAP(4B9) CDR-L3 | QQGIMLPPT |
| 21 | FAP(28H1) VH | EVQLLESGGGLVQPGGSLRLSCAASGFTFSSHA<br>MSWVRQAPGKGLEWVSAIWASGEQYYADSV<br>KGRFTISRDNSKNTLYLQMNSLRAEDTAVYYC<br>AKGWLGNFDYWGQGTLVTVSS |
| 22 | FAP(28H1) VL | EIVLTQSPGTLSLSPGERATLSCRASQSVSRSYL<br>AWYQQKPGQAPRLLIIGASTRATGIPDRFSGSG<br>SGTDFTLTISRLEPEDFAVYYCQQGQVIPPTFGQ<br>GTKVEIK |
| 23 | FAP(4B9) VH | EVQLLESGGGLVQPGGSLRLSCAASGFTFSSYA<br>MSWVRQAPGKGLEWVSAIIGSGASTYYADSVK<br>GRFTISRDNSKNTLYLQMNSLRAEDTAVYYCA<br>KGWFGGFNYWGQGTLVTVSS |
| 24 | FAP(4B9) VL | EIVLTQSPGTLSLSPGERATLSCRASQSVTSSYL<br>AWYQQKPGQAPRLLINVGSRRATGIPDRFSGSG<br>SGTDFTLTISRLEPEDFAVYYCQQGIMLPPTFGQ<br>GTKVEIK |
| 25 | dimeric hu 4-1BBL (71-254) connected by (G4S)$_2$ linker | REGPELSPDDPAGLLDLRQGMFAQLVAQNVLL<br>IDGPLSWYSDPGLAGVSLTGGLSYKEDTKELV<br>VAKAGVYYVFFQLELRRVVAGEGSGSVSLALH<br>LQPLRSAAGAAALALTVDLPPASSEARNSAFGF<br>QGRLLHLSAGQRLGVHLHTEARARHAWQLTQ<br>GATVLGLFRVTPEIPAGLPSPRSEGGGGSGGGG<br>SREGPELSPDDPAGLLD LRQGMFAQLVAQNVL<br>LIDGPLSWYSDPGLAGVSLTGGLSYKEDTKELV<br>VAKAGVYYVFFQLELRRVVAGEGSGSVSLALH<br>LQPLRSAAGAAALALTVDLPPASSEARNSAFGF<br>QGRLLHLSAGQRLGVHLHTEARARHAWQLTQ<br>GATVLGLFRVTPEIPAGLPSPRSE |
| 26 | dimeric hu 4-1BBL (85-254) connected by (G4S)$_2$ linker | LDLRQGMFAQLVAQNVLLIDGPLSWYSDPGLA<br>GVSLTGGLSYKEDTKELVVAKAGVYYVFFQLE<br>LRRVVAGEGSGSVSLALHLQPLRSAAGAAALA<br>LTVDLPPASSEARNSAFGFQGRLLHLSAGQRLG<br>VHLHTEARARHAWQLTQGATVLGLFRVTPEIP<br>AGLPSPRSEGGGGSGGGGSLDLRQGMFAQLVA<br>QNVLLIDGPLSWYSDPGLAGVSLTGGLSYKED<br>TKELVVAKAGVYYVFFQLELRRVVAGEGSGSV<br>SLALHLQPLRSAAGAAALALTVDLPPASSEARN<br>SAFGFQGRLLHLSAGQRLGVHLHTEARARHA<br>WQLTQGATVLGLFRVTPEIPAGLPSPRSE |
| 27 | dimeric hu 4-1BBL (80-254) connected by (G4S)$_2$ linker | DPAGLLDLRQGMFAQLVAQNVLLIDGPLSWYS<br>DPGLAGVSLTGGLSYKEDTKELVVAKAGVYY<br>VFFQLELRRVVAGEGSGSVSLALHLQPLRSAA<br>GAAALALTVDLPPASSEARNSAFGFQGRLLHLS<br>AGQRLGVHLHTEARARHAWQLTQGATVLGLF<br>RVTPEIPAGLPSPRSEGGGGSGGGGSDPAGLLD<br>LRQGMFAQLVAQNVLLIDGPLSWYSDPGLAGV<br>SLTGGLSYKEDTKELVVAKAGVYYVFFQLELR<br>RVVAGEGSGSVSLALHLQPLRSAAGAAALALT<br>VDLPPASSEARNSAFGFQGRLLHLSAGQRLGV<br>HLHTEARARHAWQLTQGATVLGLFRVTPEIPA<br>GLPSPRSE |
| 28 | dimeric hu 4-1BBL (52-254) connected by (G4S)$_2$ linker | PWAVSGARASPGSAASPRLREGPELSPDDPAGL<br>LDLRQGMFAQLVAQNVLLIDGPLSWYSDPGLA<br>GVSLTGGLSYKEDTKELVVAKAGVYYVFFQLE<br>LRRVVAGEGSGSVSLALHLQPLRSAAGAAALA<br>LTVDLPPASSEARNSAFGFQGRLLHLSAGQRLG<br>VHLHTEARARHAWQLTQGATVLGLFRVTPEIP<br>AGLPSPRSEGGGGSGGGGSPWAVSGARASPGS<br>AASPRLREGPELSPDDPAGLLDLRQGMFAQLV<br>AQNVLLIDGPLSWYSDPGLAGVSLTGGLSYKE<br>DTKELVVAKAGVYYVFFQLELRRVVAGEGSGS |

TABLE C-continued (Sequences):

| SEQ ID NO: | Name | Sequence |
|---|---|---|
| | | VSLALHLQPLRSAAGAAALALTVDLPPASSEAR NSAFGFQGRLLHLSAGQRLGVHLHTEARARHA WQLTQGATVLGLFRVTPEIPAGLPSPRSE |
| 29 | dimeric hu 4-1BBL (71-248) connected by (G4S)2 linker | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFGF QGRLLHLSAGQRLGVHLHTEARARHAWQLTQ GATVLGLFRVTPEIPAGLGGGGSGGGGSREGPE LSPDDPAGLLDLRQGMFAQLVAQNVLLIDGPL SWYSDPGLAGVSLTGGLSYKEDTKELVVAKA GVYYVFFQLELRRVVAGEGSGSVSLALHLQPL RSAAGAAALALTVDLPPASSEARNSAFGFQGR LLHLSAGQRLGVHLHTEARARHAWQLTQGAT VLGLFRVTPEIPAGL |
| 30 | dimeric hu 4-1BBL (85-248) connected by (G4S)2 linker | LDLRQGMFAQLVAQNVLLIDGPLSWYSDPGLA GVSLTGGLSYKEDTKELVVAKAGVYYVFFQLE LRRVVAGEGSGSVSLALHLQPLRSAAGAAALA LTVDLPPASSEARNSAFGFQGRLLHLSAGQRLG VHLHTEARARHAWQLTQGATVLGLFRVTPEIP AGLGGGGSGGGGSLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFGF QGRLLHLSAGQRLGVHLHTEARARHAWQLTQ GATVLGLFRVTPEIPAGL |
| 31 | dimeric hu 4-1BBL (80-248) connected by (G4S)2 linker | DPAGLLDLRQGMFAQLVAQNVLLIDGPLSWYS DPGLAGVSLTGGLSYKEDTKELVVAKAGVYY VFFQLELRRVVAGEGSGSVSLALHLQPLRSAA GAAALALTVDLPPASSEARNSAFGFQGRLLHLS AGQRLGVHLHTEARARHAWQLTQGATVLGLF RVTPEIPAGLGGGGSGGGGSDPAGLLDLRQGM FAQLVAQNVLLIDGPLSWYSDPGLAGVSLTGG LSYKEDTKELVVAKAGVYYVFFQLELRRVVA GEGSGSVSLALHLQPLRSAAGAAALALTVDLP PASSEARNSAFGFQGRLLHLSAGQRLGVHLHT EARARHAWQLTQGATVLGLFRVTPEIPAGL |
| 32 | dimeric hu 4-1BBL (52-248) connected by (G4S)2 linker | PWAVSGARASPGSAASPRLREGPELSPDDPAGL LDLRQGMFAQLVAQNVLLIDGPLSWYSDPGLA GVSLTGGLSYKEDTKELVVAKAGVYYVFFQLE LRRVVAGEGSGSVSLALHLQPLRSAAGAAALA LTVDLPPASSEARNSAFGFQGRLLHLSAGQRLG VHLHTEARARHAWQLTQGATVLGLFRVTPEIP AGLGGGGSGGGGSPWAVSGARASPGSAASPRL REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFGF QGRLLHLSAGQRLGVHLHTEARARHAWQLTQ GATVLGLFRVTPEIPAGL |
| 33 | CEA-HCDR1 (CEACAM5) | DTYMH |
| 34 | CEA-HCDR2 (CEACAM5) | RIDPANGNSKYVPKFQG |
| 35 | CEA-HCDR3 (CEACAM5) | FGYYVSDYAMAY |
| 36 | CEA-LCDR1 (CEACAM5) | RAGESVDIFGVGFLH |
| 37 | CEA-LCDR2 (CEACAM5) | RASNRAT |
| 38 | CEA-LCDR3 (CEACAM5) | QQTNEDPYT |
| 39 | CEA VH (CEACAM5) | QVQLVQSGAEVKKPGSSVKVSCKASGFNIKDT YMHWVRQAPGQGLEWMGRIDPANGNSKYVP KFQGRVTITADTSTSTAYMELSSLRSEDTAVYY CAPFGYYVSDYAMAYWGQGTLVTVSS |

TABLE C-continued (Sequences):

| SEQ ID NO: | Name | Sequence |
|---|---|---|
| 40 | CEA VL (CEACAM5) | EIVLTQSPATLSLSPGERATLSCRAGESVDIFGV GFLHWYQQKPGQAPRLLIYRASNRATGIPARFS GSGSGTDFTLTISSLEPEDFAVYYCQQTNEDPY TFGQGTKLEIK |
| 41 | Dimeric hu 4-1BBL (71-248)- CL* Fc knob chain (Construct 2.4 and 5.4) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFGF QGRLLHLSAGQRLGVHLHTEARARHAWQLTQ GATVLGLFRVTPEIPAGLGGGGSGGGGSREGPE LSPDDPAGLLDLRQGMFAQLVAQNVLLIDGPL SWYSDPGLAGVSLTGGLSYKEDTKELVVAKA GVYYVFFQLELRRVVAGEGSGSVSLALHLQPL RSAAGAAALALTVDLPPASSEARNSAFGFQGR LLHLSAGQRLGVHLHTEARARHAWQLTQGAT VLGLFRVTPEIPAGLGGGGSGGGGSRTVAAPSV FIFPPSDRKLKSGTASVVCLLNNFYPREAKVQW KVDNALQSGNSQESVTEQDSKDSTYSLSSTLTL SKADYEKHKVYACEVTHQGLSSPVTKSFNRGE CDKTHTCPPCPAPEAAGGPSVFLFPPKPKDTLM ISRTPEVTCVVVDVSHEDPEVKFNWYVDGVEV HNAKTKPREEQYNSTYRVVSVLTVLHQDWLN GKEYKCKVSNKALGAPIEKTISKAKGQPREPQV YTLPPCRDELTKNQVSLWCLVKGFYPSDIAVE WESNGQPENNYKTTPPVLDSDGSFFLYSKLTV DKSRWQQGNVFSCSVMHEALHNHYTQKSLSL SPGK |
| 42 | Monomeric hu 4-1BBL (71-248)- CH1* (Construct 2.4 and 5.4) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFGF QGRLLHLSAGQRLGVHLHTEARARHAWQLTQ GATVLGLFRVTPEIPAGLGGGGSGGGGSASTK GPSVFPLAPSSKSTSGGTAALGCLVEDYFPEPV TVSWNSGALTSGVHTFPAVLQSSGLYSLSSVVT VPSSSLGTQTYICNVNHKPSNTKVDEKVEPKSC |
| 43 | anti-FAP (4B9) Fc hole chain (Construct 2.4) | EVQLLESGGGLVQPGGSLRLSCAASGFTFSSYA MSWVRQAPGKGLEWVSAIIGSGASTYYADSVK GRFTISRDNSKNTLYLQMNSLRAEDTAVYYCA KGWFGGFNYWGQGTLVTVSSASTKGPSVFPLA PSSKSTSGGTAALGCLVKDYFPEPVTVSWNSG ALTSGVHTFPAVLQSSGLYSLSSVVTVPSSSLGT QTYICNVNHKPSNTKVDKKVEPKSCDKTHTCP PCPAPEAAGGPSVFLFPPKPKDTLMISRTPEVTC VVVDVSHEDPEVKFNWYVDGVEVHNAKTKPR EEQYNSTYRVVSVLTVLHQDWLNGKEYKCKV SNKALGAPIEKTISKAKGQPREPQVCTLPPSRDE LTKNQVSLSCAVKGFYPSDIAVEWESNGQPEN NYKTTPPVLDSDGSFFLVSKLTVDKSRWQQGN VFSCSVMHEALHNHYTQKSLSLSPGK |
| 44 | anti-FAP (4B9) light chain (Construct 2.4) | EIVLTQSPGTLSLSPGERATLSCRASQSVTSSYL AWYQQKPGQAPRLLINVGSRRATGIPDRFSGSG SGTDFTLTISRLEPEDFAVYYCQQGIMLPPTFGQ GTKVEIKRTVAAPSVFIFPPSDEQLKSGTASVVC LLNNFYPREAKVQWKVDNALQSGNSQESVTE QDSKDSTYSLSSTLTLSKADYEKHKVYACEVT HQGLSSPVTKSFNRGEC |
| 45 | Dimeric hu 4-1BBL (71-254)- CL* Fc knob chain (Construct 1.2) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFGF QGRLLHLSAGQRLGVHLHTEARARHAWQLTQ GATVLGLFRVTPEIPAGLPSPRSEGGGGSGGGG SREGPELSPDDPAGLLDLRQGMFAQLVAQNVL LIDGPLSWYSDPGLAGVSLTGGLSYKEDTKELV VAKAGVYYVFFQLELRRVVAGEGSGSVSLALH LQPLRSAAGAAALALTVDLPPASSEARNSAFGF QGRLLHLSAGQRLGVHLHTEARARHAWQLTQ GATVLGLFRVTPEIPAGLPSPRSEGGGGSGGGG |

TABLE C-continued (Sequences):

| SEQ ID NO: | Name | Sequence |
|---|---|---|
| | | SRTVAAPSVFIFPPSDRKLKSGTASVVCLLNNF YPREAKVQWKVDNALQSGNSQESVTEQDSKD STYSLSSTLTLSKADYEKHKVYACEVTHQGLSS PVTKSFNRGECDKTHTCPPCPAPEAAGGPSVFL FPPKPKDTLMISRTPEVTCVVVDVSHEDPEVKF NWYVDGVEVHNAKTKPREEQYNSTYRVVSVL TVLHQDWLNGKEYKCKVSNKALGAPIEKTISK AKGQPREPQVYTLPPCRDELTKNQVSLWCLVK GFYPSDIAVEWESNGQPENNYKTTPPVLDSDGS FFLYSKLTVDKSRWQQGNVFSCSVMHEALHN HYTQKSLSLSPGK |
| 46 | Monomeric hu 4-1BBL (71-254)-CH1* (Construct 1.2) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFGF QGRLLHLSAGQRLGVHLHTEARARHAWQLTQ GATVLGLFRVTPEIPAGLPSPRSEGGGGSGGGG SASTKGPSVFPLAPSSKSTSGGTAALGCLVEDY FPEPVTVSWNSGALTSGVHTFPAVLQSSGLYSL SSVVTVPSSSLGTQTYICNVNHKPSNTKVDEKV EPKSC |
| 47 | anti-FAP(28H1) Fc hole chain | EVQLLESGGGLVQPGGSLRLSCAASGFTFSSHA MSWVRQAPGKGLEWVSAIWASGEQYYADSV KGRFTISRDNSKNTLYLQMNSLRAEDTAVYYC AKGWLGNFDYWGQGTLVTVSSASTKGPSVFPL APSSKSTSGGTAALGCLVKDYFPEPVTVSWNS GALTSGVHTFPAVLQSSGLYSLSSVVTVPSSSL GTQTYICNVNHKPSNTKVDKKVEPKSCDKTHT CPPCPAPEAAGGPSVFLFPPKPKDTLMISRTPEV TCVVVDVSHEDPEVKFNWYVDGVEVHNAKTK PREEQYNSTYRVVSVLTVLHQDWLNGKEYKC KVSNKALGAPIEKTISKAKGQPREPQVCTLPPS RDELTKNQVSLSCAVKGFYPSDIAVEWESNGQ PENNYKTTPPVLDSDGSFFLVSKLTVDKSRWQ QGNVFSCSVMHEALHNHYTQKSLSLSPGK |
| 48 | anti-FAP (28H1) light chain | EIVLTQSPGTLSLSPGERATLSCRASQSVSRSYL AWYQQKPGQAPRLLIIGASTRATGIPDRFSGSG SGTDFTLTISRLEPEDFAVYYCQQGQVIPPTFGQ GTKVEIKRTVAAPSVFIFPPSDEQLKSGTASVVC LLNNFYPREAKVQWKVDNALQSGNSQESVTE QDSKDSTYSLSSTLTLSKADYEKHKVYACEVT HQGLSSPVTKSFNRGEC |
| 49 | DP47 Fc hole chain | EVQLLESGGGLVQPGGSLRLSCAASGFTFSSYA MSWVRQAPGKGLEWVSAISGSGGSTYYADSV KGRFTISRDNSKNTLYLQMNSLRAEDTAVYYC AKGSGFDYWGQGTLVTVSSASTKGPSVFPLAP SSKSTSGGTAALGCLVKDYFPEPVTVSWNSGA LTSGVHTFPAVLQSSGLYSLSSVVTVPSSSLGTQ TYICNVNHKPSNTKVDKKVEPKSCDKTHTCPP CPAPEAAGGPSVFLFPPKPKDTLMISRTPEVTCV VVDVSHEDPEVKFNWYVDGVEVHNAKTKPRE EQYNSTYRVVSVLTVLHQDWLNGKEYKCKVS NKALGAPIEKTISKAKGQPREPQVCTLPPSRDEL TKNQVSLSCAVKGFYPSDIAVEWESNGQPENN YKTTPPVLDSDGSFFLVSKLTVDKSRWQQGNV FSCSVMHEALHNHYTQKSLSLSPGK |
| 50 | anti-FAP (4B9) Fc hole chain fused to dimeric hu 4-1BBL (71-254) | EVQLLESGGGLVQPGGSLRLSCAASGFTFSSYA MSWVRQAPGKGLEWVSAIIGSGASTYYADSVK GRFTISRDNSKNTLYLQMNSLRAEDTAVYYCA KGWFGGFNYWGQGTLVTVSSASTKGPSVFPLA PSSKSTSGGTAALGCLVKDYFPEPVTVSWNSG ALTSGVHTFPAVLQSSGLYSLSSVVTVPSSSLGT QTYICNVNHKPSNTKVDKKVEPKSCDKTHTCP PCPAPEAAGGPSVFLFPPKPKDTLMISRTPEVTC VVVDVSHEDPEVKFNWYVDGVEVHNAKTKPR EEQYNSTYRVVSVLTVLHQDWLNGKEYKCKV SNKALGAPIEKTISKAKGQPREPQVCTLPPSRDE LTKNQVSLSCAVKGFYPSDIAVEWESNGQPEN NYKTTPPVLDSDGSFFLVSKLTVDKSRWQQGN VFSCSVMHEALHNHYTQKSLSLSPGGGGSGG |

TABLE C-continued (Sequences):

| SEQ ID NO: | Name | Sequence |
|---|---|---|
| | | GGSREGPELSPDDPAGLLDLRQGMFAQLVAQN VLLIDGPLSWYSDPGLAGVSLTGGLSYKEDTKE LVVAKAGVYYVFFQLELRRVVAGEGSGSVSLA LHLQPLRSAAGAAALALTVDLPPASSEARNSAF GFQGRLLHLSAGQRLGVHLHTEARARHAWQL TQGATVLGLFRVTPEIPAGLPSPRSEGGGGSGG GGSREGPELSPDDPAGLLDLRQGMFAQLVAQN VLLIDGPLSWYSDPGLAGVSLTGGLSYKEDTKE LVVAKAGVYYVFFQLELRRVVAGEGSGSVSLA LHLQPLRSAAGAAALALTVDLPPASSEARNSAF GFQGRLLHLSAGQRLGVHLHTEARARHAWQL TQGATVLGLFRVTPEIPAGLPSPRSE |
| 51 | anti-FAP (4B9) Fc knob chain fused to monomeric hu 4-1BBL (71-254) | EVQLLESGGGLVQPGGSLRLSCAASGFTFSSYA MSWVRQAPGKGLEWVSAIIGSGASTYYADSVK GRFTISRDNSKNTLYLQMNSLRAEDTAVYYCA KGWFGGFNYWGQGTLVTVSSASTKGPSVFPLA PSSKSTSGGTAALGCLVKDYFPEPVTVSWNSG ALTSGVHTFPAVLQSSGLYSLSSVVTVPSSSLGT QTYICNVNHKPSNTKVDKKVEPKSCDKTHTCP PCPAPEAAGGPSVFLFPPKPKDTLMISRTPEVTC VVVDVSHEDPEVKFNWYVDGVEVHNAKTKPR EEQYNSTYRVVSVLTVLHQDWLNGKEYKCKV SNKALGAPIEKTISKAKGQPREPQVYTLPPCRD ELTKNQVSLWCLVKGFYPSDIAVEWESNGQPE NNYKTTPPVLDSDGSFFLYSKLTVDKSRWQQG NVFSCSVMHEALHNHYTQKSLSLSPGGGGGSG GGGSREGPELSPDDPAGLLDLRQGMFAQLVAQ NVLLIDGPLSWYSDPGLAGVSLTGGLSYKEDT KELVVAKAGVYYVFFQLELRRVVAGEGSGSVS LALHLQPLRSAAGAAALALTVDLPPASSEARNS AFGFQGRLLHLSAGQRLGVHLHTEARARHAW QLTQGATVLGLFRVTPEIPAGLPSPRSE |
| 52 | anti-FAP (28H1) Fc hole chain fused to dimeric hu 4-1BBL (71-254) | EVQLLESGGGLVQPGGSLRLSCAASGFTFSSHA MSWVRQAPGKGLEWVSAIWASGEQYYADSV KGRFTISRDNSKNTLYLQMNSLRAEDTAVYYC AKGWLGNFDYWGQGTLVTVSSASTKGPSVFPL APSSKSTSGGTAALGCLVKDYFPEPVTVSWNS GALTSGVHTFPAVLQSSGLYSLSSVVTVPSSSL GTQTYICNVNHKPSNTKVDKKVEPKSCDKTHT CPPCPAPEAAGGPSVFLFPPKPKDTLMISRTPEV TCVVVDVSHEDPEVKFNWYVDGVEVHNAKTK PREEQYNSTYRVVSVLTVLHQDWLNGKEYKC KVSNKALGAPIEKTISKAKGQPREPQVCTLPPS RDELTKNQVSLSCAVKGFYPSDIAVEWESNGQ PENNYKTTPPVLDSDGSFFLVSKLTVDKSRWQ QGNVFSCSVMHEALHNHYTQKSLSLSPGGGGG SGGGGSREGPELSPDDPAGLLDLRQGMFAQLV AQNVLLIDGPLSWYSDPGLAGVSLTGGLSYKE DTKELVVAKAGVYYVFFQLELRRVVAGEGSGS VSLALHLQPLRSAAGAAALALTVDLPPASSEAR NSAFGFQGRLLHLSAGQRLGVHLHTEARARHA WQLTQGATVLGLFRVTPEIPAGLPSPRSEGGGG SGGGGSREGPELSPDDPAGLLDLRQGMFAQLV AQNVLLIDGPLSWYSDPGLAGVSLTGGLSYKE DTKELVVAKAGVYYVFFQLELRRVVAGEGSGS VSLALHLQPLRSAAGAAALALTVDLPPASSEAR NSAFGFQGRLLHLSAGQRLGVHLHTEARARHA WQLTQGATVLGLFRVTPEIPAGLPSPRSE |
| 53 | anti-FAP (28H1) Fc knob chain fused to monomeric hu 4-1BBL (71-254) | EVQLLESGGGLVQPGGSLRLSCAASGFTFSSHA MSWVRQAPGKGLEWVSAIWASGEQYYADSV KGRFTISRDNSKNTLYLQMNSLRAEDTAVYYC AKGWLGNFDYWGQGTLVTVSSASTKGPSVFPL APSSKSTSGGTAALGCLVKDYFPEPVTVSWNS GALTSGVHTFPAVLQSSGLYSLSSVVTVPSSSL GTQTYICNVNHKPSNTKVDKKVEPKSCDKTHT CPPCPAPEAAGGPSVFLFPPKPKDTLMISRTPEV TCVVVDVSHEDPEVKFNWYVDGVEVHNAKTK PREEQYNSTYRVVSVLTVLHQDWLNGKEYKC KVSNKALGAPIEKTISKAKGQPREPQVYTLPPC RDELTKNQVSLWCLVKGFYPSDIAVEWESNGQ PENNYKTTPPVLDSDGSFFLYSKLTVDKSRWQ QGNVFSCSVMHEALHNHYTQKSLSLSPGGGGG |

TABLE C-continued (Sequences):

| SEQ ID NO: | Name | Sequence |
|---|---|---|
| | | SGGGGSREGPELSPDDPAGLLDLRQGMFAQLV AQNVLLIDGPLSWYSDPGLAGVSLTGGLSYKE DTKELVVAKAGVYYVFFQLELRRVVAGEGSGS VSLALHLQPLRSAAGAAALALTVDLPPASSEAR NSAFGFQGRLLHLSAGQRLGVHLHTEARARHA WQLTQGATVLGLFRVTPEIPAGLPSPRSE |
| 54 | DP47 Fc hole chain fused to dimeric hu 4-1BBL (71-254) | EVQLLESGGGLVQPGGSLRLSCAASGFTFSSYA MSWVRQAPGKGLEWVSAIIGSGASTYYADSVK GRFTISRDNSKNTLYLQMNSLRAEDTAVYYCA KGWFGGFNYWGQGTLVTVSSASTKGPSVFPLA PSSKSTSGGTAALGCLVKDYFPEPVTVSWNSG ALTSGVHTFPAVLQSSGLYSLSSVVTVPSSSLGT QTYICNVNHKPSNTKVDKKVEPKSCDKTHTCP PCPAPEAAGGPSVFLFPPKPKDTLMISRTPEVTC VVVDVSHEDPEVKFNWYVDGVEVHNAKTKPR EEQYNSTYRVVSVLTVLHQDWLNGKEYKCKV SNKALGAPIEKTISKAKGQPREPQVCTLPPSRDE LTKNQVSLSCAVKGFYPSDIAVEWESNGQPEN NYKTTPPVLDSDGSFFLVSKLTVDKSRWQQGN VFSCSVMHEALHNHYTQKSLSLSPGGGGGSGG GGSREGPELSPDDPAGLLDLRQGMFAQLVAQN VLLIDGPLSWYSDPGLAGVSLTGGLSYKEDTKE LVVAKAGVYYVFFQLELRRVVAGEGSGSVSLA LHLQPLRSAAGAAALALTVDLPPASSEARNSAF GFQGRLLHLSAGQRLGVHLHTEARARHAWQL TQGATVLGLFRVTPEIPAGLPSPRSEGGGGSGG GGSREGPELSPDDPAGLLDLRQGMFAQLVAQN VLLIDGPLSWYSDPGLAGVSLTGGLSYKEDTKE LVVAKAGVYYVFFQLELRRVVAGEGSGSVSLA LHLQPLRSAAGAAALALTVDLPPASSEARNSAF GFQGRLLHLSAGQRLGVHLHTEARARHAWQL TQGATVLGLFRVTPEIPAGLPSPRSE |
| 55 | DP47 Fc knob chain fused to monomeric hu 4-1BBL (71-254) | EVQLLESGGGLVQPGGSLRLSCAASGFTFSSYA MSWVRQAPGKGLEWVSAIIGSGASTYYADSVK GRFTISRDNSKNTLYLQMNSLRAEDTAVYYCA KGWFGGFNYWGQGTLVTVSSASTKGPSVFPLA PSSKSTSGGTAALGCLVKDYFPEPVTVSWNSG ALTSGVHTFPAVLQSSGLYSLSSVVTVPSSSLGT QTYICNVNHKPSNTKVDKKVEPKSCDKTHTCP PCPAPEAAGGPSVFLFPPKPKDTLMISRTPEVTC VVVDVSHEDPEVKFNWYVDGVEVHNAKTKPR EEQYNSTYRVVSVLTVLHQDWLNGKEYKCKV SNKALGAPIEKTISKAKGQPREPQVYTLPPCRD ELTKNQVSLWCLVKGFYPSDIAVEWESNGQPE NNYKTTPPVLDSDGSFFLYSKLTVDKSRWQQG NVFSCSVMHEALHNHYTQKSLSLSPGGGGGSG GGGSREGPELSPDDPAGLLDLRQGMFAQLVAQ NVLLIDGPLSWYSDPGLAGVSLTGGLSYKEDT KELVVAKAGVYYVFFQLELRRVVAGEGSGSVS LALHLQPLRSAAGAAALALTVDLPPASSEARNS AFGFQGRLLHLSAGQRLGVHLHTEARARHAW QLTQGATVLGLFRVTPEIPAGLPSPRSE |
| 56 | Human (hu) FAP | UniProt no. Q12884 |
| 57 | hu FAP ectodomain + poly-lys-tag + his$_6$-tag | RPSRVHNSEENTMRALTLKDILNGTFSYKTFFP NWISGQEYLHQSADNNIVLYNIETGQSYTILSN RTMKSVNASNYGLSPDRQFVYLESDYSKLWR YSYTATYYIYDLSNGEFVRGNELPRPIQYLCWS PVGSKLAYVYQNNIYLKQRPGDPPFQITFNGRE NKIFNGIPDWVYEEEMLATKYALWWSPNGKFL AYAEFNDTDIPVIAYSYYGDEQYPRTINIPYPKA GAKNPVVRIFIIDTTYPAYVGPQEVPVPAMIASS DYYFSWLTWVTDERVCLQWLKRVQNVSVLSI CDFREDWQTWDCPKTQEHIEESRTGWAGGFFV STPVFSYDAISYYKIFSDKDGYKHIHYIKDTVEN AIQITSGKWEAINIFRVTQDSLFYSSNEFEEYPG RRNIYRISIGSYPPSKKCVTCHLRKERCQYYTAS FSDYAKYYALVCYGPGIPISTLHDGRTDQEIKIL EENKELENALKNIQLPKEEIKKLEVDEITLWYK MILPPQFDRSKKYPLLIQVYGGPCSQSVRSVFA VNWISYLASKEGMVIALVDGRGTAFQGDKLLY AVYRKLGVYEVEDQITAVRKFIEMGFIDEKRIA |

TABLE C-continued (Sequences):

| SEQ ID NO: | Name | Sequence |
|---|---|---|
| | | IWGWSYGGYVSSLALASGTGLFKCGIAVAPVS SWEYYASVYTERFMGLPTKDDNLEHYKNSTV MARAEYFRNVDYLLIHGTADDNVHFQNSAQIA KALVNAQVDFQAMWYSDQNHGLSGLSTNHLY THMTHFLKQCFSLSDGKKKKKGHHHHHH |
| 58 | mouse FAP | UniProt no. P97321 |
| 59 | Murine FAP ectodomain + poly-lys-tag + his$_6$-tag | RPSRVYKPEGNTKRALTLKDILNGTFSYKTYFP NWISEQEYLHQSEDDNIVFYNIETRESYIILSNST MKSVNATDYGLSPDRQFVYLESDYSKLWRYS YTATYYIYDLQNGEFVRGYELPRPIQYLCWSPV GSKLAYVYQNNIYLKQRPGDPPFQITYTGRENR IFNGIPDWVYEEEMLATKYALWWSPDGKFLAY VEFNDSDIPIIAYSYYGDGQYPRTINIPYPKAGA KNPVVRVFIVDTTYPHHVGPMEVPVPEMIASSD YYFSWLTWVSSERVCLQWLKRVQNVSVLSICD FREDWHAWECPKNQEHVEESRTGWAGGFFVS TPAFSQDATSYYKIFSDKDGYKHIHYIKDTVEN AIQITSGKWEAIYIFRVTQDSLFYSSNEFEGYPG RRNIYRISIGNSPPSKKCVTCHLRKERCQYYTAS FSYKAKYYALVCYGPGLPISTLHDGRTDQEIQV LEENKELENSLRNIQLPKVEIKKLKDGGLTFWY KMILPPQFDRSKKYPLLIQVYGGPCSQSVKSVF AVNWITYLASKEGIVIALVDGRGTAFQGDKFL HAVYRKLGVYEVEDQLTAVRKFIEMGFIDEERI AIWGWSYGGYVSSLALASGTGLFKCGIAVAPV SSWEYYASIYSERFMGLPTKDDNLEHYKNSTV MARAEYFRNVDYLLIHGTADDNVHFQNSAQIA KALVNAQVDFQAMWYSDQNHGILSGRSQNHL YTHMTHFLKQCFSLSDGKKKKKGHHHHHH |
| 60 | Cynomolgus FAP ectodomain + poly-lys-tag + his$_6$-tag | RPPRVHNSEENTMRALTLKDILNGTFSYKTFFP NWISGQEYLHQSADNNIVLYNIETGQSYTILSN RTMKSVNASNYGLSPDRQFVYLESDYSKLWR YSYTATYYIYDLSNGEFVRGNELPRPIQYLCWS PVGSKLAYVYQNNIYLKQRPGDPPFQITFNGRE NKIFNGIPDWVYEEEMLATKYALWWSPNGKFL AYAEFNDTDIPVIAYSYYGDEQYPRTINIPYPKA GAKNPFVRIFIIDTTYPAYVGPQEVPVPAMIASS DYYFSWLTWVTDERVCLQWLKRVQNVSVLSI CDFREDWQTWDCPKTQEHIEESRTGWAGGFFV STPVFSYDAISYYKIFSDKDGYKHIHYIKDTVEN AIQITSGKWEAINIFRVTQDSLFYSSNEFEDYPG RRNIYRISIGSYPPSKKCVTCHLRKERCQYYTAS FSDYAKYYALVCYGPGIPISTLHDGRTDQEIKIL EENKELENALKNIQLPKEEIKKLEVDEITLWYK MILPPQFDRSKKYPLLIQVYGGPCSQSVRSVFA VNWISYLASKEGMVIALVDGRGTAFQGDKLLY AVYRKLGVYEVEDQITAVRKFIEMGFIDEKRIA IWGWSYGGYVSSLALASGTGLFKCGIAVAPVS SWEYYASVYTERFMGLPTKDDNLEHYKNSTV MARAEYFRNVDYLLIHGTADDNVHFQNSAQIA KALVNAQVDFQAMWYSDQNHGLSGLSTNHLY THMTHFLKQCFSLSDGKKKKKGHHHHHH |
| 61 | human CEA | UniProt no. P06731 |
| 62 | full length 4-1BBL | UniProt No. P41273 |
| 63 | 4-1BBL (50-254) | ACPWAVSGARASPGSAASPRLREGPELSPDDPA GLLDLRQGMFAQLVAQNVLLIDGPLSWYSDPG LAGVSLTGGLSYKEDTKELVVAKAGVYYVFFQ LELRRVVAGEGSGSVSLALHLQPLRSAAGAAA LALTVDLPPASSEARNSAFGFQGRLLHLSAGQR LGVHLHTEARARHAWQLTQGATVLGLFRVTP EIPAGLPSPRSE |
| 64 | human 4-1BB | UniProt accession No. Q07011 |
| 65 | murine 4-1BB | UniProt accession No. P20334 |
| 66 | cynomolgus 4-1BB | Uniprot accession No. F6W5G6 |
| 67 | G4S peptide linker | GGGGS |

TABLE C-continued (Sequences):

| SEQ ID NO: | Name | Sequence |
|---|---|---|
| 68 | (G4S)2 | GGGGSGGGGS |
| 69 | (SG4)2 | SGGGGSGGGG |
| 70 | peptide linker | GGGGSGGGGSGGGG |
| 71 | peptide linker | GSPGSSSSGS |
| 72 | (G4S)3 peptide linker | GGGGSGGGGSGGGGS3 |
| 73 | (G4S)4 peptide linker | GGGGSGGGGSGGGGSGGGGS |
| 74 | peptide linker | GSGSGSGS |
| 75 | peptide linker | GSGSGNGS |
| 76 | peptide linker | GGSGSGSG |
| 77 | peptide linker | GGSGSG |
| 78 | peptide linker | GGSG |
| 79 | peptide linker | GGSGNGSG |
| 80 | peptide linker | GGNGSGSG |
| 81 | peptide linker | GGNGSG |
| 82 | anti-CEACAM5 Fc hole chain (Construct 5.4) | QVQLVQSGAEVKKPGSSVKVSCKASGFNIKDT YMHWVRQAPGQGLEWMGRIDPANGNSKYVP KFQGRVTITADTSTSTAYMELSSLRSEDTAVYY CAPFGYYVSDYAMAYWGQGTLVTVSSASTKG PSVFPLAPSSKSTSGGTAALGCLVKDYFPEPVT VSWNSGALTSGVHTFPAVLQSSGLYSLSSVVT VPSSSLGTQTYICNVNHKPSNTKVDKKVEPKSC DKTHTCPPCPAPEAAGGPSVFLFPPKPKDTLMIS RTPEVTCVVVDVSHEDPEVKFNWYVDGVEVH NAKTKPREEQYNSTYRVVSVLTVLHQDWLNG KEYKCKVSNKALGAPIEKTISKAKGQPREPQVC TLPPSRDELTKNQVSLSCAVKGFYPSDIAVEWE SNGQPENNYKTTPPVLDSDGSFFLVSKLTVDKS RWQQGNVFSCSVMHEALHNHYTQKSLSLSPG K |
| 83 | anti-CEACAM5 light chain (Construct 5.4) | EIVLTQSPATLSLSPGERATLSCRAGESVDIFGV GFLHWYQQKPGQAPRLLIYRASNRATGIPARFS GSGSGTDFTLTISSLEPEDFAVYYCQQTNEDPY TFGQGTKLEIKRTVAAPSVFIFPPSDEQLKSGTA SVVCLLNNFYPREAKVQWKVDNALQSGNSQE SVTEQDSKDSTYSLSSTLTLSKADYEKHKVYA CEVTHQGLSSPVTKSFNRGEC |
| 84 | DP47 light chain | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPLTFGQ GTKVEIKRTVAAPSVFIFPPSDEQLKSGTASVVC LLNNFYPREAKVQWKVDNALQSGNSQESVTE QDSKDSTYSLSSTLTLSKADYEKHKVYACEVT HQGLSSPVTKSFNRGEC |
| 85 | CD20 | UniProt accession No. P11836 |
| 86 | di-mu4-1BBL-CL Fc knob chain | see Table 3 |
| 87 | mono-mu4-1BBL-CH1 chain | see Table 3 |
| 88 | VHCH1 (4B9) Fc hole chain | see Table 3 |
| 89 | VLCL(4B9) Light chain | see Table 3 |

TABLE C-continued (Sequences):

| SEQ ID NO: | Name | Sequence |
|---|---|---|
| 90 | VHCH1 (MU137-1)-Heavy chain Fc-DD-VL (28H1) | see Table 5 |
| 91 | VHCH1 (20H4.9)-Heavy chain Fc-KK-VH (28H1) | see Table 5 |
| 92 | VLCL-Light chain (MU137-1) | see Table 5 |
| 93 | VHCH1 (MU137-1)-Heavy chain Fc-DD-VH (28H1) | see Table 6 |
| 94 | VHCH1 (MU137-1)-Heavy chain Fc-KK-VL (28H1) | see Table 6 |
| 95 | human HER-2 | UniProt Acc. No. P04626-1 |
| 96 | heavy chain variable domain VH, trastuzumab | EVQLVESGGGLVQPGGSLRLSCAASGFNIKDTY IHWVRQAPGKGLEWVARIYPTNGYTRYAD SV KGRFTISADTSKNTAYLQMNSLRAEDTAVYYC SRWGGDGFYAMDYWGQGTLVTVSS |
| 97 | light chain variable domain VL, trastuzumab | DIQMTQSPSSLSASVGDRVTITCRASQDVNTAV AWYQQKPGKAPKLLIYSASFLYSGVPSRFSGSR SGTDFTLTISSLQPEDFATYYCQQHYTTPPTFGQ GTKVEIK |
| 98 | heavy chain variable domain VH, pertuzumab | EVQLVESGGGLVQPGGSLRLSCAASGFTFTDYT MDWVRQAPGKGLEWVADVNPNSGGSIYNQRF KGRFTLSVDRSKNTLYLQMNSLRAEDTAVYYC ARNLGPSFYFDYWGQGTLVTVSS |
| 99 | light chain variable domain VL, pertuzumab | DIQMTQSPSSLSASVGDRVTITCKASQDVSIGV AWYQQKPGKAPKLLIYSASYRYTGVPSRFSGS GSGTDFTLTISSLQPEDFATYYCQQYYIYPYTFG QGTKVEIK |

General information regarding the nucleotide sequences of human immunoglobulin light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to the numbering systems according to Kabat (Kabat, E. A., et al., Sequences of Proteins of Immunological Interest, 5th ed., Public Health Service, National Institutes of Health, Bethesda, MD (1991)) as defined above.

Aspects of the Invention

In the following, some of the aspects of the invention are listed.

1. A 4-1BB agonist for use in a method for treating or delaying progression of cancer, wherein the 4-1BB agonist is used in combination with a HER-2 targeting agent.

2. A 4-1BB agonist for use in a method for treating or delaying progression of cancer, wherein the 4-1BB agonist is used in combination with a HER-2 targeting agent and wherein the 4-1BB agonist is an antigen binding molecule comprising at least one antigen binding domain capable of specific binding to a tumor-associated antigen.

3. The 4-1BB agonist for use in a method of aspect 1, wherein the 4-1BB agonist and the HER-2 targeting agent are administered together in a single composition or administered separately in two or more different compositions.

4. The 4-1BB agonist for use in a method of aspect 1 or 2, wherein the 4-1BB agonist comprises three ectodomains of 4-1BBL or fragments thereof.

5. The 4-1BB agonist for use in a method of the preceding aspects, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

6. The 4-1BB agonist for use in a method of the preceding aspects, wherein the 4-1BB agonist is an antigen binding molecule comprising three ectodomains of 4-1BBL or fragments thereof and at least one antigen binding domain capable of specific binding to a tumor-associated antigen.

7. The 4-1BB agonist for use in a method of the preceding aspects, wherein the 4-1BB agonist is an antigen binding molecule comprising three ectodomains of 4-1BBL or fragments thereof and at least one antigen binding domain capable of specific binding to Fibroblast activation protein (FAP).

8. The 4-1BB agonist for use in a method of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises (a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

9. The 4-1BB agonist for use in a method of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

10. The 4-1BB agonist for use in a method of of the preceding aspects, wherein the 4-1BB agonist is an antigen binding molecule comprising an IgG Fc domain, specifically an IgG1 Fc domain or an IgG4 Fc domain.

11. The 4-1BB agonist for use in a method of the preceding aspects, wherein the 4-1BB agonist is an antigen binding molecule comprising a Fc domain that comprises one or more amino acid substitution that reduces binding to an Fc receptor and/or effector function.

12. The 4-1BB agonist for use in a method of the preceding aspects, wherein the 4-1BB agonist is an antigen binding molecule comprising
(a) at least one antigen binding domain capable of specific binding to FAP,
(b) a first and a second polypeptide that are linked to each other by a disulfide bond,
wherein the first polypeptide comprises two ectodomains of 4-1BBL or fragments thereof that are connected to each other by a peptide linker and in that the second polypeptide comprises one ectodomain of 4-1BBL or a fragment thereof.

13. The 4-1BB agonist for use in a method of any one of the preceding aspects, wherein the 4-1BB agonist is an antigen binding molecule comprising
(a) at least one Fab domain capable of specific binding to CD19, and
(b) a first and a second polypeptide that are linked to each other by a disulfide bond,
wherein the antigen binding molecule is characterized in that
(i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or
(ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
(iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

14. The 4-1BB agonist for use in a method of the preceding aspects, wherein the 4-1BB agonist is an antigen binding molecule comprising
(a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and
(b) a first and a second polypeptide that are linked to each other by a disulfide bond,
wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

15. The 4-1BB agonist for use in a method of the preceding aspects, wherein the 4-1BB agonist is an antigen binding molecule selected from the group consisting of
a) a molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:43 and a second light chain comprising the amino acid sequence of SEQ ID NO:44; and
b) a molecule comprising a first heavy chain comprising the amino acid sequence of SEQ ID NO:45, a first light chain comprising the amino acid sequence of SEQ ID NO:46, a second heavy chain comprising the amino acid sequence of SEQ ID NO:47 and a second light chain comprising the amino acid sequence of SEQ ID NO:48.

16. The 4-1BB agonist for use in a method of the preceding aspects, wherein the 4-1BB agonist is an antigen binding molecule comprising
   (a) at least one antigen binding domain capable of specific binding to FAP,
   (b) a polypeptide comprising three ectodomains of 4-1BBL or fragments thereof that are connected to each other by peptide linkers.

17. The 4-1BB agonist for use in a method of of the preceding aspects, wherein the 4-1BB agonist is an antigen binding molecule comprising
   (a) at least one antigen binding domain capable of specific binding to FAP,
   (b) a polypeptide comprising three ectodomains of 4-1BBL or fragments thereof that are connected to each other by peptide linkers, and
   (c) a Fc domain composed of a first and a second subunit capable of stable association,
   wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

18. The 4-1BB agonist for use in a method of the preceding aspects, wherein the 4-1BB agonist is an anti-FAP/anti-4-1BB bispecific antibody.

19. The 4-1BB agonist for use in a method of the preceding aspects, wherein the 4-1BB agonist is an antigen binding molecule comprising three ectodomains of 4-1BBL or fragments thereof and at least one antigen binding domain capable of specific binding to CEA.

20. The 4-1BB agonist for use in a method of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises (a) a heavy chain variable region ($V_H$CEA) comprising (i) CDR-H1 comprising the amino acid sequence of SEQ ID NO:33, (ii) CDR-H2 comprising the amino acid sequence of SEQ ID NO:34, and (iii) CDR-H3 comprising the amino acid sequence of SEQ ID NO:35, and a light chain variable region ($V_L$CEA) comprising (iv) CDR-L1 comprising the amino acid sequence of SEQ ID NO:36, (v) CDR-L2 comprising the amino acid sequence of SEQ ID NO:37, and (vi) CDR-L3 comprising the amino acid sequence of SEQ ID NO:38.

21. The 4-1BB agonist for use in a method of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:39 and a light chain variable region ($V_L$CEA) comprising an amino acid sequence of SEQ ID NO:40.

22. The 4-1BB agonist for use in a method of the preceding aspects, wherein the 4-1BB agonist is an antigen binding molecule comprising an IgG Fc domain, specifically an IgG1 Fc domain or an IgG4 Fc domain.

23. The 4-1BB agonist for use in a method of the preceding aspects, wherein the 4-1BB agonist is an antigen binding molecule comprising a Fc domain that comprises one or more amino acid substitution that reduces binding to an Fc receptor and/or effector function.

24. The 4-1BB agonist for use in a method of the preceding aspects, wherein the 4-1BB agonist is an antigen binding molecule comprising
   (a) at least one antigen binding domain capable of specific binding to CEA,
   (b) a first and a second polypeptide that are linked to each other by a disulfide bond,
   wherein the first polypeptide comprises two ectodomains of 4-1BBL or fragments thereof that are connected to each other by a peptide linker and in that the second polypeptide comprises one ectodomain of 4-1BBL or a fragment thereof.

25. The 4-1BB agonist for use in a method of any one of the preceding aspects, wherein the 4-1BB agonist is an antigen binding molecule comprising
   (a) at least one Fab domain capable of specific binding to CEA, and
   (b) a first and a second polypeptide that are linked to each other by a disulfide bond,
   wherein the antigen binding molecule is characterized in that
   (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or
   (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
   (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

26. The 4-1BB agonist for use in a method of the preceding aspects, wherein the 4-1BB agonist is an antigen binding molecule comprising
   (a) at least one Fab domain capable of specific binding to CEA comprising a heavy chain variable region ($V_H$CEA) comprising the amino acid sequence of SEQ ID NO:39 and a light chain variable region ($V_L$CEA) comprising the amino acid sequence of SEQ ID NO:40, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

27. The 4-1BB agonist for use in a method of the preceding aspects, wherein the 4-1BB agonist is an antigen binding molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:82 and a second light chain comprising the amino acid sequence of SEQ ID NO:83.

28. The 4-1BB agonist for use in a method of the preceding aspects, wherein the 4-1BB agonist is an antigen binding molecule comprising
(a) at least one antigen binding domain capable of specific binding to CEA,
(b) a polypeptide comprising three ectodomains of 4-1BBL or fragments thereof that are connected to each other by peptide linkers.

29. The 4-1BB agonist for use in a method of the preceding aspects, wherein the 4-1BB agonist is an antigen binding molecule comprising
(a) at least one antigen binding domain capable of specific binding to CEA,
(b) a polypeptide comprising three ectodomains of 4-1BBL or fragments thereof that are connected to each other by peptide linkers, and
(c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

30. The 4-1BB agonist for use in a method of the preceding aspects, wherein the 4-1BB agonist is an anti-CEA/anti-4-1BB bispecific antibody.

31. The 4-1BB agonist for use in a method of any one of the preceding aspects, wherein the 4-1BB agonist is used in combination with a HER-2 targeting agent and wherein the combination is administered at intervals from about about one week to three weeks.

32. A pharmaceutical product comprising (A) a first composition comprising as active ingredient a 4-1BB agonist and a pharmaceutically acceptable carrier; and (B) a second composition comprising as active ingredient a HER-2 targeting agent and a pharmaceutically acceptable carrier, for use in the combined, sequential or simultaneous, treatment of a disease, in particular cancer.

33. A pharmaceutical composition comprising a 4-1BB agonist and a HER-2 targeting agent.

34. The pharmaceutical composition of aspect 32 for use in the treatment of solid tumors.

35. The pharmaceutical composition of any one of the preceding aspects, wherein the 4-1BB agonist comprises three ectodomains of 4-1BBL or fragments thereof.

36. The pharmaceutical composition of any one of the preceding aspects, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

37. The pharmaceutical composition of any one of the preceding aspects, wherein the 4-1BB agonist is an antigen binding molecule comprising three ectodomains of 4-1BBL or fragments thereof and at least one antigen binding domain capable of specific binding to a tumor associated antigen.

38. The pharmaceutical composition of any one of the preceding aspects, wherein the tumor associated antigen is FAP.

39. The pharmaceutical composition of any one of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises
(a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
(b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

40. The pharmaceutical composition of any one of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

41. The pharmaceutical composition of any one of the preceding aspects, wherein the 4-1BB agonist is an antigen binding molecule further comprising a Fc domain composed of a first and a second subunit capable of stable association.

42. The pharmaceutical composition of any one of the preceding aspects, wherein the 4-1BB agonist is an antigen binding molecule comprising an IgG Fc domain, specifically an IgG1 Fc domain or an IgG4 Fc domain.

43. The pharmaceutical composition of any one of the preceding aspects, wherein the 4-1BB agonist is an antigen binding molecule comprising a Fc domain that comprises one or more amino acid substitution that reduces binding to an Fc receptor and/or effector function.

44. The pharmaceutical composition of any one of the preceding aspects, wherein the 4-1BB agonist is an antigen binding molecule comprising an IgG1 Fc domain comprising the amino acid substitutions L234A, L235A and P329G.

45. The pharmaceutical composition of any one of the preceding aspects, wherein the 4-1BB agonist is an antigen binding molecule comprising
   (a) at least one antigen binding domain capable of specific binding to FAP,
   (b) a first and a second polypeptide that are linked to each other by a disulfide bond,
   wherein the first polypeptide comprises two ectodomains of 4-1BBL or fragments thereof that are connected to each other by a peptide linker and in that the second polypeptide comprises one ectodomain of 4-1BBL or a fragment thereof.

46. The pharmaceutical composition of any one of the preceding aspects, wherein the 4-1BB agonist is an antigen binding molecule comprising
   (a) at least one Fab domain capable of specific binding to FAP, and
   (b) a first and a second polypeptide that are linked to each other by a disulfide bond,
   wherein the antigen binding molecule is characterized in that
      (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or
      (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
      (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

47. The pharmaceutical composition of any one of the preceding aspects, wherein the 4-1BB agonist is an antigen binding molecule comprising
   (a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and
   (b) a first and a second polypeptide that are linked to each other by a disulfide bond,
   wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

48. The pharmaceutical composition of any one of the preceding aspects, wherein wherein the 4-1BB agonist is an antigen binding molecule selected from the group consisting of
   a) a molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:43 and a second light chain comprising the amino acid sequence of SEQ ID NO:44; and
   b) a molecule comprising a first heavy chain comprising the amino acid sequence of SEQ ID NO:45, a first light chain comprising the amino acid sequence of SEQ ID NO:46, a second heavy chain comprising the amino acid sequence of SEQ ID NO:47 and a second light chain comprising the amino acid sequence of SEQ ID NO:48.

49. The pharmaceutical composition of any one of the preceding aspects, wherein the 4-1BB agonist is an antigen binding molecule comprising
   (a) at least one antigen binding domain capable of specific binding to FAP,
   (b) a polypeptide comprising three ectodomains of 4-1BBL or fragments thereof that are connected to each other by peptide linkers.

50. The pharmaceutical composition of any one of the preceding aspects, wherein the 4-1BB agonist is an antigen binding molecule comprising
   (a) at least one antigen binding domain capable of specific binding to FAP,
   (b) a polypeptide comprising three ectodomains of 4-1BBL or fragments thereof that are connected to each other by peptide linkers, and
   (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

51. The pharmaceutical composition of any one of the preceding aspects, wherein the 4-1BB agonist is an anti-FAP/anti-4-1BB bispecific antibody.

52. The pharmaceutical composition of any one of the preceding aspects, wherein the tumor associated antigen is CEA.

53. The pharmaceutical composition of any one of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising (i) CDR-H1 comprising the amino acid sequence of SEQ ID NO:33, (ii) CDR-H2 comprising the amino acid sequence of SEQ ID NO:34, and (iii) CDR-H3 comprising the amino acid sequence of SEQ ID NO:35, and a light chain variable region ($V_L$CEA) comprising (iv) CDR-L1 comprising the amino acid sequence of SEQ ID NO:36, (v) CDR-L2 comprising the amino acid sequence of SEQ ID NO:37, and (vi) CDR-L3 comprising the amino acid sequence of SEQ ID NO:38.

54. The pharmaceutical composition of any one of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:39 and a light chain variable region ($V_L$CEA) comprising an amino acid sequence of SEQ ID NO:40.

55. The pharmaceutical composition of any one of the preceding aspects, wherein the 4-1BB agonist is an antigen binding molecule further comprising a Fc domain composed of a first and a second subunit capable of stable association.

56. The pharmaceutical composition of any one of the preceding aspects, wherein the 4-1BB agonist is an antigen binding molecule comprising an IgG Fc domain, specifically an IgG1 Fc domain or an IgG4 Fc domain.

57. The pharmaceutical composition of any one of the preceding aspects, wherein the 4-1BB agonist is an antigen binding molecule comprising a Fc domain that comprises one or more amino acid substitution that reduces binding to an Fc receptor and/or effector function.

58. The pharmaceutical composition of any one of the preceding aspects, wherein the 4-1BB agonist is an antigen binding molecule comprising an IgG1 Fc domain comprising the amino acid substitutions L234A, L235A and P329G.

59. The pharmaceutical composition of any one of the preceding aspects, wherein the 4-1BB agonist is an antigen binding molecule comprising
(a) at least one antigen binding domain capable of specific binding to CEA,
(b) a first and a second polypeptide that are linked to each other by a disulfide bond,
wherein the first polypeptide comprises two ectodomains of 4-1BBL or fragments thereof that are connected to each other by a peptide linker and in that the second polypeptide comprises one ectodomain of 4-1BBL or a fragment thereof.

60. The pharmaceutical composition of any one of the preceding aspects, wherein the 4-1BB agonist is an antigen binding molecule comprising
(a) at least one Fab domain capable of specific binding to CEA, and
(b) a first and a second polypeptide that are linked to each other by a disulfide bond,
wherein the antigen binding molecule is characterized in that
(i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or
(ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
(iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

61. The pharmaceutical composition of any one of the preceding aspects, wherein the 4-1BB agonist is an antigen binding molecule comprising
(a) (a) at least one Fab domain capable of specific binding to CEA comprising a heavy chain variable region ($V_H$CEA) comprising the amino acid sequence of SEQ ID NO:39 and a light chain variable region ($V_L$CEA) comprising the amino acid sequence of SEQ ID NO:40, and
(b) a first and a second polypeptide that are linked to each other by a disulfide bond,
wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

62. The pharmaceutical composition of any one of the preceding aspects, wherein wherein the 4-1BB agonist is an antigen binding molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:82 and a second light chain comprising the amino acid sequence of SEQ ID NO:83.

63. The pharmaceutical composition of any one of the preceding aspects, wherein the 4-1BB agonist is an antigen binding molecule comprising
(a) at least one antigen binding domain capable of specific binding to CEA, (b) a polypeptide comprising ectodomains of 4-1BBL or fragments thereof that are connected to each other by peptide linkers.

64. The pharmaceutical composition of any one of the preceding aspects, wherein the 4-1BB agonist is an antigen binding molecule comprising
    (a) at least one antigen binding domain capable of specific binding to CEA,
    (b) a polypeptide comprising three ectodomains of 4-1BBL or fragments thereof that are connected to each other by peptide linkers, and
    (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

65. The pharmaceutical composition of any one of the preceding aspects, wherein the 4-1BB agonist is an anti-CEA/anti-4-1BB bispecific antibody.

66. The 4-1BB agonist for use or the pharmaceutical composition of any one of the preceding aspects, wherein the HER-2 targeting agent is one or more of trastuzumab, pertuzumab, and/or trastuzumab emtansine.

67. The 4-1BB agonist for use or the pharmaceutical composition of any one of the preceding aspects, wherein the HER-2 targeting agent is trastuzumab.

68. The pharmaceutical composition of any one of the preceding aspects, wherein the 4-1BB agonist is used in combination with a HER-2 targeting agent and wherein the combination is administered at intervals from about about one week to three weeks.

69. The pharmaceutical composition of any one of the preceding aspects for use in treating or delaying progression of a proliferative disease, in particular cancer.

70. The pharmaceutical composition of any one of the preceding aspects for use in the treatment of breast cancer, ovarian cancer, stomach cancer, gastric cancer, oesophageal cancer, lung cancer, uterine cancer, salivary duct carcinoma, bladder cancer, endometrial cancer, pancreatic cancer, colon cancer, prostate cancer, and/or head and neck cancer.

71. A kit for treating or delaying progression of cancer in a subject, comprising a package comprising (A) a first composition comprising as active ingredient an 4-1BB agonist and a pharmaceutically acceptable carrier; (B) a second composition comprising as active ingredient a HER-2 targeting agent and a pharmaceutically acceptable carrier, and (C) instructions for using the compositions in a combination therapy.

72. Use of a combination of a 4-1BB agonist and a HER-2 targeting agent in the manufacture of a medicament for treating or delaying progression of a proliferative disease, in particular cancer.

73. Use of a combination of a 4-1BB agonist and a HER-2 targeting agent in the manufacture of a medicament, wherein the medicament is for the treatment of solid tumors.

74. A method for treating or delaying progression of cancer in a subject comprising administering to the subject an effective amount of a 4-1BB agonist and an effective amount of a HER-2 targeting agent.

75. A method for treating or delaying progression of cancer in a subject comprising administering to the subject an effective amount of of a 4-1BB agonist and an effective amount of a HER-2 targeting agent, wherein the 4-1BB agonist is an antigen binding molecule.

76. The method of any one of the preceding aspects, wherein the 4-1BB agonist is an antigen binding molecule comprising a Fc domain.

77. The method of any one of the preceding aspects, wherein the 4-1BB agonist is an antigen binding molecule comprising a Fc domain with modifications reducing Fcγ receptor binding and/or effector function.

78. The method of any one of the preceding aspects, wherein the 4-1BB agonist is an antigen binding molecule comprising three ectodomains of 4-1BBL or fragments thereof.

79. The method of any one of the preceding aspects, wherein the 4-1BB agonist is an antigen binding molecule comprising three ectodomains of 4-1BBL or fragments thereof and an antigen binding domain capable of specific binding to a tumor associated antigen.

80. The method of any one of the preceding aspects, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

81. The method of any one of the preceding aspects, wherein the 4-1BB agonist is an antigen binding molecule comprising three ectodomains of 4-1BBL or fragments thereof and at least one moiety capable of specific binding to FAP, wherein the antigen binding domain capable of specific binding to FAP comprises
    (a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
    (b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

82. The method of any one of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

83. The method of any one of the preceding aspects, wherein the 4-1BB agonist is an antigen binding molecule further comprising a Fc domain composed of a first and a second subunit capable of stable association.

84. The method of any one of the preceding aspects, wherein the 4-1BB agonist is an antigen binding molecule comprising an IgG Fc domain, specifically an IgG1 Fc domain or an IgG4 Fc domain.

85. The method of any one of the preceding aspects, wherein the 4-1BB agonist is an antigen binding molecule comprising a Fc domain that comprises one or more amino acid substitution that reduces binding to an Fc receptor and/or effector function.

86. The method of any one of the preceding aspects, wherein the 4-1BB agonist is an antigen binding molecule comprising
(a) at least one antigen binding domain capable of specific binding to FAP,
(b) a first and a second polypeptide that are linked to each other by a disulfide bond,
wherein the first polypeptide comprises two ectodomains of 4-1BBL or fragments thereof that are connected to each other by a peptide linker and in that the second polypeptide comprises one ectodomain of 4-1BBL or a fragment thereof.

87. The method of any one of the preceding aspects, wherein the 4-1BB agonist is an antigen binding molecule comprising
(a) at least one Fab domain capable of specific binding to FAP, and
(b) a first and a second polypeptide that are linked to each other by a disulfide bond,
wherein the antigen binding molecule is characterized in that
(i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or
(ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
(iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

88. The method of any one of the preceding aspects, wherein the 4-1BB agonist is an antigen binding molecule comprising
(a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and
(b) a first and a second polypeptide that are linked to each other by a disulfide bond,
wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

89. The method of any one of the preceding aspects, wherein the 4-1BB agonist is an antigen binding molecule selected from the group consisting of
a) a molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:43 and a second light chain comprising the amino acid sequence of SEQ ID NO:44; and
b) a molecule comprising a first heavy chain comprising the amino acid sequence of SEQ ID NO:45, a first light chain comprising the amino acid sequence of SEQ ID NO:46, a second heavy chain comprising the amino acid sequence of SEQ ID NO:47 and a second light chain comprising the amino acid sequence of SEQ ID NO:48.

90. The method of any one of the preceding aspects, wherein the 4-1BB agonist is an antigen binding molecule comprising
(a) at least one antigen binding domain capable of specific binding to FAP,
(b) a polypeptide comprising three ectodomains of 4-1BBL or fragments thereof that are connected to each other by peptide linkers.

91. The method of any one of the preceding aspects, wherein the 4-1BB agonist is an anti-FAP/anti-4-1BB bispecific antibody.

92. The method of any one of the preceding aspects, wherein the 4-1BB agonist is an antigen binding molecule comprising three ectodomains of 4-1BBL or fragments thereof and at least one moiety capable of specific binding to CEA, wherein the antigen binding domain capable of specific binding to CEA comprises
a heavy chain variable region ($V_H$CEA) comprising (i) CDR-H1 comprising the amino acid sequence of SEQ ID NO:33, (ii) CDR-H2 comprising the amino acid sequence of SEQ ID NO:34, and (iii) CDR-H3 comprising the amino acid sequence of SEQ ID NO:35, and a light chain variable region ($V_L$CEA) comprising (iv) CDR-L1 comprising the amino acid sequence of SEQ ID NO:36, (v) CDR-L2 comprising the amino acid sequence of SEQ ID NO:37, and (vi) CDR-L3 comprising the amino acid sequence of SEQ ID NO:38.

93. The method of any one of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:39 and a light chain variable region ($V_L$CEA) comprising an amino acid sequence of SEQ ID NO:40.

94. The method of any one of the preceding aspects, wherein the 4-1BB agonist is an antigen binding molecule further comprising a Fc domain composed of a first and a second subunit capable of stable association.

95. The method of any one of the preceding aspects, wherein the 4-1BB agonist is an antigen binding molecule comprising an IgG Fc domain, specifically an IgG1 Fc domain or an IgG4 Fc domain.

96. The method of any one of the preceding aspects, wherein the 4-1BB agonist is an antigen binding molecule comprising a Fc domain that comprises one or more amino acid substitution that reduces binding to an Fc receptor and/or effector function.

97. The method of any one of the preceding aspects, wherein the 4-1BB agonist is an antigen binding molecule comprising
   (a) at least one antigen binding domain capable of specific binding to CEA,
   (b) a first and a second polypeptide that are linked to each other by a disulfide bond,
   wherein the first polypeptide comprises two ectodomains of 4-1BBL or fragments thereof that are connected to each other by a peptide linker and in that the second polypeptide comprises one ectodomain of 4-1BBL or a fragment thereof.

98. The method of any one of the preceding aspects, wherein the 4-1BB agonist is an antigen binding molecule comprising
   (a) at least one Fab domain capable of specific binding to CEA, and
   (b) a first and a second polypeptide that are linked to each other by a disulfide bond,
   wherein the antigen binding molecule is characterized in that
      (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or
      (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or
      (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

99. The method of any one of the preceding aspects, wherein the 4-1BB agonist is an antigen binding molecule comprising
   (a) at least one Fab domain capable of specific binding to CEA comprising a heavy chain variable region ($V_H$CEA) comprising an amino acid sequence of SEQ ID NO:39 and a light chain variable region ($V_L$CEA) comprising an amino acid sequence of SEQ ID NO:40, and
   (b) a first and a second polypeptide that are linked to each other by a disulfide bond,
   wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

100. The method of any one of the preceding aspects, wherein the 4-1BB agonist is an antigen binding molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:82 and a second light chain comprising the amino acid sequence of SEQ ID NO:83.

101. The method of any one of the preceding aspects, wherein the 4-1BB agonist is an antigen binding molecule comprising
   (a) at least one antigen binding domain capable of specific binding to FAP,
   (b) a polypeptide comprising three ectodomains of 4-1BBL or fragments thereof that are connected to each other by peptide linkers.

102. The method of any one of the preceding aspects, wherein the 4-1BB agonist is an anti-CEA/anti-4-1BB bispecific antibody.

103. The method of any one of the preceding aspects, wherein the 4-1BB agonist is used in combination with a HER-2 targeting agent and wherein the combination is administered at intervals from about one week to three weeks.

104. The method of any one of the preceding aspects, wherein the 4-1BB agonist and the HER-2 targeting agent are administered together in a single composition or administered separately in two or more different compositions.

105. The method of any one of the preceding aspects, wherein the 4-1BB agonist and the HER-2 targeting agent are administered intravenously or subcutaneously.

106. The method of any one of the preceding aspects, wherein the 4-1BB agonist is administered concurrently with, prior to, or subsequently to the HER-2 targeting agent.

107. The method of any one of the preceding aspects, wherein the 4-1BB agonist and the HER-2 targeting agent are administered simultaneously.

108. A 4-1BB agonist for use in a method for treating or delaying progression of cancer of any of the preceding aspects, wherein the 4-1BB agonist is used in combination with a HER-2 targeting agent and wherein the 4-1BB agonist acts synergistically with the HER-2 targeting agent.

109. The 4-1BB agonist for use in a method for treating or delaying progression of cancer, wherein the 4-1BB agonist is used in combination with a HER-2 targeting agent and wherein a pretreatment with a Type II anti-CD20 antibody is performed prior to the combination treatment, wherein the period of time between the pretreatment and the combination treatment is sufficient for the reduction of B-cells in the individual in response to the Type II anti-CD20 antibody.

110. The 4-1BB agonist for use in a method of aspect 109, wherein the Type II anti-CD20 antibody is obinutuzumab.

111. A method for treating or delaying progression of cancer in a subject comprising administering to the subject a combination of an effective amount of a 4-1BB agonist and an effective amount of a HER-2 targeting agent, wherein a pretreatment with an Type II anti-CD20 antibody is performed prior to the treatment with the combination, wherein the period of time between the pretreatment and the combination treatment is sufficient for the reduction of B-cells in the individual in response to the Type II anti-CD20 antibody.

112. The method of aspect 111, wherein the Type II anti-CD20 antibody is obinutuzumab.

113. A combination comprising a 4-1BB (CD137) agonist and a HER-2 targeting agent, wherein the 4-1BB agonist is an antigen binding molecule comprising at least one antigen binding domain capable of specific binding to a tumor-associated antigen.

114. The combination of aspect 113, wherein the HER-2 targeting agent comprises a HER-2 antibody, a HER-2 bispecific antibody and/or a HER-2 antibody drug conjugate.

115. The combination of aspects 113 or 114, wherein the HER-2 targeting agent comprises trastuzumab, pertuzumab, and/or trastuzumab emtansine.

116. The combination of any one of the preceding aspects, wherein the 4-1BB agonist comprises three ectodomains of 4-1BBL or fragments thereof.

117. The combination of any one of the preceding aspects, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

118. The combination of any one of the preceding aspects, wherein the 4-1BB agonist is an antigen binding molecule comprising three ectodomains of 4-1BBL or fragments thereof and at least one antigen binding domain capable of specific binding to a tumor-associated antigen selected from the group consisting of Fibroblast activation protein (FAP) and CEA.

119. The combination of any one of the preceding aspects, wherein the 4-1BB agonist is an antigen binding molecule comprising an IgG Fc domain, specifically an IgG1 Fc domain or an IgG4 Fc domain.

120. The combination of any one of the preceding aspects, wherein the 4-1BB agonist is an antigen binding molecule comprising a Fc domain that comprises one or more amino acid substitution that reduces binding to an Fc receptor and/or effector function.

121. The combination of any one of the preceding aspects, wherein the 4-1BB agonist is an antigen binding molecule comprising three ectodomains of 4-1BBL or fragments thereof and at least one antigen binding domain capable of specific binding to Fibroblast activation protein (FAP).

122. The combination of any one of the preceding aspects, wherein the antigen binding domain capable of specific binding to a tumor-associated antigen is an antigen binding domain capable of specific binding to FAP comprising
(a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
(b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

123. The combination of any one of the preceding aspects, wherein the antigen binding domain capable of specific binding to a tumor-associated antigen is an antigen binding domain capable of specific binding to FAP comprising a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

124. The combination of any one of the preceding aspects, wherein the 4-1BB agonist is an antigen binding molecule comprising
(a) at least one antigen binding domain capable of specific binding to FAP,
(b) a first and a second polypeptide that are linked to each other by a disulfide bond,
wherein the first polypeptide comprises two ectodomains of 4-1BBL or fragments thereof that are connected to each other by a peptide linker and in that the second polypeptide comprises one ectodomain of 4-1BBL or a fragment thereof.

125. The combination of any one of the preceding aspects, wherein the 4-1BB agonist is an antigen binding molecule comprising
(a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region (V$_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

126. The combination of any one of the preceding aspects, wherein the 4-1BB agonist is an antigen binding molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:43 and a second light chain comprising the amino acid sequence of SEQ ID NO:44.

127. The combination of any one of the preceding aspects, wherein the 4-1BB agonist is an anti-FAP/anti-4-1BB bispecific antibody.

128. The combination of any one of the preceding aspects, wherein the 4-1BB agonist is an antigen binding molecule comprising three ectodomains of 4-1BBL or fragments thereof and at least one antigen binding domain capable of specific binding to CEA.

129. The combination of any one of the preceding aspects, wherein the antigen binding domain capable of specific binding to a tumor-associated antigen is an antigen binding domain capable of specific binding to CEA comprising (a) a heavy chain variable region (V$_H$CEA) comprising (i) CDR-H1 comprising the amino acid sequence of SEQ ID NO:33, (ii) CDR-H2 comprising the amino acid sequence of SEQ ID NO:34, and (iii) CDR-H3 comprising the amino acid sequence of SEQ ID NO:35, and a light chain variable region (V$_L$CEA) comprising (iv) CDR-L1 comprising the amino acid sequence of SEQ ID NO:36, (v) CDR-L2 comprising the amino acid sequence of SEQ ID NO:37, and (vi) CDR-L3 comprising the amino acid sequence of SEQ ID NO:38.

130. The combination of any one of the preceding aspects, wherein the antigen binding domain capable of specific binding to a tumor-associated antigen is an antigen binding domain capable of specific binding to CEA comprising a heavy chain variable region (V$_H$CEA) comprising an amino acid sequence of SEQ ID NO:39 and a light chain variable region (V$_L$CEA) comprising an amino acid sequence of SEQ ID NO:40.

131. The combination of any one of the preceding aspects, wherein the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

132. The combination of any one of the preceding aspects, wherein the 4-1BB agonist is an antigen binding molecule comprising (a) at least one Fab domain capable of specific binding to CEA comprising a heavy chain variable region (V$_H$CEA) comprising the amino acid sequence of SEQ ID NO:39 and a light chain variable region (V$_L$CEA) comprising the amino acid sequence of SEQ ID NO:40, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

133. The combination of any one of the preceding aspects, wherein the 4-1BB agonist is an anti-CEA/anti-4-1BB bispecific antibody.

134. The combination of any one of the preceding aspects for use as medicament.

135. The combination of any one of the preceding aspects, wherein the 4-1BB agonist and the HER-2 targeting agent are administered together in a single composition or administered separately in two or more different compositions.

136. The combination of any one of the preceding aspects, wherein the 4-1BB agonist and the HER-2 targeting agent are for simultaneous administration or for sequential administration.

137. The combination of any one of the preceding aspects for use in the treatment of HER-2 positive cancer.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

This section describes the characterization of the multispecific antibodies with VH/VL exchange (VH/VL CrossMabs) with emphasis on their correct assembly. The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 µg deglycosylated VH/VL CrossMabs in a Tris buffer pH 8 at room temperature for 120 hours and at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Determination of Binding and Binding Affinity of Multispecific Antibodies to the Respective Antigens Using Surface Plasmon Resonance (SPR) (BIACORE)

Binding of the generated antibodies to the respective antigens is investigated by surface plasmon resonance using a BIACORE instrument (GE Healthcare Biosciences AB, Uppsala, Sweden). Briefly, for affinity measurements Goat-Anti-Human IgG, JIR 109-005-098 antibodies are immobilized on a CM5 chip via amine coupling for presentation of the antibodies against the respective antigen. Binding is measured in HBS buffer (HBS-P (10 mM HEPES, 150 mM NaCl, 0.005% Tween 20, ph 7.4), 25° C. (or alternatively at 37° C.). Antigen (R&D Systems or in house purified) was added in various concentrations in solution. Association was measured by an antigen injection of 80 seconds to 3 minutes; dissociation was measured by washing the chip surface with HBS buffer for 3-10 minutes and a KD value was estimated using a 1:1 Langmuir binding model. Negative control data (e.g. buffer curves) are subtracted from sample curves for correction of system intrinsic baseline drift and for noise signal reduction. The respective Biacore Evaluation Software is used for analysis of sensorgrams and for calculation of affinity data.

Example 1

Preparation, Purification and Characterization of FAP-4-1BBL Antigen Binding Molecules FAP-targeted 4-1BB ligand trimer-containing Fc fusion antigen binding molecules were prepared as described in International Patent Appl. Publ. No. WO 2016/075278 A1.

In particular, the following molecules were made:

a) Monovalent FAP-Targeted and Untargeted 4-1BB Ligand Trimer-Containing Fc Fusion Antigen Binding Molecules A polypeptide encoding a dimeric 4-1BB ligand fused to human CL domain was subcloned in frame with the human IgG1 heavy chain CH2 and CH3 domains on the knob (Merchant, Zhu et al. 1998, Nature Biotechnol. 16, 677-681). A polypeptide containing one ectodomain of the 4-1BB ligand was fused to the human IgG1-CH1 domain. In Construct 2.4, in order to improve correct pairing of the chains the following mutations were additionally introduced in the crossed CH-CL (charged variant). In the dimeric 4-1BB ligand fused to human CL, E123R and Q124K, in the monomeric 4-1BB ligand fused to human CH1, K147E and K213E.

Figure 1B:
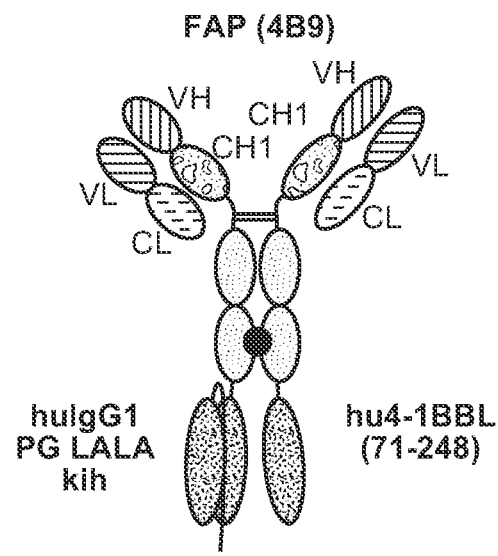
Figure 1C:
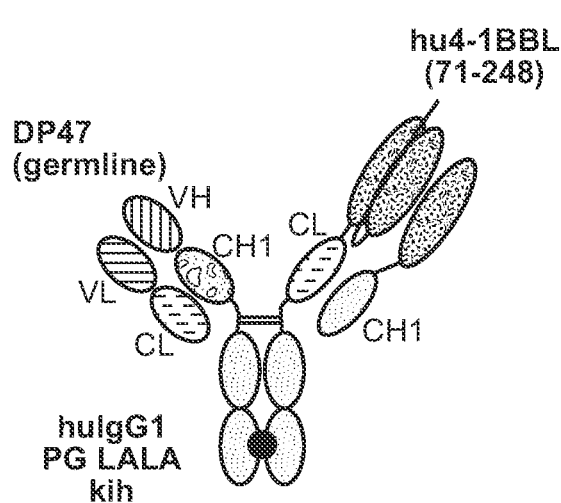

The variable region of heavy and light chain DNA sequences encoding a binder specific for FAP, clone 28H1 or clone 4B9, were subcloned in frame with either the constant heavy chain of the hole or the constant light chain of human IgG1. The Pro329Gly, Leu234Ala and Leu235Ala mutations have been introduced in the constant region of the knob and hole heavy chains to abrogate binding to Fc gamma receptors according to the method described in WO 2012/130831. Combination of the dimeric ligand-Fc knob chain containing the S354C/T366W mutations, the monomeric CH1 fusion, the targeted anti-FAP-Fc hole chain containing the Y349C/T366S/L368A/Y407V mutations and the anti-FAP light chain allows generation of a heterodimer, which includes an assembled trimeric 4-1BB ligand and a FAP binding Fab (FIG. 1A). An untargeted version has been prepared accordingly by replacing the FAP binder by germline DP47 (FIG. 1C).

TABLE 1

Monovalent Constructs

Figure 1D:
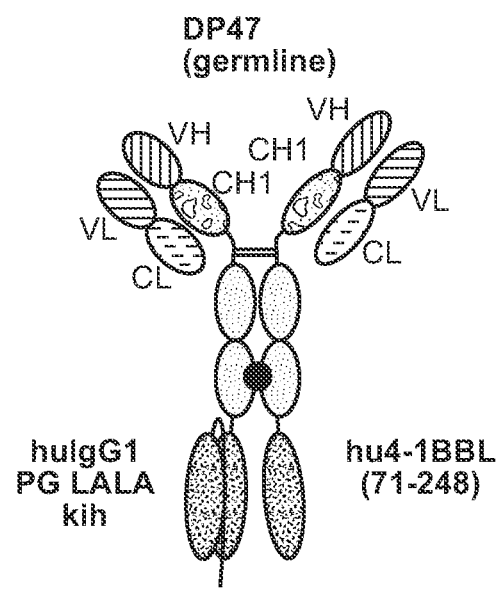

| | Example in WO 2016/075278 | composed of |
|---|---|---|
| mono FAP(4B9)-4-1BBL (Charged variant) | Example 2.1.4 (Construct 2.4) | SEQ ID NO: 41, SEQ ID NO: 42 SEQ ID NO: 43 and SEQ ID NO: 44 |
| mono FAP(28H1)-4-1BBL | Example 1.1 (Construct 1.2) | SEQ ID NO: 45, SEQ ID NO: 46 SEQ ID NO: 47 and SEQ ID NO: 48 |
| mono untargeted DP47-4-1BBL | Example 1.4 (Control B) | SEQ ID NO: 45, SEQ ID NO: 46 SEQ ID NO: 49 and SEQ ID NO: 84 | a) Bivalent FAP-Targeted and Untargeted 4-1BB Ligand Trimer-Containing Fc Fusion Antigen Binding Molecules The DNA sequences encoding the heavy and light chain variable regions of heavy and light chain specific a binder specific for FAP, clone 28H1 or clone 4B9, were subcloned in frame with either the constant heavy chain of the hole, the knob or the constant light chain of human IgG1. The Pro329Gly, Leu234Ala and Leu235Ala mutations were introduced in the constant region of the knob and hole heavy chains to abrogate binding to Fc gamma receptors according to the method described in WO 2012/130831. Furthermore, a polypeptide comprising two ectodomains of 4-1BB ligand was fused to the C-terminus of human IgG1 Fc hole chain and a polypeptide comprising one ectodomain of 4-1BB ligand was fused to the C-terminus of human IgG1 Fc knob chain. Combination of the anti-FAP huIgG1 hole dimeric ligand heavy chain containing the Y349C/T366S/L368A/Y407V mutations, the anti-FAP huIgG1 knob monomeric ligand heavy chain containing the S354C/T366W mutations and the anti-FAP light chains allowed generation of a heterodimer, which included an assembled trimeric 4-1BB ligand and two FAP binding Fabs (FIG. 1B). An untargeted version has been prepared accordingly by replacing the FAP binder by germline DP47 (FIG. 1D).

TABLE 2

Bivalent Constructs

| | Example in WO 2016/075278 | composed of |
|---|---|---|
| bi FAP(4B9)-4-1BBL | Example 2.1.3 (Construct 2.3) | 2 × SEQ ID NO: 44, SEQ ID NO: 50 and SEQ ID NO: 51 |
| bi FAP(28H1)-4-1BBL | Example 1.1 (Construct 1.5) | 2 × SEQ ID NO: 48 SEQ ID NO: 52 and SEQ ID NO: 53 |
| bi untargeted DP47-4-1BBL | Example 2.2 (Control C) | 2 × SEQ ID NO: 49 SEQ ID NO: 54 and SEQ ID NO: 55 |

The production and characterization of the FAP-targeted and untargeted 4-1BB ligand trimer-containing Fc fusion antigen binding molecules is described in detail in WO 2016/075278, Examples 1 to 6, respectively.

Example 2

Preparation, Purification and Characterization of FAP-Targeted Mouse 4-1BBL Antigen Binding Molecule (Hybrid Surrogate)

A bispecific antigen binding molecule comprising an agonistic mouse 4-1BB ligand with monovalent binding for FAP, also termed hybrid surrogate or FAP-mu4-1BBL, was prepared as described in International Patent Appl. Publ. No. WO 2016/075278 A1. The targeted mouse 4-1BBL was prepared as described for the human ligand by replacing the human ligand with the mouse ectodomain.

The DNA sequence encoding part of the ectodomain (amino acid 104-309, including the C160S mutation) of mouse 4-1BB ligand was synthetized according to the Q3U1Z9-1 sequence of Uniprot database. The FAP binder used to target the 4-1BB ligand was clone 4B9. The amino acid sequences for the hybrid surrogate FAP-mu4-1BBL can be found in Table 3.

TABLE 3

Amino acid sequences of mature hybrid surrogate FAP-mu4-1BBL

| SEQ ID NO: | Description | Sequence |
|---|---|---|
| 86 | di-mu4-1BBL-CL Fc knob chain | RTEPRPALTITTSPNLGTRENNADQVTPVSHIGCPNTTQQGSP VFAKLLAKNQASLSNTTLNWHSQDGAGSSYLSQGLRYEED KKELVVDSPGLYYVFLELKLSPTFTNTGHKVQGWVSLVLQA KPQVDDFDNLALTVELFPCSMENKLVDRSWSQLLLLKAGH RLSVGLRAYLHGAQDAYRDWELSYPNTTSFGLFLVKPDNP WEGGGGSGGGGSRTEPRPALTITTSPNLGTRENNADQVTPV SHIGCPNTTQQGSPVFAKLLAKNQASLSNTTLNWHSQDGAG SSYLSQGLRYEEDKKELVVDSPGLYYVFLELKLSPTFTNTGH KVQGWVSLVLQAKPQVDDFDNLALTVELFPCSMENKLVDR SWSQLLLLKAGHRLSVGLRAYLHGAQDAYRDWELSYPNTT SFGLFLVKPDNPWEGGGGSGGGGSRTVAAPSVFIFPPSDRKL KSGTASVVCLLNNFYPREAKVQWKVDNALQSGNSQESVTE QDSKDSTYSLSSTLTLSKADYEKHKVYACEVTHQGLSSPVT KSFNRGECDKTHTCPPCPAPEAAGGPSVFLFPPKPKDTLMIS RTPEVTCVVVDVSHEDPEVKFNWYVDGVEVHNAKTKPREE QYNSTYRVVSVLTVLHQDWLNGKEYKCKVSNKALGAPIEK TISKAKGQPREPQVYTLPPCRDELTKNQVSLWCLVKGFYPS DIAVEWESNGQPENNYKTTPPVLDSDGSFFLYSKLTVDKSR WQQGNVFSCSVMHEALHNHYTQKSLSLSPGK |
| 87 | mono-mu4-1BBL-CH1 chain | RTEPRPALTITTSPNLGTRENNADQVTPVSHIGCPNTTQQGSP VFAKLLAKNQASLSNTTLNWHSQDGAGSSYLSQGLRYEED KKELVVDSPGLYYVFLELKLSPTFTNTGHKVQGWVSLVLQA |

TABLE 3-continued

Amino acid sequences of mature hybrid surrogate FAP-mu4-1BBL

| SEQ ID NO: | Description | Sequence |
|---|---|---|
| | | KPQVDDFDNLALTVELFPCSMENKLVDRSWSQLLLLKAGH RLSVGLRAYLHGAQDAYRDWELSYPNTTSFGLFLVKPDNP WEGGGGSGGGGSASTKGPSVFPLAPSSKSTSGGTAALGCLV EDYFPEPVTVSWNSGALTSGVHTFPAVLQSSGLYSLSSVVTV PSSSLGTQTYICNVNHKPSNTKVDEKVEPKSC |
| 88 | VHCH1 (4B9) Fc hole chain | EVQLLESGGGLVQPGGSLRLSCAASGFTFSSYAMSWVRQAP GKGLEWVSAIIGSGASTYYADSVKGRFTISRDNSKNTLYLQ MNSLRAEDTAVYYCAKGWFGGFNYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDKTHTCPPCPAPEAAGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LGAPIEKTISKAKGQPREPQVCTLPPSRDELTKNQVSLSCAV KGFYPSDIAVEWESNGQPENNYKTTPPVLDSDGSFFLVSKLT VDKSRWQQGNVFSCSVMHEALHNHYTQKSLSLSPGK |
| 89 | VLCL(4B9) Light chain | EIVLTQSPGTLSLSPGERATLSCRASQSVTSSYLAWYQQKPG QAPRLLINVGSRRATGIPDRFSGSGSGTDFTLTISRLEPEDFA VYYCQQGIMLPPTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |

The hybrid surrogate FAP-mu4-1BBL was produced by co-transfecting CHO-K1 cells growing in suspension with the mammalian expression vectors using eviFect (Evitria AG). The cells were transfected with the corresponding expression vectors in a 1:1:1:1 ratio ("vector Fc-hole heavy chain":"vector FAP light chain":"vector 4-1BBL Fc-knob heavy chain":"vector mu4-1BBL light chain").

For transfection CHO-K1 cells are cultivated in suspension serum free in eviMake culture medium (Evitria AG). After 7 days at 37° C. in an incubator with a 5% CO$_2$ atmosphere, cultivation supernatant is collected for purification by centrifugation and the solution is sterile filtered (0.22 mm filter) and kept at 4° C.

Secreted proteins were purified from cell culture supernatants by affinity chromatography using Protein A, followed by size exclusion chromatography. For affinity chromatography, the supernatant was loaded on a Protein A MabSelectSure column (GE Healthcare) equilibrated with 20 mM sodium phosphate, 20 mM sodium citrate pH 7.5. Unbound protein was removed by washing with 20 mM sodium phosphate, 20 mM sodium citrate containing buffer (pH 7.5). The bound protein was eluted using a linear pH-gradient of sodium chloride of 20 mM sodium citrate, 100 mM NaCl, 100 mM Glycine, 0.01% Tween20 pH 3.0. The column was then washed with 20 mM sodium citrate, 100 mM NaCl, 100 mM Glycine, 0.01% Tween20 pH 3.0. The pH of collected fractions was adjusted by adding ⅟₄₀ (v/v) of 2M Tris, pH8.0. The protein was concentrated and filtered prior to loading on a HiLoad Superdex column (GE Healthcare) equilibrated with 20 mM Histidine, 140 mM NaCl, 0.01% Tween20 pH6.0.

The protein concentration of purified bispecific constructs was determined by measuring the OD at 280 nm, using the molar extinction coefficient calculated on the basis of the amino acid sequence. Purity and molecular weight of the bispecific constructs were analyzed by CE-SDS in the presence and absence of a reducing agent (Invitrogen, USA) using a LabChipGXII (Caliper). The aggregate content of bispecific constructs was analyzed using a TSKgel G3000 SW XL analytical size-exclusion column (Tosoh) equilibrated in a 25 mM K2HPO4, 125 mM NaCl, 200 mM L-Arginine Monohydrocloride, 0.02% (w/v) NaN$_3$, pH 6.7 running buffer at 25° C.

TABLE 4

Biochemical analysis of hybrid surrogate FAP-mu4-1BBL

| Molecule | Monomer [%] | Yield [mg/l] | CE-SDS (non-red) |
|---|---|---|---|
| FAP-mu4-1BBL | 95 | 3.2 | 92 |

2.1 Functional Characterization of Hybrid Surrogate FAP-mu4-1BBL by Surface Plasmon Resonance The capacity of binding simultaneously murine 4-1BB Fc(kih) and human or murine FAP was assessed by surface plasmon resonance (SPR) in the manner as described in WO 2016/075278 A1. All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). Biotinylated murine 4-1BB Fc(kih) was directly coupled to a flow cell of a streptavidin (SA) sensor chip. Immobilization levels up to 600 resonance units (RU) were used.

The FAP-targeted mu4-1BBL construct was passed at a concentration range of 200 nM with a flow of 30 µL/minute through the flow cells over 90 seconds and dissociation was set to zero sec. Human or murine FAP was injected as second analyte with a flow of 30 µL/minute through the flow cells over 90 seconds at a concentration of 500 nM. The dissociation was monitored for 120 sec. Bulk refractive index differences were corrected for by subtracting the response obtained in a reference flow cell, where no protein was immobilized.

Figure 2A:
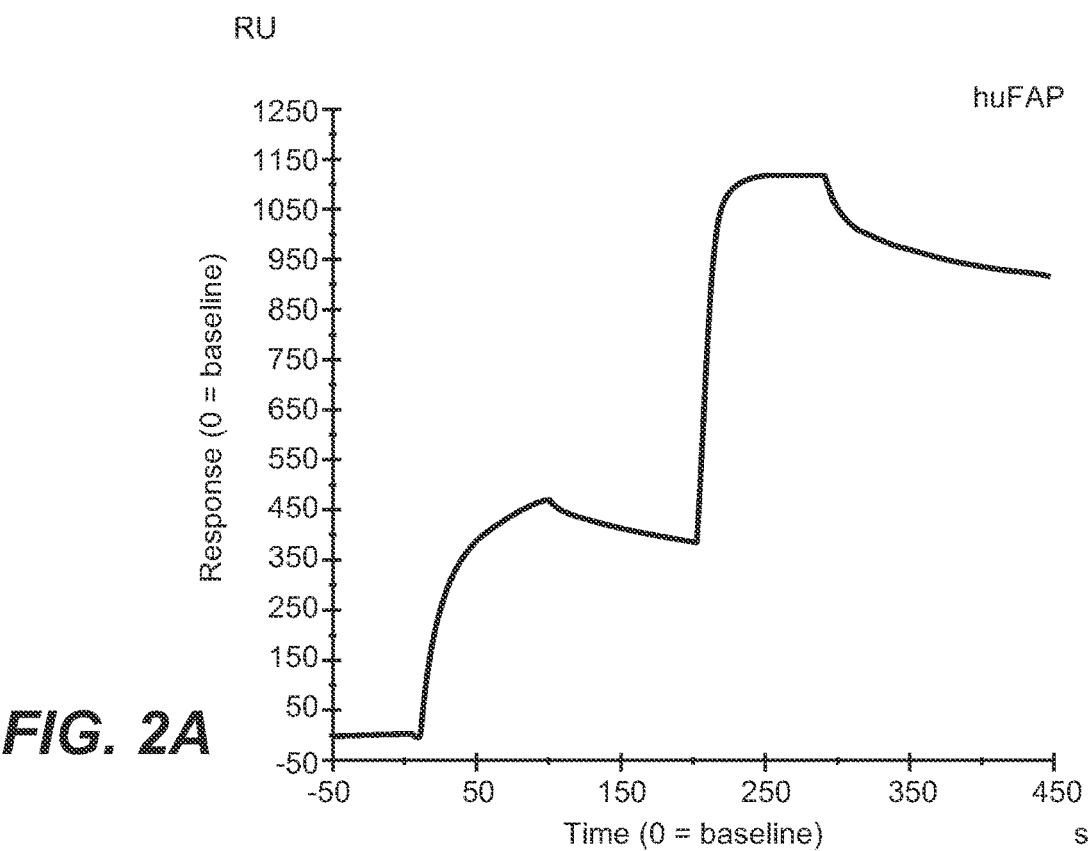
FIG. 2A and FIG. 2B show the simultaneous binding of hybrid surrogate FAP-mu4-1BBL (Analyte 1) to immobilized murine 4-1BB and human FAP or murine FAP (Analyte 2), respectively.
Figure 2B:
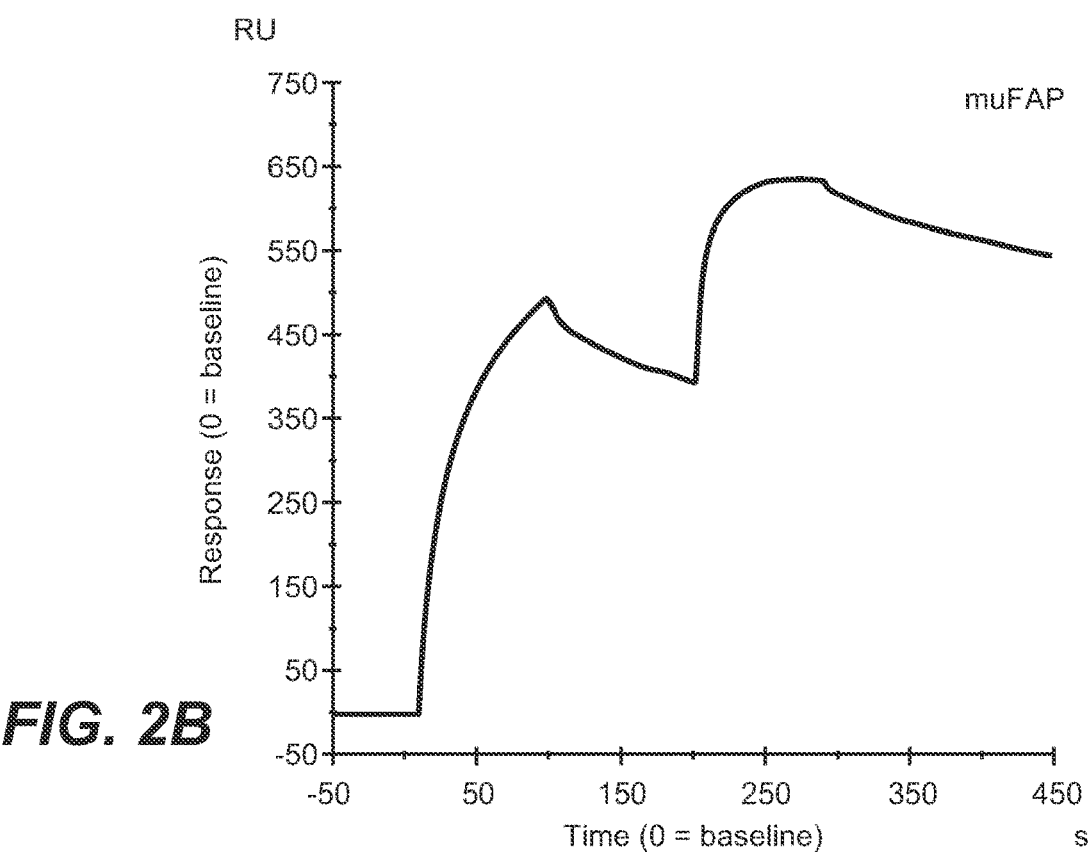

As can be seen in the graphs of FIG. 2A and FIG. 2B, the hybrid surrogate FAP-mu4-1BBL can bind simultaneously murine 4-1BB and murine/human FAP.

Example 3

Preparation, Purification and Characterization of Bispecific Antigen Binding Molecules with Bivalent Binding to Mouse 4-1BB and Monovalent Binding to FAP Bispecific agonistic mouse 4-1BB antibodies with bivalent binding for 4-1BB and monovalent binding for FAP, also termed 2+1, have been prepared in analogy to FIG. 1A, FIG. 1B, FIG. 1C, and FIG. 1D. In this example, the first heavy chain HC1 of the construct was comprised of the following components: VHCH1 of an anti-4-1BB (clone MU137-1) followed by Fc containing the mutations Lys392Asp and Lys409Asp (termed Fc-DD), at which C-terminus a VL, or VH, of anti-FAP binder (clone 28H1) was fused. The second heavy chain HC2 was comprised of VHCH1 of anti-4-1BB (clone MU137-1) followed by Fc containing the mutation Glu356Lys and Asp399Lys (termed Fc-KK), at which C-terminus a VH, or VL, of anti-FAP binder (clone 28H1) was fused. The DDKK mutations for enhancing antibody Fc heterodimer formation are inter alia described by Gunasekaran et al., J. Biol. Chem. 2010, 19637-19646. Combination of the targeted anti-FAP-Fc DD with the anti-4-1BB-Fc KK chain allows generation of a heterodimer, which includes a FAP binding moiety and two murine mouse 4-1BB binding Fabs. DAPG mutations were introduced in the constant regions of the heavy chains to abrogate binding to mouse Fc gamma receptors according to the method described e.g. in Baudino et al. J. Immunol. (2008), 181, 6664-6669, or in WO 2016/030350 A1. Briefly, the Asp265Ala and Pro329Gly mutations have been introduced in the constant region of the Fc-DD and Fc-KK heavy chains to abrogate binding to Fc gamma receptors (numbering according to Kabat EU index; i.e. D265A, P329G).

The amino acid sequences for 2+1 anti-4-1BB(MU137-1), anti-FAP(28H1) construct with a-FAP(28H1) VH fused to Fc-KK and VL fused to Fc-DD chain can be found respectively in Table 5. The amino acid sequences for 2+1 anti-4-1BB(MU137-1), anti-FAP(28H1) construct with a-FAP(28H1) VL fused to Fc-KK and VH fused to Fc-DD chain can be found respectively in Table 6.

TABLE 5

Sequences of bispecific, bivalent anti-4-1BB (MU137-1)/anti-FAP (28H1) mouse IgG1 DAPG antigen binding molecules (Constructs with FAP VL fused to Fc-DD chain and VH fused to Fc-KK chain, also termed below Fc-DD-VL)

| SEQ ID NO: | Description | Sequence |
|---|---|---|
| 90 | VHCH1 (MU137-1)-Heavy chain Fc-DD-VL (28H1) | DVQLVESGGGLVQPGRSLKLSCAASGFIFSYFDMAWVRQAP TKGLEWVASISPSGDIPYYRDSVKGRFTVSRENAKSSLYLQM DSLRSEDTATYYCARRSYGGYSELDYWGQGVMVTVSSAKT TPPSVYPLAPGSAAQTNSMVTLGCLVKGYFPEPVTVTWNSG SLSSGVHTFPAVLQSDLYTLSSSVTVPSSTWPSQTVTCNVAH PASSTKVDKKIVPRDCGCKPCICTVPEVSSVFIFPPKPKDVLTI TLTPKVTCVVVAISKDDPEVQFSWFVDDVEVHTAQTKPREE QINSTFRSVSELPIMHQDWLNGKEFKCRVNSAAFGAPIEKTIS KTKGRPKAPQVYTIPPPKEQMAKDKVSLTCMITNFFPEDITV EWQWNGQPAENYDNTQPIMDTDGSYFVYSDLNVQKSNWE AGNTFTCSVLHEGLHNHHTEKSLSHSPGGGGSGGGGSGGG GSGGGGSEIVLTQSPGTLSLSPGERATLSCRASQSVSRSYLA WYQQKPGQAPRLLIIGASTRATGIPDRFSGSGSGTDFTLTISR LEPEDFAVYYCQQGQVIPPTFGQGTKVEIK |
| 91 | VHCH1 (20H4.9)-Heavy chain Fc-KK-VH (28H1) | DVQLVESGGGLVQPGRSLKLSCAASGFIFSYFDMAWVRQAP TKGLEWVASISPSGDIPYYRDSVKGRFTVSRENAKSSLYLQM DSLRSEDTATYYCARRSYGGYSELDYWGQGVMVTVSSAKT TPPSVYPLAPGSAAQTNSMVTLGCLVKGYFPEPVTVTWNSG SLSSGVHTFPAVLQSDLYTLSSSVTVPSSTWPSQTVTCNVAH PASSTKVDKKIVPRDCGCKPCICTVPEVSSVFIFPPKPKDVLTI TLTPKVTCVVVAISKDDPEVQFSWFVDDVEVHTAQTKPREE QINSTFRSVSELPIMHQDWLNGKEFKCRVNSAAFGAPIEKTIS KTKGRPKAPQVYTIPPPKKQMAKDKVSLTCMITNFFPEDITV EWQWNGQPAENYKNTQPIMKTDGSYFVYSKLNVQKSNWE AGNTFTCSVLHEGLHNHHTEKSLSHSPGGGGSGGGGSGGG GSGGGGSEVQLLESGGGLVQPGGSLRLSCAASGFTFSSHAM SWVRQAPGKGLEWVSAIWASGEQYYADSVKGRFTISRDNS KNTLYLQMNSLRAEDTAVYYCAKGWLGNFDYWGQGTLVT VSS |
| 92 | VLCL-Light chain (MU137-1) | DIQMTQSPASLSASLEEIVTITCQASQDIGNWLAWYHQKPGK SPQLLIYGTSSLADGVPSRFSGSSSGSQYSLKISRLQVEDIGIY YCLQAYGAPWTFGGGTKLELKRADAAPTVSIFPPSSEQLTSG GASVVCFLNNFYPKDINVKWKIDGSERQNGVLNSWTDQDS KDSTYSMSSTLTLTKDEYERHNSYTCEATHKTSTSPIVKSFN RNEC |

TABLE 6

Sequences of bispecific, bivalent anti-4-1BB (MU137-1)/
monovalent anti-FAP (28H1) mouse IgG1 DAPG antigen binding
molecules (Constructs with FAP VH fused to Fc DD chain and
VL fused to Fc KK chain, termed Fc-DD-VH)

| SEQ ID NO: | Description | Sequence |
|---|---|---|
| 93 | VHCH1 (MU137-1)-Heavy chain Fc-DD-VH (28H1) | DVQLVESGGGLVQPGRSLKLSCAASGFIFSYFDMAWVRQAP TKGLEWVASISPSGDIPYYRDSVKGRFTVSRENAKSSLYLQM DSLRSEDTATYYCARRSYGGYSELDYWGQGVMVTVSSAKT TPPSVYPLAPGSAAQTNSMVTLGCLVKGYFPEPVTVTWNSG SLSSGVHTFPAVLQSDLYTLSSSVTVPSSTWPSQTVTCNVAH PASSTKVDKKIVPRDCGCKPCICTVPEVSSVFIFPPKPKDVLTI TLTPKVTCVVVAISKDDPEVQFSWFVDDVEVHTAQTKPREE QINSTFRSVSELPIMHQDWLNGKEFKCRVNSAAFGAPIEKTIS KTKGRPKAPQVYTIPPPKEQMAKDKVSLTCMITNFFPEDITV EWQWNGQPAENYDNTQPIMDTDGSYFVYSDLNVQKSNWE AGNTFTCSVLHEGLHNHHTEKSLSHSPGGGGGSGGGGSGGG GSGGGGSEVQLLESGGGLVQPGGSLRLSCAASGFTFSSHAM SWVRQAPGKGLEWVSAIWASGEQYYADSVKGRFTISRDNS KNTLYLQMNSLRAEDTAVYYCAKGWLGNFDYWGQGTLVT VSS |
| 94 | VHCH1 (MU137-1)-Heavy chain Fc-KK-VL (28H1) | DVQLVESGGGLVQPGRSLKLSCAASGFIFSYFDMAWVRQAP TKGLEWVASISPSGDIPYYRDSVKGRFTVSRENAKSSLYLQM DSLRSEDTATYYCARRSYGGYSELDYWGQGVMVTVSSAKT TPPSVYPLAPGSAAQTNSMVTLGCLVKGYFPEPVTVTWNSG SLSSGVHTFPAVLQSDLYTLSSSVTVPSSTWPSQTVTCNVAH PASSTKVDKKIVPRDCGCKPCICTVPEVSSVFIFPPKPKDVLTI TLTPKVTCVVVAISKDDPEVQFSWFVDDVEVHTAQTKPREE QINSTFRSVSELPIMHQDWLNGKEFKCRVNSAAFGAPIEKTIS KTKGRPKAPQVYTIPPPKKQMAKDKVSLTCMITNFFPEDITV EWQWNGQPAENYKNTQPIMKTDGSYFVYSKLNVQKSNWE AGNTFTCSVLHEGLHNHHTEKSLSHSPGGGGGSGGGGSGGG GSGGGGSEIVLTQSPGTLSLSPGERATLSCRASQSVSRSYLA WYQQKPGQAPRLLIIGASTRATGIPDRFSGSGSGTDFTLTISR LEPEDFAVYYCQQGQVIPPTFGQGTKVEIK |
| 92 | VLCL-Light chain (MU137-1) | see Table 5 |

The bispecific 2+1 anti-4-1BB anti-FAP muIgG1 DAPG was produced by co-transfecting CHO-K1 cells growing in suspension with the mammalian expression vectors using eviFect (Evitria AG). The cells were transfected with the corresponding expression vectors in a 1:1:1 ratio ("vector Fc-DD heavy chain":"vector light chain":"vector Fc-KK heavy chain").

For transfection CHO-K1 cells are cultivated in suspension serum free in eviMake (Evitria AG) culture medium. After 7 days at 37° C. in an incubator with a 5% CO$_2$ atmosphere, cultivation supernatant is collected for purification by centrifugation and the solution is sterile filtered (0.22 mm filter) and kept at 4° C.

Secreted proteins were purified from cell culture supernatants by affinity chromatography using Protein A, followed by size exclusion chromatography. For affinity chromatography, the supernatant was loaded on a Protein A MabSelectSure column (CV=5 mL, GE Healthcare) equilibrated with 40 mL 20 mM sodium phosphate, 20 mM sodium citrate pH 7.5. Unbound protein was removed by washing with at least 10 column volumes of 20 mM sodium phosphate, 20 mM sodium citrate containing buffer (pH 7.5). The bound protein was eluted using a linear pH-gradient of sodium chloride (from 20 to 100 mM) created over 15 column volumes of 20 mM sodium citrate, 100 mM NaCl, 100 mM Glycine, pH 3.0. The column was then washed with 10 column volumes of 20 mM sodium citrate, 100 mM NaCl, 100 mM Glycine, pH 3.0. The pH of collected fractions was adjusted by adding 1/40 (v/v) of 2M Tris, pH8.0. The protein was concentrated and filtered prior to loading on a HiLoad Superdex 16/600 S200 column (GE Healthcare) equilibrated with 20 mM Histidine, 140 mM NaCl, pH6.0.

The protein concentration of purified bispecific constructs was determined by measuring the OD at 280 nm, using the molar extinction coefficient calculated on the basis of the amino acid sequence. Purity and molecular weight of the bispecific constructs were analyzed by CE-SDS in the presence and absence of a reducing agent (Invitrogen, USA) using a LabChipGXII (Caliper). The aggregate content of bispecific constructs was analyzed using a TSKgel G3000 SW XL analytical size-exclusion column (Tosoh) equilibrated in a 25 mM K$_2$HPO$_4$, 125 mM NaCl, 200 mM L-Arginine Monohydrochloride, 0.02% (w/v) NaN3, pH 6.7 running buffer at 25° C.

TABLE 7

Biochemical analysis of bispecific antigen binding molecules with a bivalent binding to 4-1BB and a monovalent binding to FAP (2 + 1) anti-4-1BB (MU137-1), anti-FAP(28H1) mouse IgG1 DAPG

| Molecule | Monomer [%] | Yield [mg/l] | CE-SDS (non-red) |
|---|---|---|---|
| 4-1BB (MU137-1)/FAP(28H1) DAPG IgG1 2 + 1 (Fc-DD-VL), in the following named muFAP-4-1BB | 98 | 3.6 | 92 |

3.1 Functional Characterization of Mouse Surrogate muFAP-4-1BB by Surface Plasmon Resonance The capacity of binding simultaneously murine 4-1BB Fc(kih) and murine FAP was assessed by surface plasmon resonance (SPR) in the manner as described in WO 2016/075278 A1. All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). Biotinylated murine 4-1BB Fc(kih) was directly coupled to a flow cell of a streptavidin (SA) sensor chip. Immobilization levels up to 600 resonance units (RU) were used.

Figure 2C:
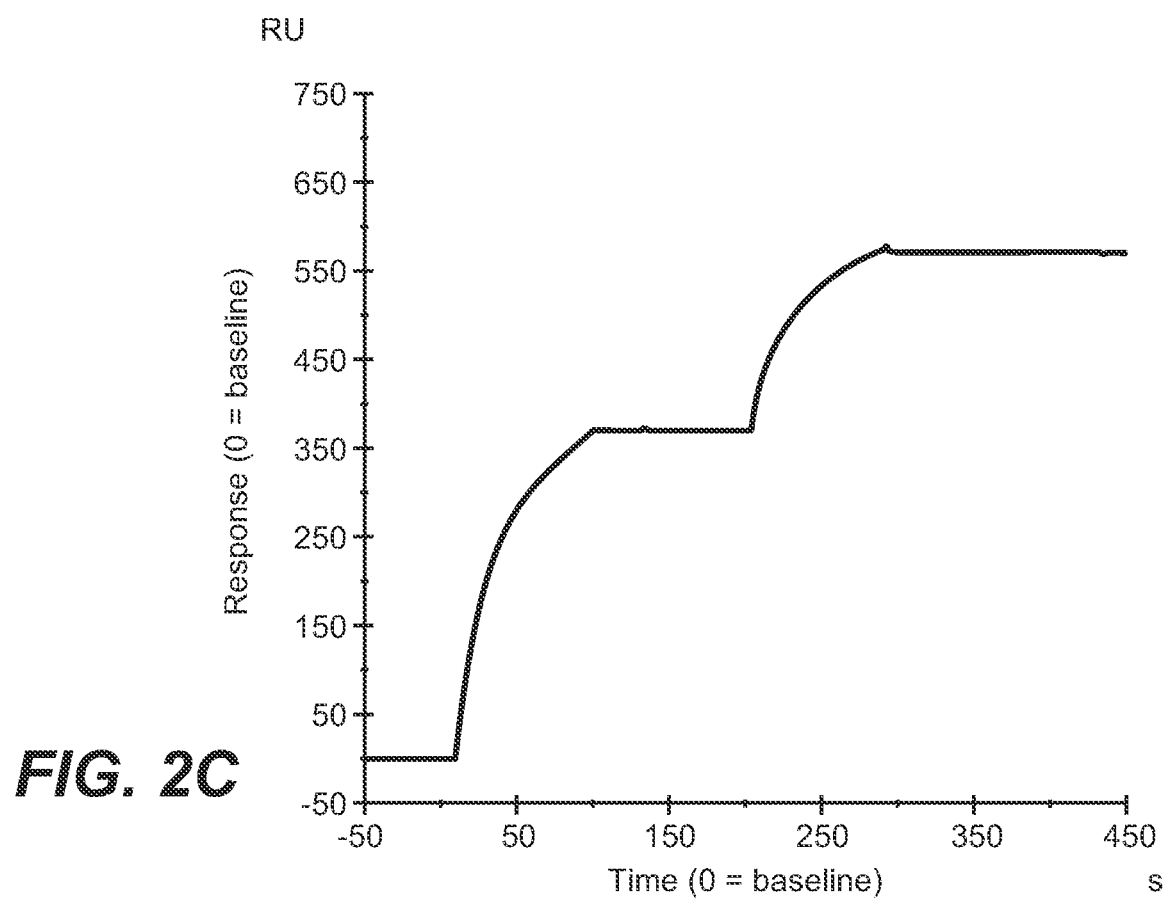
In FIG. 2C is shown the simultaneous binding of murine bispecific FAP-4-1BB antibody muFAP-4-1BB (Analyte 1) to immobilized murine 4-1BB and murine FAP (Analyte 2).

The FAP-targeted 4-1BB constructs were passed at a concentration range of 200 nM with a flow of 30 µL/minute through the flow cells over 90 seconds and dissociation was set to zero sec. Murine FAP was injected as second analyte with a flow of 30 µL/minute through the flow cells over 90 seconds at a concentration of 500 nM. The dissociation was monitored for 120 sec. Bulk refractive index differences were corrected for by subtracting the response obtained in a reference flow cell, where no protein was immobilized. As can be seen in the graph of FIG. 2C, the mouse surrogate muFAP-4-1BB can bind simultaneously murine 4-1BB and murine FAP.

Example 4

Figure 3:
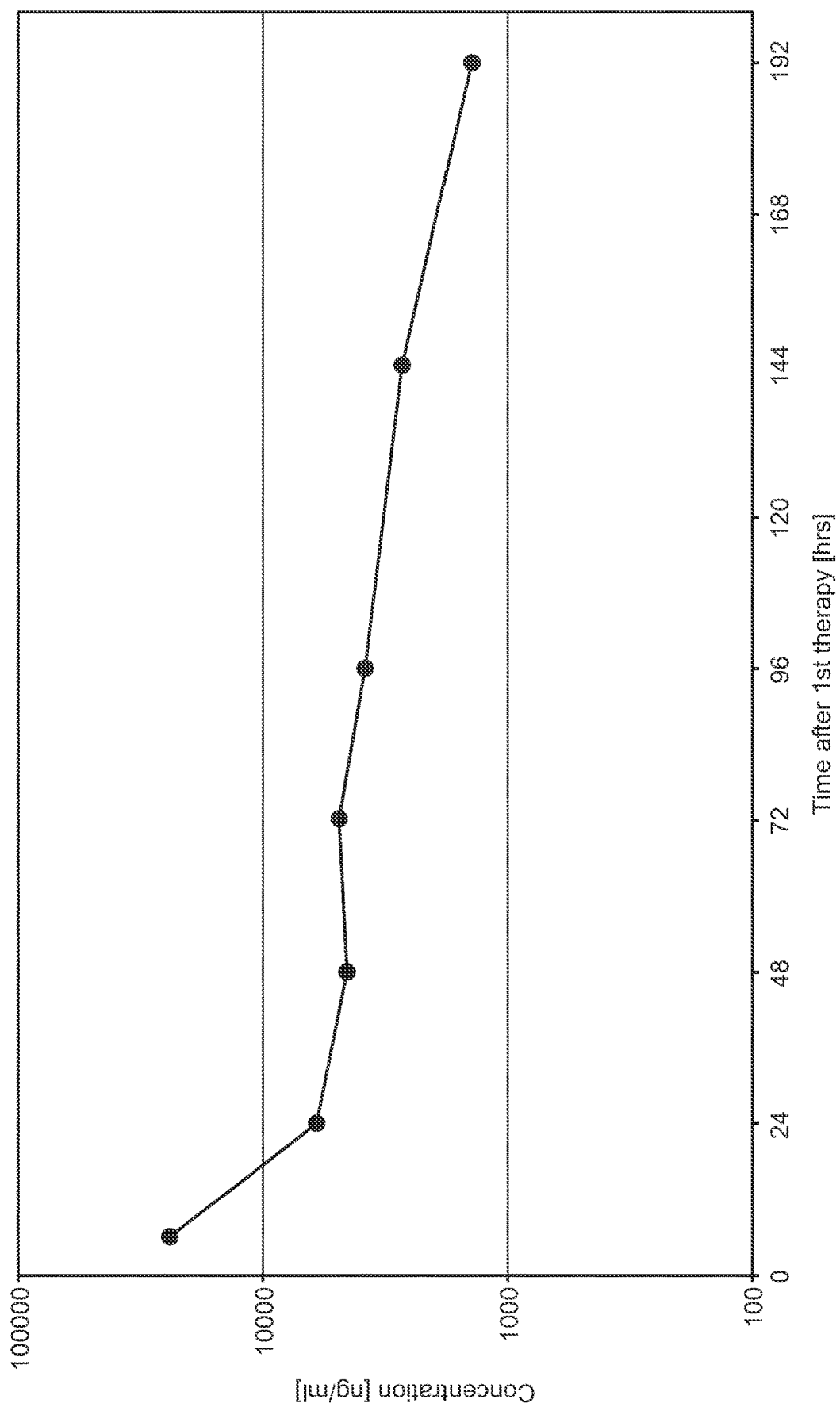
FIG. 3 shows the pharmacokinetic profile of muFAP-4-1BB after single injection in C57BL/6 mice as described in Example 4. A stable PK-behavior was observed which suggests that the compound can be administered in a once weekly schedule.

Pharmacokinetic Profile of muFAP-4-1BB after Single Injection in C57BL/6 Mice A single dose of 2.5 mg/kg of muFAP-4-1BB (prepared according to Example 3) was injected into C57BL/6 mice. All mice were injected i.v. with 200 µl of the appropriate solution. To obtain the proper amount of compounds per 200 µl, the stock solution (muFAP-4-1BB; 1.81 mg/mL in 20 mM Histidine, 140 mM NaCl, pH 6.0) was diluted with histidine buffer. Three mice per time point were bled at 10 min, 1 hr, 6 hr, 24 hr, 48 hr, 72 hr, 96 hr, 6 days and 9 days. The injected compound was analyzed in serum samples by ELISA. Biotinylated murine 4-1BB, test serum sample, detection antibody anti-msIgG labelled with HRP were added stepwise to a 96-well streptavidin-coated microtiter plate and incubated after every step for 1 h at room temperature. The plate was washed three times after each step to remove unbound substances. Finally, the peroxidase-bound complex was visualized by adding ABTS substrate solution to form a colored reaction product. The reaction product intensity was photometrically determined at 405 nm (with reference wavelength at 490 nm) and was proportional to the analyte concentration in the serum sample. The result is shown in FIG. 3. muFAP-4-1BB showed a stable PK-behavior which suggested a once weekly schedule for efficacy studies.

Example 5

In Vivo Anti-Tumor Efficacy of Hybrid FAP-mu4-1BBL Construct in Combination with Trastuzumab The first proof of concept for the combination of hybrid FAP-mu4-1BBL (anti-FAP, mouse 4-1BBL, human IgG backbone) and Trastuzumab was carried out in tumor-bearing (N87-bearing) huCD16TgScid mice.

N87 cells (Her2+ human gastric carcinoma) were originally obtained from ATCC and after expansion deposited in the Roche Glycart internal cell bank. Cells were cultured in RPMI containing 10% FCS and 1% Glutamax. The cells were cultured at 37° C. in a water-saturated atmosphere at 5% $CO_2$. $5 \times 10^6$ cells per animal were injected subcutaneously into the right flank of the animals in RPMI cell culture medium (Gibco) and GFR matrigel (1:1, total volume of 100 µl) at a viability of >95.0%.

Human FcgRIIIa (CD16) transgenic SCID mice (which express both murine FcγRIV-positive macrophages and human FcγRIIIa-positive transgenic murine NK cells as effectors) aged 8-10 weeks at start of the experiment (bred at Charles River, France) were maintained under specific-pathogen-free condition with daily cycles of 12 h light/12 h darkness according to committed guidelines (GV-Solas; Felasa; TierschG). The experimental study protocol was reviewed and approved by local government. After arrival, animals were maintained for one week to get accustomed to the new environment and for observation. Continuous health monitoring was carried out on a regular basis.

According to the protocol (FIG. 4A), female huCD16TgScid mice were injected with tumor cells subcutaneously as described above and treated once weekly with the compounds or PBS (Vehicle) when tumor size reached appr. 220 $mm^3$ (day 28). All mice were injected intravenously with 200 µl of the appropriate solution once per week. To obtain the proper amount of compounds per 200 µl, the stock solutions (Table 1) were diluted with histidine buffer when necessary. For combination therapy (Group D, FIG. 4B) with Trastuzumab and FAP-4-1BBL constructs, therapies were injected concomitant. Tumor growth was measured twice weekly using a caliper (FIG. 5A and FIG. 5B) and tumor volume was calculated as followed:

$$T_v : (W^2/2) \times L \quad (W: \text{Width}, L: \text{Length})$$

Figure 5A:
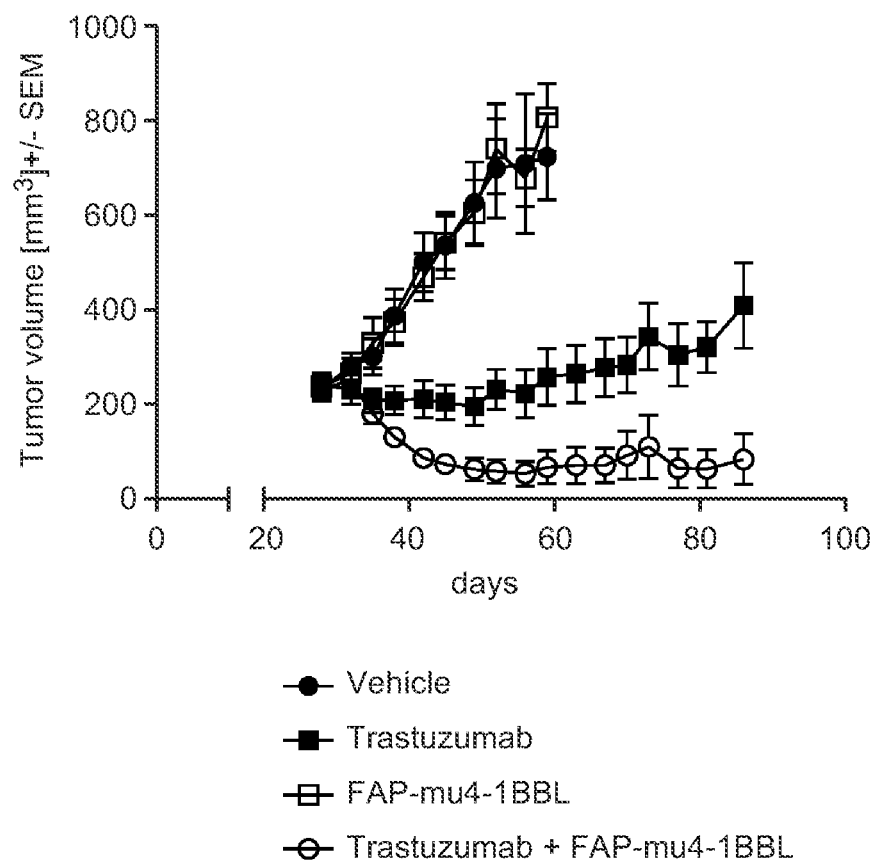
FIG. 5A shows the tumor growth kinetics (Mean+/−SEM) as observed in mice treated with trastuzumab alone, hybrid FAP-mu4-1BBL alone, or with the combination of both. The individual tumor growth kinetics of each animal for all treatment groups are shown in FIG. 5B (control group), FIG. 5C (treatment with trastuzumab alone), FIG. 5D (treatment with FAP-mu4-1BBL alone) and FIG. 5E (treatment with the combination). The number of tumor-free mice at study termination is indicated.
Figure 5B:
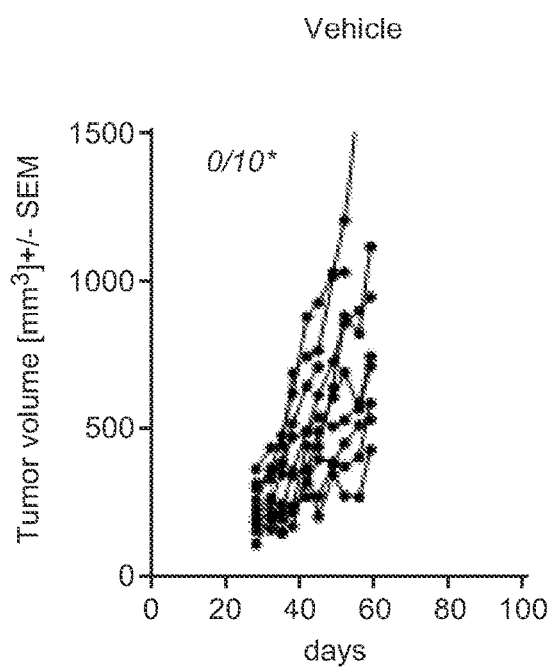
Figure 5C:
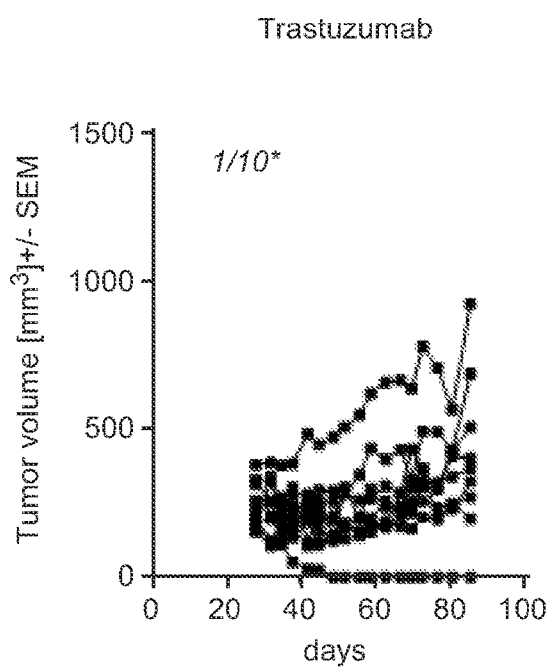
Figure 5D:
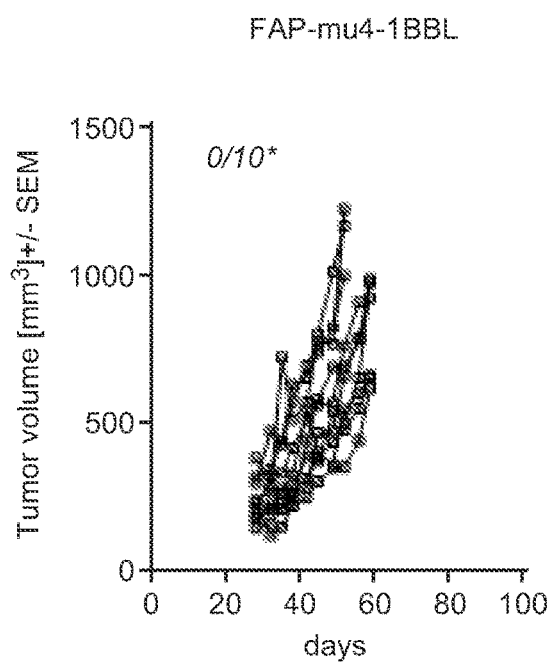
Figure 5E:
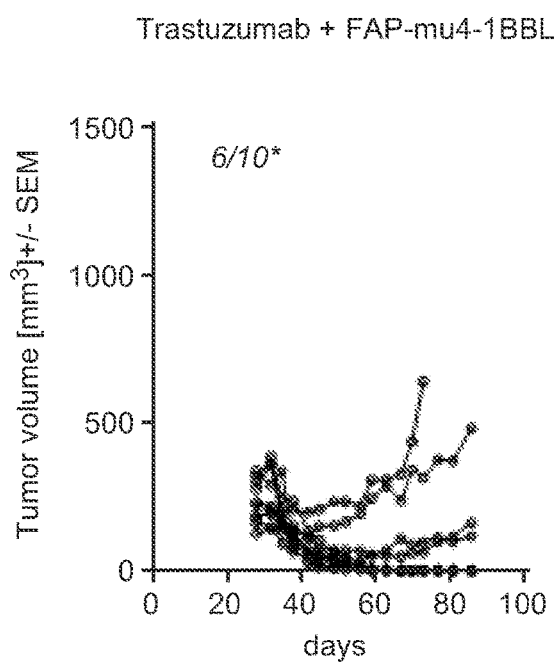

Study was terminated and all mice were sacrificed after eight injections of the compounds (day 86 after tumor cell injection). FIG. 5A and FIG. 5B show the tumor growth kinetics (Mean+/−SEM) in all treatment groups as well as the individual tumor growth kinetics of each animal for all groups. Monotherapy of hybrid FAP-mu4-1BBL didn't reveal any tumor growth inhibition. Trastuzumab, given as monotherapy, induced tumor stasis (TGI: 95 and TCR: 0.35) with one mouse being tumor free at study termination. However, the combination of Trastuzumab and hybrid FAP-mu4-1BBL induced strong tumor regression (TGI: 132 and TCR: 0.09) resulting in 60% tumor free mice by day 86.

Statistical analysis was carried out using JMP software:

$$TGI: \frac{100 - Av(T\_treatment^{[day\,x]} - T\_treatment^{[baseline]})}{Av(T\_Vehicle^{[day\,x]} - T\_Vehicle^{[baseline]})} * 100$$

$$TCR: \frac{Av(T\_treatment^{[day\,x]})}{Av(T\_Vehicle^{[day\,x]})}$$

The calculations based on day 59 of the study are shown in Table 9 below.

TABLE 8

Compositions used in the in vivo experiments

| Compound | Formulation buffer | Concentration (mg/mL) |
|---|---|---|
| FAP-mu4-1BBL | 20 mM Histidine, 140 mM NaCl, pH 16. 0 | 5.33 (= stock solution) |

TABLE 8-continued

Compositions used in the in vivo experiments

| Compound | Formulation buffer | Concentration (mg/mL) |
|---|---|---|
| Trastuzumab | 20 mM Histidine, 140 mM NaCl, pH 6.0 | 25 (= stock solution) |

TABLE 9

Tumor Growth Inhibition (TGI) and TCR on day 59

| Group | TGI | TCR |
|---|---|---|
| Trastuzumab | 95 | 0.46 |
| FAP-mu4-1BBL | −17 | 0.99 |
| Trastuzumab + FAP-mu4-1BBL | 132 | 0.23 |

TGI: Tumor Growth Inhibition => TGI > 100 means tumor regression, TGI = 100 means tumor stasis;
TCR: Treatment to Control Ratio => TCR = 1 means no effect, TCR = means complete tumor regression Example 6

Preparation, Purification and Characterization of CEA-4-1BBL Antigen Binding Molecules CEA-targeted 4-1BB ligand trimer-containing Fc fusion antigen binding molecules were prepared as described in International Patent Appl. Publ. No. WO 2016/075278 A1.

In particular, monovalent CEA-targeted and untargeted 4-1BB ligand trimer-containing Fc fusion antigen binding molecules were made.

A polypeptide encoding a dimeric 4-1BB ligand fused to the human CL domain was subcloned in frame with the human IgG1 heavy chain CH2 and CH3 domains on the knob (Merchant, Zhu et al. 1998, Nature Biotechnol. 16, 677-681). A polypeptide containing one ectodomain of the 4-1BB ligand was fused to the human IgG1-CH1 domain. In order to improve correct pairing of the chains the following mutations were additionally introduced in the crossed CH-CL (charged variant): In the dimeric 4-1BB ligand fused to human CL, E123R and Q124K, in the monomeric 4-1BB ligand fused to human CH1, K147E and K213E.

The variable region of heavy and light chain DNA sequences encoding a binder specific for CEA, clone T84.66-LCHA (CEACAM5), were subcloned in frame with either the constant heavy chain of the hole or the constant light chain of human IgG1. The Pro329Gly, Leu234Ala and Leu235Ala mutations were introduced in the constant region of the knob and hole heavy chains to abrogate binding to Fc gamma receptors according to the method described in WO 2012/130831. Combination of the dimeric ligand-Fc knob chain containing the S354C/T366W mutations, the monomeric CH1 fusion, the targeted anti-CEA-Fc hole chain containing the Y349C/T366S/L368A/Y407V mutations and the anti-CEA light chain allows generation of a heterodimer, which includes an assembled trimeric 4-1BB ligand and a CEA binding Fab (in analogy to FIG. 1A, anti-FAP replaced by anti-CEA).

TABLE 10

| Monovalent Construct | | |
|---|---|---|
| | Example in WO 2016/075278 | composed of |
| mono CEA (T84.66-LCHA)-4-1BBL (Charged variant) | Example 11.2.4 (Construct 5.4) | SEQ ID NO: 41, SEQ ID NO: 42 SEQ ID NO: 82 and SEQ ID NO: 83 |

The production and characterization of the CEA-targeted and untargeted 4-1BB ligand trimer-containing Fc fusion antigen binding molecules is described in detail in WO 2016/075278, Examples 11 to 13, respectively.

The invention claimed is:

1. A method for treating or delaying progression of a HER2-positive cancer in a subject comprising administering to the subject an effective amount of a 4-1BB agonist and an effective amount of a HER-2 targeting agent, wherein the HER-2 targeting agent is trastuzumab, pertuzumab, and/or trastuzumab emtansine, wherein the 4-1BB agonist is an antigen binding molecule comprising at least one antigen binding domain capable of specific binding to a tumor-associated antigen, wherein the 4-1BB agonist is a molecule comprising three ectodomains of 4-1BBL or 4-1BB-binding fragments thereof and wherein the ectodomains of 4-1BBL comprise the amino acid sequence of SEQ ID NO:1, SEQ ID NO: 2, SEQ ID NO:3, SEQ ID NO:4, SEQ ID NO:5, SEQ ID NO: 6, SEQ ID NO:7 or SEQ ID NO:8 and an IgG1 Fc domain comprising the amino acid substitutions L234A, L235A and P329G, as numbered according to EU numbering.

2. The method of claim 1, wherein the 4-1BB agonist and the HER-2 targeting agent are administered together in a single composition or administered separately in two or more different compositions.

3. The method of claim 1, wherein the 4-1BB agonist and the HER-2 targeting agent are administered intravenously or subcutaneously.

4. The method of claim 1, wherein the 4-1BB agonist is administered concurrently with, prior to, or subsequently to the HER-2 targeting agent.

5. The method of claim 1, wherein the 4-1BB agonist is an antigen binding molecule comprising at least one antigen binding domain capable of specific binding to a tumor-associated antigen.

6. The method of claim 1, wherein the 4-1BB agonist is an antigen binding molecule comprising at least one antigen binding domain capable of specific binding to a tumor-associated antigen selected from the group consisting of Fibroblast activation protein (FAP) and Carcinoembryonic Antigen (CEA).

7. The method of claim 1, wherein the 4-1BB agonist is an antigen binding molecule comprising three ectodomains of 4-1BBL or fragments thereof and at least one antigen binding domain capable of specific binding to Fibroblast activation protein (FAP).

8. The method of claim 1, wherein the antigen binding domain capable of specific binding to a tumor-associated antigen is an antigen binding domain capable of specific binding to FAP comprising:
   (a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
   (b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

9. The method of claim 1, wherein the antigen binding domain capable of specific binding to a tumor-associated antigen is an antigen binding domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or wherein the antigen binding domain capable of specific binding to FAP comprises a heavy chain variable region ($V_H$FAP) comprising the amino acid sequence of SEQ ID NO:23 and a light chain variable region ($V_L$FAP) comprising the amino acid sequence of SEQ ID NO:24.

10. The method of claim 1, wherein the 4-1BB agonist is an antigen binding molecule comprising:
    (a) at least one antigen binding domain capable of specific binding to FAP,
    (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

11. The method of claim 1, wherein the 4-1BB agonist is an antigen binding molecule comprising:
    (a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and
    (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

12. The method of claim 1, wherein the 4-1BB agonist is an antigen binding molecule comprising a first heavy chain comprising the amino acid sequence of SEQ ID NO:41, a first light chain comprising the amino acid sequence of SEQ ID NO:42, a second heavy chain comprising the amino acid sequence of SEQ ID NO:43 and a second light chain comprising the amino acid sequence of SEQ ID NO:44.

13. The method of claim 1, wherein the 4-1BB agonist is an anti-FAP/anti-4-1BB bispecific antibody.

14. The method of claim 1, wherein the 4-1BB agonist is an antigen binding molecule comprising three ectodomains of 4-1BBL or fragments thereof and at least one antigen binding domain capable of specific binding to CEA.

15. The method of claim 1, wherein the antigen binding domain capable of specific binding to a tumor-associated antigen is an antigen binding domain capable of specific binding to CEA comprising (a) a heavy chain variable region ($V_H$CEA) comprising (i) CDR-H1 comprising the amino acid sequence of SEQ ID NO:33, (ii) CDR-H2 comprising the amino acid sequence of SEQ ID NO:34, and (iii)

CDR-H3 comprising the amino acid sequence of SEQ ID NO:35, and a light chain variable region (V$_L$CEA) comprising (iv) CDR-L1 comprising the amino acid sequence of SEQ ID NO:36, (v) CDR-L2 comprising the amino acid sequence of SEQ ID NO:37, and (vi) CDR-L3 comprising the amino acid sequence of SEQ ID NO:38.

16. The method of claim 1, wherein the antigen binding domain capable of specific binding to a tumor-associated antigen is an antigen binding domain capable of specific binding to CEA comprising a heavy chain variable region (V$_H$CEA) comprising the amino acid sequence of SEQ ID NO:39 and a light chain variable region (V$_L$CEA) comprising the amino acid sequence of SEQ ID NO:40.

17. The method of claim 1, wherein the 4-1BB agonist is an antigen binding molecule comprising:
    (a) at least one antigen binding domain capable of specific binding to CEA,
    (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

18. The method of claim 1, wherein the 4-1BB agonist is an antigen binding molecule comprising:
    (a) at least one Fab domain capable of specific binding to CEA comprising a heavy chain variable region (V$_H$-CEA) comprising the amino acid sequence of SEQ ID NO:39 and a light chain variable region (V$_L$CEA) comprising the amino acid sequence of SEQ ID NO:40, and
    (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

19. The method of claim 1, wherein the 4-1BB agonist is an anti-CEA/anti-4-1BB bispecific antibody.

20. The method of claim 1, wherein the 4-1BB agonist and the HER-2 targeting agent are administered together in a single composition or administered separately in two or more different compositions.

21. The method of claim 1, wherein the 4-1BB agonist acts synergistically with the HER-2 targeting agent.

22. The method of claim 1, wherein said cancer is gastric cancer.

23. The method of claim 7, wherein said cancer is gastric cancer.

24. The method of claim 8, wherein said cancer is gastric cancer.

* * * * *